US012685013B2

(12) United States Patent
Hayashi et al.

(10) Patent No.: US 12,685,013 B2
(45) Date of Patent: Jul. 14, 2026

(54) MATERIAL FOR PHOTOELECTRIC CONVERSION ELEMENTS FOR IMAGE PICKUP, AND PHOTOELECTRIC CONVERSION ELEMENT FOR IMAGE PICKUP

(71) Applicant: NIPPON STEEL CHEMICAL & MATERIAL CO., LTD., Tokyo (JP)

(72) Inventors: Kentaro Hayashi, Tokyo (JP); Munetomo Inoue, Tokyo (JP)

(73) Assignee: NIPPON STEEL CHEMICAL & MATERIAL CO., LTD., Tokyo (JP)

(*) Notice: Subject to any disclaimer, the term of this patent is extended or adjusted under 35 U.S.C. 154(b) by 360 days.

(21) Appl. No.: 18/561,141

(22) PCT Filed: Jul. 13, 2022

(86) PCT No.: PCT/JP2022/027617
§ 371 (c)(1),
(2) Date: Nov. 15, 2023

(87) PCT Pub. No.: WO2023/286816
PCT Pub. Date: Jan. 19, 2023

(65) Prior Publication Data

US 2024/0284787 A1 Aug. 22, 2024

(30) Foreign Application Priority Data

Jul. 15, 2021 (JP) ................................ 2021-117327

(51) Int. Cl.
*H10K 85/60* (2023.01)
*C07C 211/54* (2006.01)
(Continued)

(52) U.S. Cl.
CPC .......... *H10K 85/633* (2023.02); *C07C 211/54* (2013.01); *C07C 255/58* (2013.01);
(Continued)

(58) Field of Classification Search
CPC .. H10K 85/633; H10K 85/636; H10K 85/631; H10K 30/86; H10K 30/84; H10K 39/32
See application file for complete search history.

(56) References Cited

U.S. PATENT DOCUMENTS

2007/0063156 A1 3/2007 Hayashi
2018/0219047 A1* 8/2018 Tokuhara ................. G01J 5/24
(Continued)

FOREIGN PATENT DOCUMENTS

CN 108341795 A 7/2018
CN 111662258 A 9/2020
(Continued)

OTHER PUBLICATIONS

Aihara et al., "Research trends in organic imaging devices", NHK Science & Technology Research Laboratories R&D. (Mar. 2012), No. 132, p. 4-11, total 20 pages.
(Continued)

*Primary Examiner* — Alia Sabur
(74) *Attorney, Agent, or Firm* — Birch, Stewart, Kolasch & Birch, LLP

(57) ABSTRACT

Provided are a material that achieves higher sensitivity and higher resolution of a photoelectric conversion element for imaging, and a photoelectric conversion element for imaging using the above material. A material for a photoelectric conversion element for imaging, the material including a compound having a structure of the following general formula (1), wherein $Ar^1$ to $Ar^3$ represent an aromatic hydrocarbon group, an aromatic heterocyclic group, or a linked aromatic group in which two to six of these groups are linked, and at least two groups thereof have an aromatic ring structure represented by any of the following formulae (2) to (4). X represents O or S.

11 Claims, 1 Drawing Sheet

(51) Int. Cl.
*C07C 255/58* (2006.01)
*C07D 307/91* (2006.01)
*H10K 30/30* (2023.01)

(52) U.S. Cl.
CPC ......... *C07D 307/91* (2013.01); *H10K 85/636* (2023.02); *C07C 2603/42* (2017.05); *H10K 30/353* (2023.02); *H10K 85/622* (2023.02); *H10K 85/626* (2023.02); *H10K 85/6574* (2023.02)

(56) References Cited

U.S. PATENT DOCUMENTS

| | | | |
|---|---|---|---|
| 2019/0013469 | A1 | 1/2019 | Miyashita et al. |
| 2019/0288040 | A1 | 9/2019 | Ujre et al. |
| 2021/0119149 | A1 | 4/2021 | Negishi et al. |

FOREIGN PATENT DOCUMENTS

| | | | | | |
|---|---|---|---|---|---|
| CN | 111747893 | A | | 10/2020 | |
| JP | 2007-88033 | A | | 4/2007 | |
| JP | 2017-157731 | A | | 9/2017 | |
| JP | 2018-85427 | A | | 5/2018 | |
| JP | 2019-54228 | A | | 4/2019 | |
| JP | 2019-57704 | A | | 4/2019 | |
| JP | 2020-10024 | A | | 1/2020 | |
| KR | 10-2016-0024625 | A | | 3/2016 | |
| KR | 10-2018-0066855 | A | | 6/2018 | |
| KR | 20180066855 | A | * | 6/2018 | ........... H10K 50/181 |

OTHER PUBLICATIONS

Namba et al., "Photoelectric conversion film laminated type Technological trends in imaging devices". NHK Science & Technology Research Laboratories R&D, (Mar. 2019), No. 174, p. 4-17, total 34 pages.

Togashi et al., "Three-layer Staci(ed Color Image Sensor With 2.0-μm Pixel Size Using Organic Photoconductive Film", 2019 IEEE International Electron Devices Meeting (IEDM), (2019), p. 16.6.1-16.6.4.

* cited by examiner

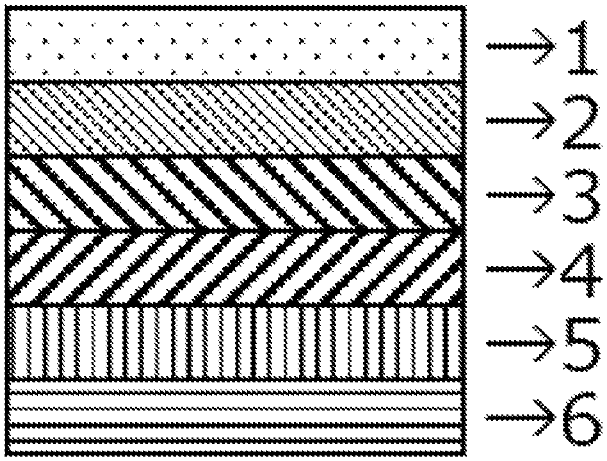
1
2
3
4
5
6

MATERIAL FOR PHOTOELECTRIC CONVERSION ELEMENTS FOR IMAGE PICKUP, AND PHOTOELECTRIC CONVERSION ELEMENT FOR IMAGE PICKUP

TECHNICAL FIELD

The present invention relates to a material for a photoelectric conversion element and a photoelectric conversion element using the same, and particularly to a material for a photoelectric conversion element useful for an imaging device.

In recent years, development of an organic electronic device using a thin film formed with an organic semiconductor is in progress. Examples thereof include an electroluminescent element, a solar cell, a transistor element, and a photoelectric conversion element. In particular, development of an organic EL element, which is an electroluminescent element with an organic substance, is most advanced among them. The applications for smartphones, TV and the like are in progress, and development for a purpose of further higher functionality is continuously conducted.

On the photoelectric conversion element, an element using a P-N junction of an inorganic semiconductor, such as silicon, has been conventionally developed and practically used, and made are investigations for high functionalization of a digital camera and a camera for a smartphone and investigation for application for a monitoring camera, a sensor for an automobile, and the like. However, problems for these various uses include improving sensitivity and micronizing a pixel (improving resolution). For the photoelectric conversion element using an inorganic semiconductor, a mainly adopted method for obtaining a color image is disposing color filters corresponding to RGB, which are the three primary colors of light, on a light receiving part of the photoelectric conversion element. This method has problems in terms of utilization efficiency of an incident light and resolution, because the method disposes the RGB color filters on a plane (Non Patent Literature 1 and 2).

As a solution for such problems of the photoelectric conversion element, a photoelectric conversion element using an organic semiconductor instead of the inorganic semiconductor is developed (Non Patent Literature 1 and 2). This utilizes an ability to selectively absorb only light having a specific wavelength region with high sensitivity that the organic semiconductor has, and proposed is stacking photoelectric conversion elements composed of organic semiconductors corresponding to the three primary colors of light to solve the problem of improving the sensitivity and improving the resolution. An element in which a photoelectric conversion element composed of the organic semiconductor and a photoelectric conversion element composed of the inorganic semiconductor are stacked is also proposed (Non Patent Literature 3).

Here, the photoelectric conversion element composed of the organic semiconductor is an element having a photoelectric conversion layer composed of a thin film of the organic semiconductor between two electrodes, wherein a hole blocking layer and/or an electron blocking layer is disposed between the photoelectric conversion layer and the two electrodes, as necessary. In the photoelectric conversion element, light having a desired wavelength is absorbed in the photoelectric conversion layer to generate an exciton, and then charge separation of the exciton generates a hole and an electron. Thereafter, the hole and the electron move toward each electrode to convert the light into an electric signal. For a purpose of accelerating this process, a method of applying a bias voltage between both the electrodes is commonly used, but one of objects is reducing a leakage current from both the electrodes generated by applying the bias voltage. Accordingly, it can be mentioned that controlling the move of the hole and the electron in the photoelectric conversion element is a key to exhibit characteristic of the photoelectric conversion element.

The organic semiconductor used for each layer of the photoelectric conversion element can be classified into a P-type organic semiconductor and an N-type organic semiconductor. The P-type organic semiconductor is used as a hole transport material, and the N-type organic semiconductor is used as an electron transport material. To control the move of the hole and the electron in the photoelectric conversion element, made are various developments of an organic semiconductor having appropriate physical properties such as hole mobility, electron mobility, an energy value of a highest occupied molecular orbital (HOMO), and an energy value of a lowest unoccupied molecular orbital (LUMO). However, the organic semiconductor still has insufficient characteristics, and has not been utilized in commercial practice.

Patent literature 1 proposes an element using quinacridone as the P-type organic semiconductor and subphthalocyanine chloride as the N-type organic semiconductor for the photoelectric conversion layer, and an indolocarbazole derivative for a first buffer layer disposed between the photoelectric conversion layer and the electrode.

Patent literature 2 proposes an element using, for the photoelectric conversion layer, a chrysenodithiophene derivative as the P-type organic semiconductor and fullerenes or a subphthalocyanine derivative as the N-type organic semiconductor.

Patent literature 3 proposes an element using a benzodifuran derivative for the electron blocking layer disposed between the photoelectric conversion layer and the electrode.

Patent literature 4 discloses that an allylamine compound having a specific substituent is used for an electron blocking layer of an organic photoelectric conversion element.

Patent literature 5 and 6 discloses that an allylamine compound is used as an organic EL material, but there is no disclosure as the material for a photoelectric conversion element.

CITATION LIST

Patent Literature

Patent Literature 1
JP 2018-85427 (A)
Patent Literature 2
JP 2019-54228 (A)
Patent Literature 3
JP 2019-57704 (A)
Patent Literature 4
JP 2017-157731 (A)
Patent Literature 5
KR 2018-0066855 A
Patent Literature 6
CN 108341795 A

Non Patent Literature

Non Patent Literature 1
NHK Science & Technology Research Laboratories R&D No. 132, pp. 4-11 (2012.3)

Non Patent Literature 2
NHK Science & Technology Research Laboratories R&D No. 174, pp. 4-17 (2019.3)
Non Patent Literature 3
2019 IEEE International Electron Devices Meeting (IEDM), pp. 16.6.1-16.6.4 (2019)

SUMMARY OF INVENTION

Technical Problem

In the use of the photoelectric conversion element for imaging for highly functionalizing a digital camera and a camera for a smartphone and for application for a monitoring camera, a sensor for an automobile, and the like, challenges are further higher sensitivity and higher resolution. In view of such a circumstance, an object of the present invention is to provide a material that achieves higher sensitivity and higher resolution of the photoelectric conversion element for imaging, and a photoelectric conversion element for imaging using the same.

Solution to Problem

The present inventors have made intensive investigation, and consequently found that using a specific aromatic amine compound efficiently proceeds a process of generating a hole and an electron by charge separation of an exciton in a photoelectric conversion layer, and a process of moving of the hole and the electron in the photoelectric conversion element. This finding has led to the completion of the present invention.

The present invention is a material for a photoelectric conversion element for imaging, the material comprising a compound represented by the following general formula (1):

[C1]

(1)

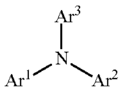

wherein $Ar^1$ to $Ar^3$ each independently represent a substituted or unsubstituted aromatic hydrocarbon group having 6 to 30 carbon atoms, a substituted or unsubstituted aromatic heterocyclic group having 3 to 30 carbon atoms, or a substituted or unsubstituted linked aromatic group in which two to six aromatic rings of the aromatic hydrocarbon group or the aromatic heterocyclic group are linked, and at least two groups of $Ar^1$ to $Ar^3$ independently have an aromatic ring structure represented by any of the following formulae (2) to (4). This aromatic ring structure optionally has a substituent.

[C2]

(2)

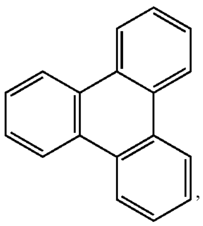
,

-continued (3)

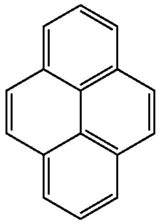
, (4)

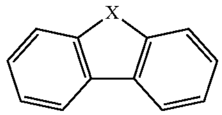

(4)

X represents O or S. The aromatic ring structure may be bonded to an adjacent group or N in the general formula (1) at any position. The aromatic ring structure may have a bond at any position, and may have a plurality of bonds.

In the material for a photoelectric conversion element, an energy level of highest occupied molecular orbital (HOMO) obtained by structural optimization calculation with a density functional calculation B3LYP/6-31G (d) is preferably −4.5 eV or lower, or an energy level of lowest unoccupied molecular orbital (LUMO) is preferably −2.5 eV or higher.

The material for a photoelectric conversion element preferably has a hole mobility of $1\times10^{-6}$ $cm^2/Vs$ or more, or is preferably amorphous.

In the general formula (1), at least two groups of $Ar^1$ to $Ar^3$ preferably have any one of the aromatic ring structure represented by formula (2) or (3), or at least two groups of $Ar^1$ to $Ar^3$ preferably have any one of the aromatic ring structure represented by formula (2) or (4). Furthermore, at least another group of $Ar^1$ to $Ar^3$ is preferably the aromatic ring structure represented by formula (2), and at least another group of $Ar^1$ to $Ar^3$ preferably has any one of the aromatic ring structure represented by formula (2) or (4).

The material for a photoelectric conversion element may be used as a hole transport material.

The present invention is a photoelectric conversion element for imaging, comprising a photoelectric conversion layer and an electron blocking layer between two electrodes, wherein at least one layer of the photoelectric conversion layer or the electron blocking layer contains the above material for a photoelectric conversion element.

In the photoelectric conversion element of the present invention, the electron blocking layer may contain the above material for a photoelectric conversion element, and the photoelectric conversion layer may contain an electron transport material.

Advantageous Effect of Invention

Using the material for a photoelectric conversion element for imaging of the present invention can achieve appropriate move of the hole and the electron in the photoelectric conversion element for imaging, and consequently enables to reduce a leakage current generated by applying a bias voltage during the conversion of light into electric energy. As a result, it is considered that a photoelectric conversion element that achieves a low dark current value and a high contrast ratio has been obtained. Therefore, the material of the present invention is useful as a material for a photoelectric conversion element for a photoelectric-converting film-stacked imaging device.

BRIEF DESCRIPTION OF DRAWING

FIG. 1 is a sectional schematic view illustrating a structure example of a photoelectric conversion element used in the present invention.

DESCRIPTION OF EMBODIMENTS

The photoelectric conversion element for imaging of the present invention is a photoelectric conversion element having at least one organic layer between two electrodes and converting light into electric energy. This organic layer contains the material for a photoelectric conversion element for imaging comprising the compound represented by the general formula (1). Hereinafter, the material for a photoelectric conversion element for imaging comprising the compound represented by the general formula (1) is also referred to as a material for a photoelectric conversion element, a material of the present invention, or the compound represented by the general formula (1).

The compound represented by the general formula (1) will be described below.

In the general formula (1), $Ar^1$ to $Ar^3$ each independently represent a substituted or unsubstituted aromatic hydrocarbon group having 6 to 30 carbon atoms, a substituted or unsubstituted aromatic heterocyclic group having 3 to 30 carbon atoms, or a substituted or unsubstituted linked aromatic group in which two to six aromatic groups of the aromatic hydrocarbon group or the aromatic heterocyclic group are linked. Note that, at least two groups of $Ar^1$ to $Ar^3$ independently have an aromatic ring structure represented by any of the following formulae (2) to (4).

Examples of the aromatic hydrocarbon group having 6 to 30 carbon atoms include groups obtained by removing one hydrogen from a known aromatic hydrocarbon. Examples of the aromatic hydrocarbon include: monocyclic aromatic hydrocarbons, such as benzene; bicyclic aromatic hydrocarbons, such as naphthalene; tricyclic aromatic hydrocarbons, such as indacene, biphenylene, phenalene, anthracene, phenanthrene, and fluorene; tetracyclic aromatic hydrocarbons, such as fluoranthene, acephenanthrylene, aceanthrylene, triphenylene, pyrene, chrysene, tetraphene, tetracene, and pleiadene; and pentacyclic aromatic hydrocarbons, such as picene, perylene, pentaphene, pentacene, tetraphenylene, and naphthoanthracene. The hydrocarbon aromatic group is preferably benzene, naphthalene, anthracene, triphenylene, or pyrene.

Examples of the aromatic heterocyclic group having 3 to 30 carbon atoms include groups obtained by removing one hydrogen from an aromatic heterocyclic compound. Examples of the aromatic heterocyclic compound include: nitrogen-containing aromatic compounds having a pyrrole ring, such as pyrrole, pyrrolopyrrole, indole, pyrroloindole, benzoindole, naphthopyrrole, isoindole, pyrroloisoindole, benzoisoindole, naphthoisopyrrole, carbazole, benzocarbazole, indoloindole, indolocarbazole, carbazolocarbazole, benzofurocarbazole, benzothienocarbazole, and carboline; sulfur-containing aromatic compounds having a thiophene ring, such as thiophene, benzothiophene, naphthothiophene, dibenzothiophene, benzothienonaphthalene, benzothienobenzothiophene, benzothienodibenzothiophene, dinaphthothiophene, dinaphthothienothiophene, and naphthobenzothiophene; oxygen-containing aromatic compounds having a furan ring, such as furan, benzofuran, naphthofuran, dibenzofuran, benzofuronaphthalene, benzofurobenzofuran, benzofurodibenzofuran, dinaphthofuran, dinaphthofuranofuran, and naphthobenzofuran; pyridine, pyrimidine, triazine, quinoline, isoquinoline, quinazoline, and quinoxaline. The aromatic heterocyclic compound is preferably dibenzofuran, dibenzothiophene, carbazole, pyridine, pyrimidine, triazine, quinazoline, benzothienodibenzothiophene, benzofurodibenzofuran, benzofurocarbazole, or benzothienocarbazole.

The linked aromatic group herein refers to an aromatic group in which aromatic rings of two or more aromatic groups are bonded and linked with a single bond. These linked aromatic groups may be linear or branched. A linking position in linking the benzene rings each other may be any of ortho, meta, and para, but para-liking or meta-linking is preferable. The aromatic group may be an aromatic hydrocarbon group or an aromatic heterocyclic group. The plurality of the aromatic groups may be same as or different from each other.

When $Ar^1$ to $Ar^3$ represent the aromatic hydrocarbon group, the aromatic heterocyclic group, or the linked aromatic group, these groups optionally have a substituent. Examples of the substituent include deuterium, an alkyl group having 1 to 20 carbon atoms, a cyano group, and an alkylsilyl group. The alkyl group having 1 to 20 carbon atoms may be any of linear, branched, and cyclic alkyl groups, and is preferably deuterium, a linear, branched, or cyclic alkyl group having 1 to 10 carbon atoms, or a cyano group. Specific examples thereof include: linear saturated hydrocarbon groups, such as a methyl group, an ethyl group, a n-propyl group, a n-butyl group, a n-pentyl group, a n-hexyl group, a n-octyl group, a n-dodecyl group, a n-tetradecyl group, and a n-octadecyl group; branched saturated hydrocarbon groups, such as an isopropyl group, an isobutyl group, a neopentyl group, a 2-ethylhexyl group, and a 2-hexyloctyl group; and saturated alicyclic hydrocarbon groups, such as a cyclopentyl group, a cyclohexyl group, a cyclooctyl group, a 4-butylcyclohexyl group, and a 4-dodecylcyclohexyl group.

At least two groups of $Ar^1$ to $Ar^3$ have the aromatic ring structure represented by formulae (2) to (4). At least two groups of $Ar^1$ to $Ar^3$ preferably have any one of the aromatic ring structure selected from the formula (2) or (3), or preferably have any one of the aromatic ring structure selected from the formula (2) or (4). Furthermore, at least one group of $Ar^1$ to $Ar^3$ is preferably the aromatic ring structure represented by formula (2), and at least another group of $Ar^1$ to $Ar^3$ preferably has any one of the aromatic ring structure represented by formula (2) or (4). $Ar^1$ to $Ar^3$ furthermore preferably have two or more groups having the aromatic ring structure represented by formula (2).

In the formula (4), X represents O or S, and preferably represents O.

The group having the aromatic ring structure represented by formulae (2) to (4) optionally has a substituent, and may be a linked aromatic group. In a case of the linked aromatic group, at least one of aromatic groups constituting the linked aromatic group has the aromatic ring structure. In this case, the aromatic ring structure may be present at the middle or end of the linked aromatic group, but preferably present at the end. This group having the aromatic ring structure is included in any of the substituted or unsubstituted aromatic hydrocarbon group having 6 to 30 carbon atoms, the substituted or unsubstituted aromatic heterocyclic group having 3 to 30 carbon atoms, or the substituted or unsubstituted linked aromatic group in which two to six aromatic groups of the aromatic hydrocarbon group or the aromatic heterocyclic group are linked.

The aromatic ring structure may be a terminal group having one bond or may be a linking group having a plurality of bonds, but preferably a terminal group having one bond.

Preferable specific examples of the compound represented by the general formula (1) being the material for a photoelectric conversion element of the present invention are shown below, but the material is not limited thereto.

[C3]

T1

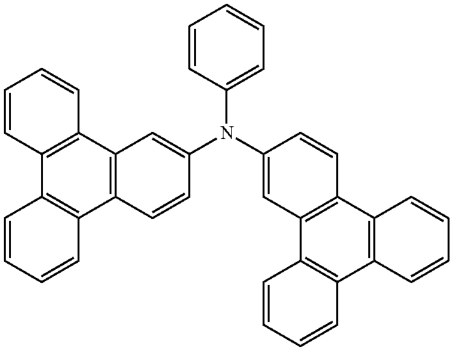

T2

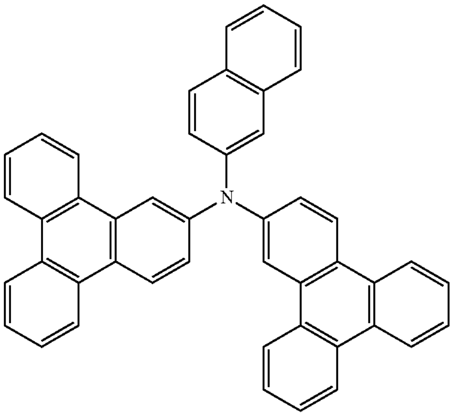

T3

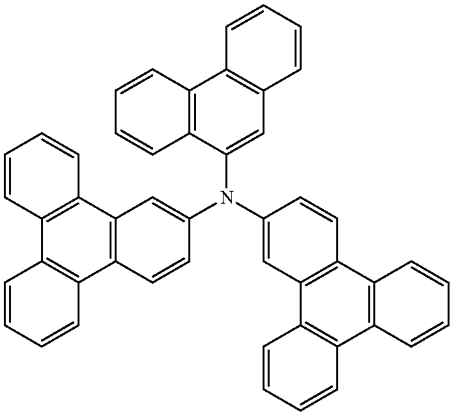

-continued

T4

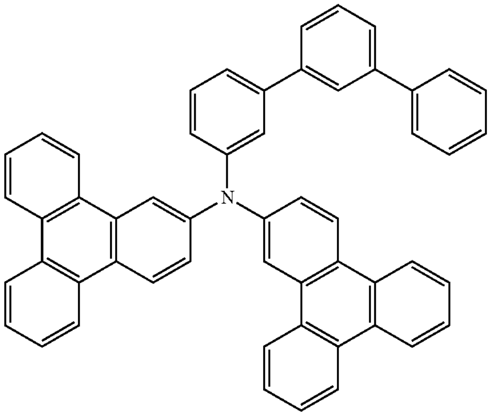

T5

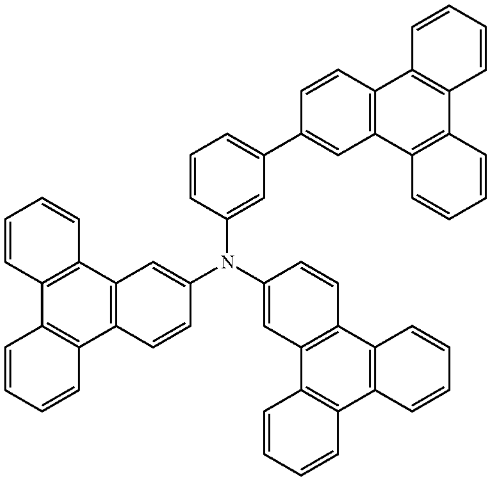

T6

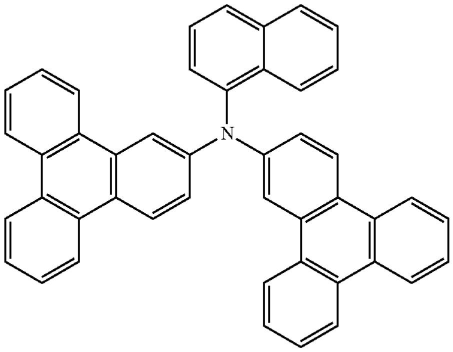

-continued
T7
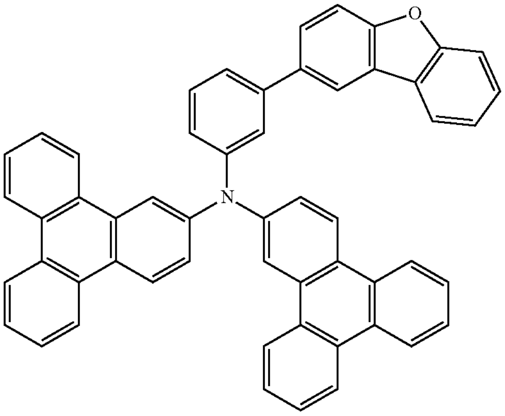
T8
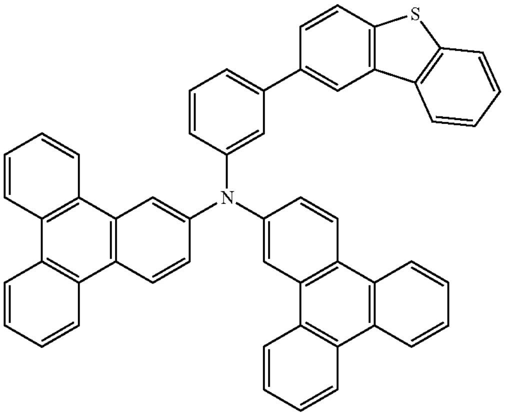
T9
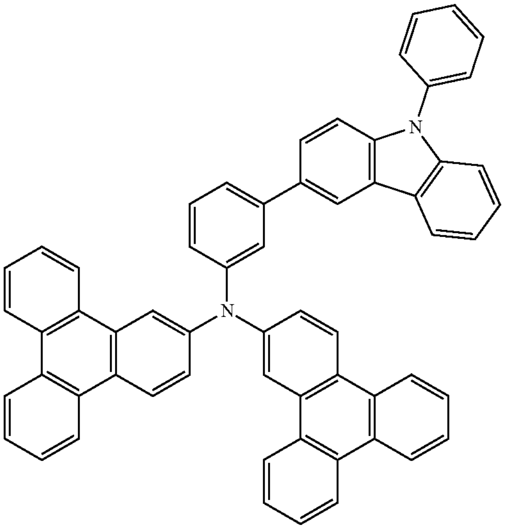
-continued
T10
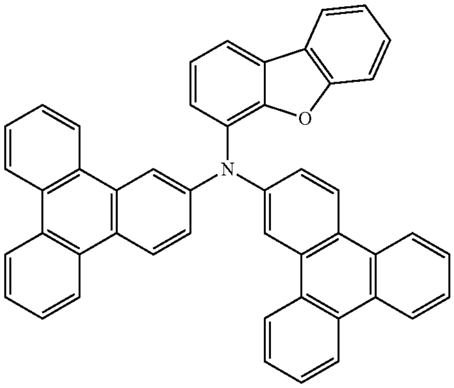
T11
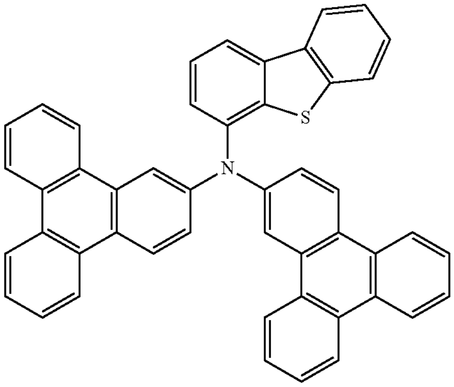
T12
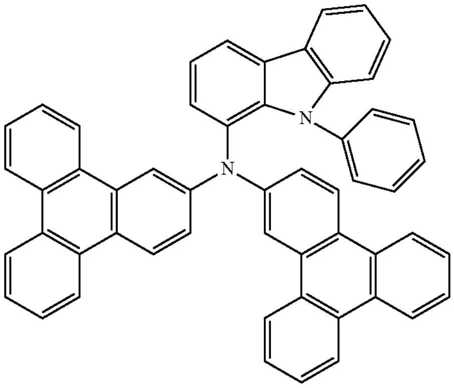
T13
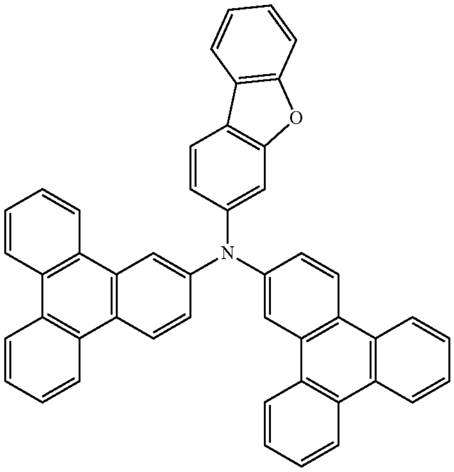

-continued
T14
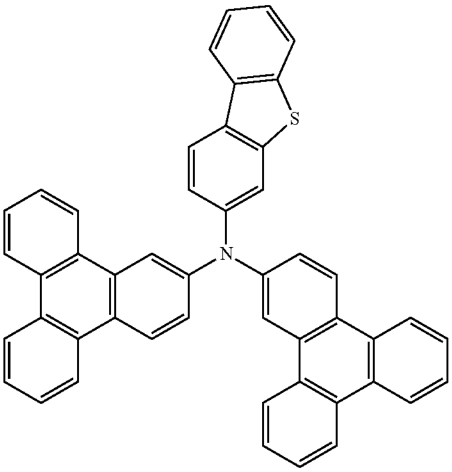
T15
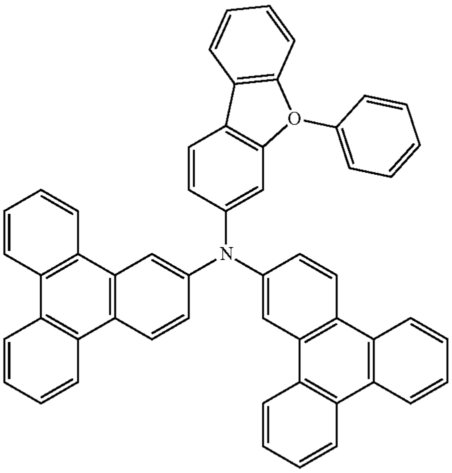
[C4]
T16
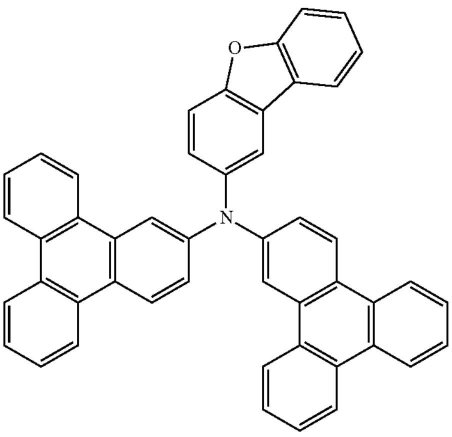
-continued
T17
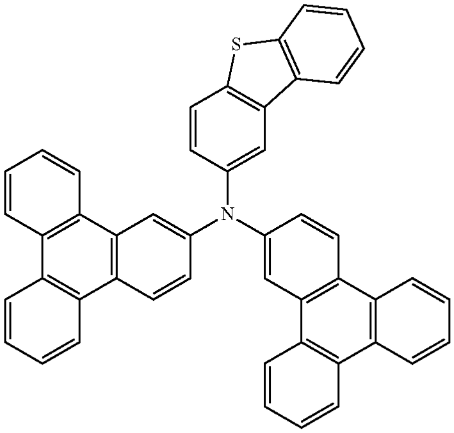
T18
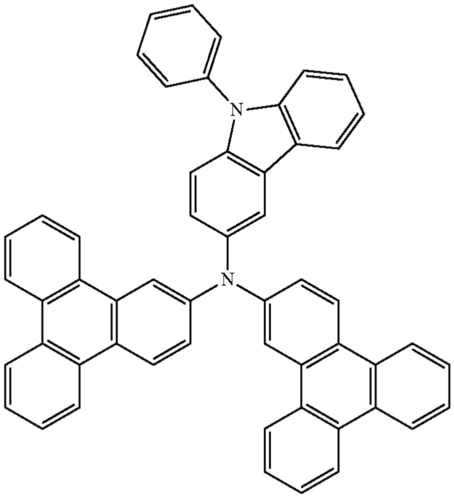
T19
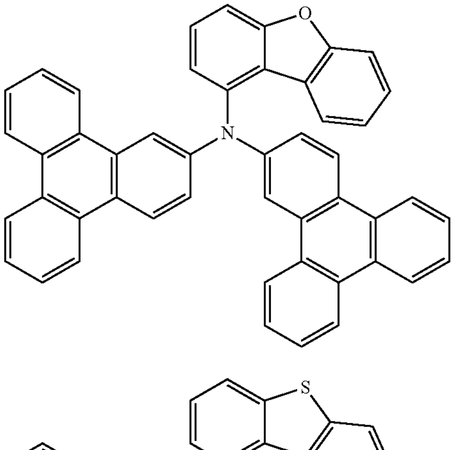
T20
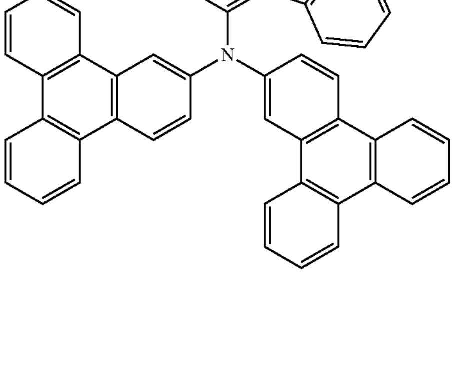

T21
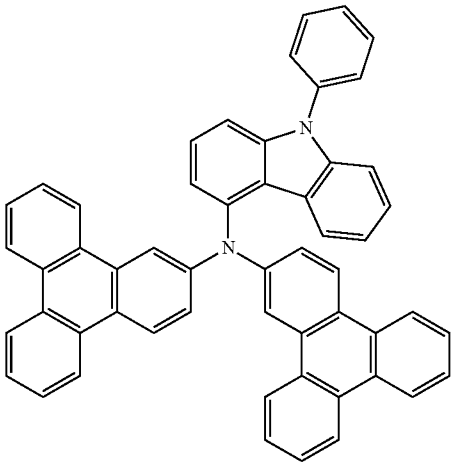
T22
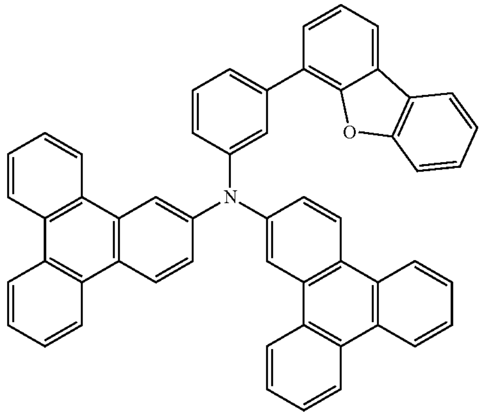
T23
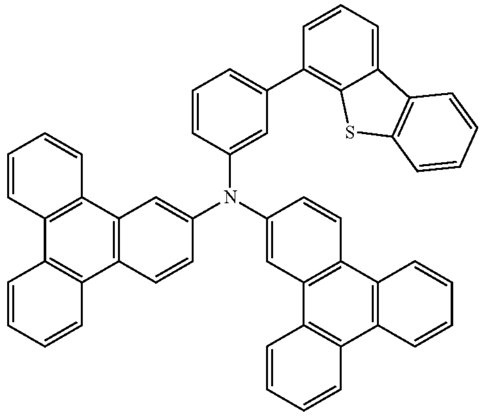
T24
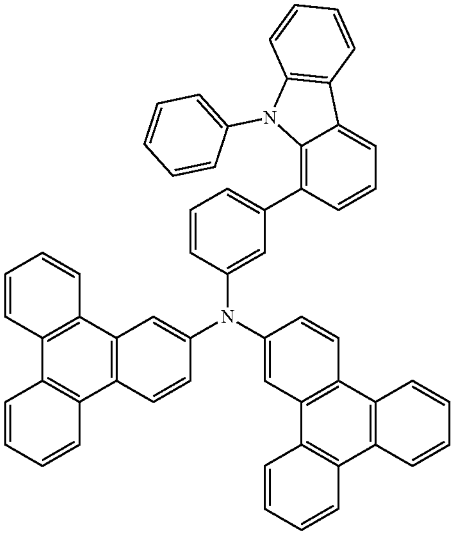
T25
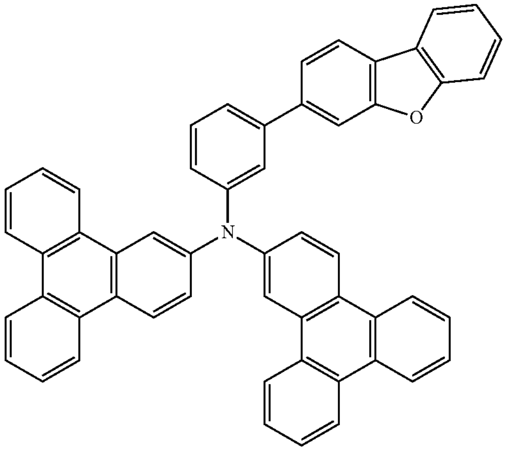
T26
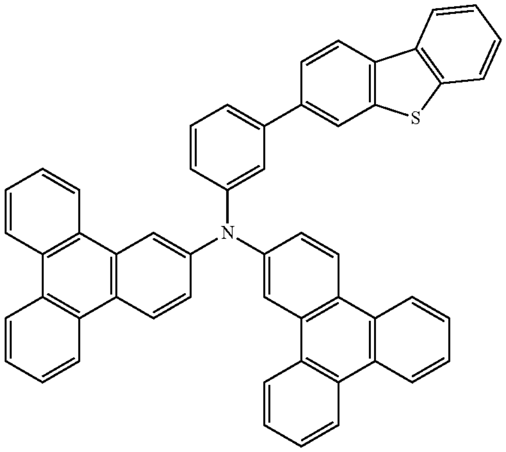

-continued
T27
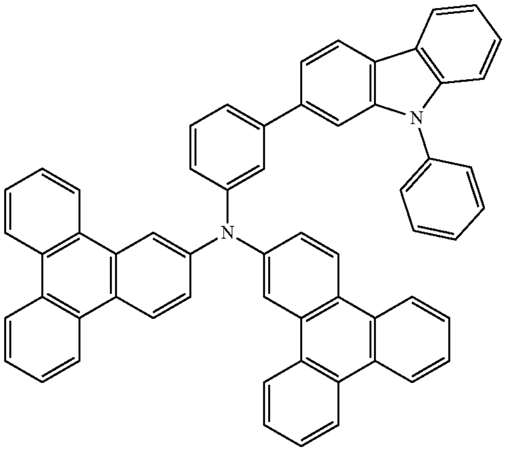
T28
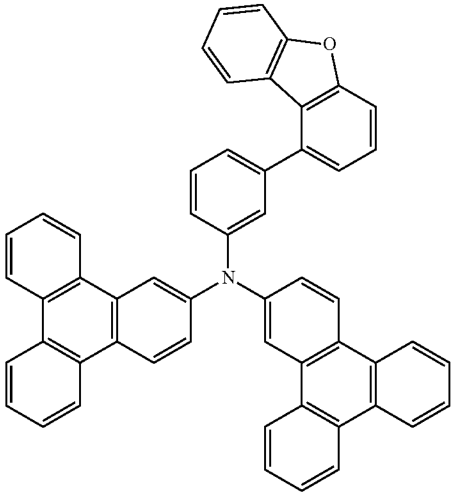
T29
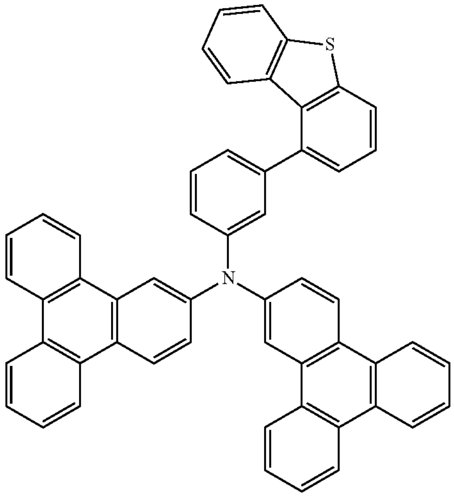
-continued
T30
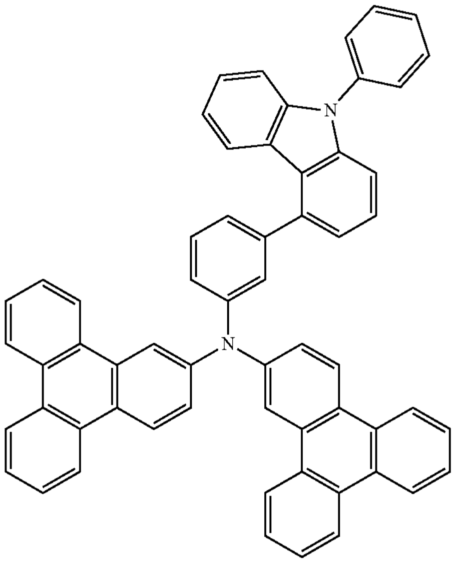
[C5]
T31
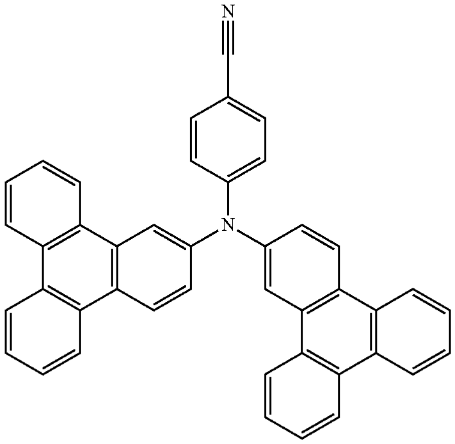
T32
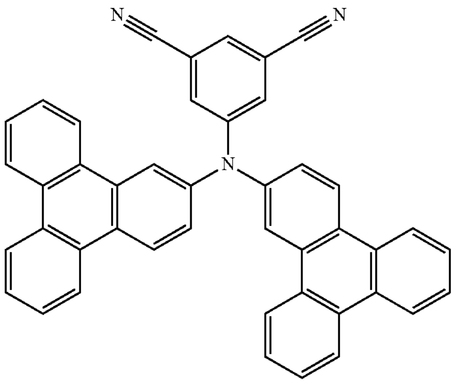

-continued
T33
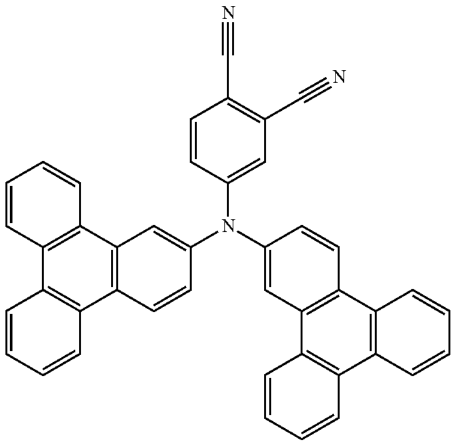
T34
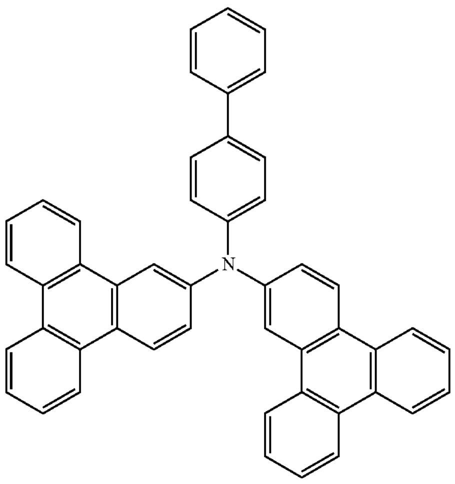
T35
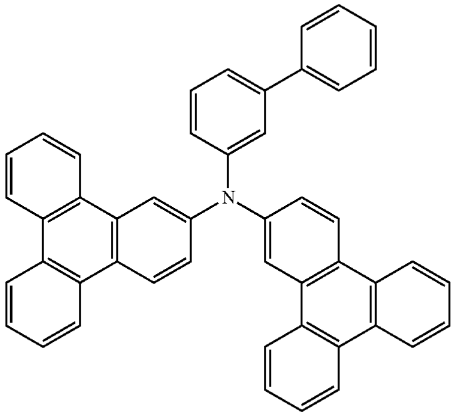
-continued
T36
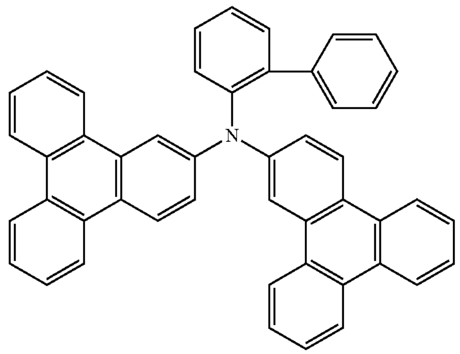
T37
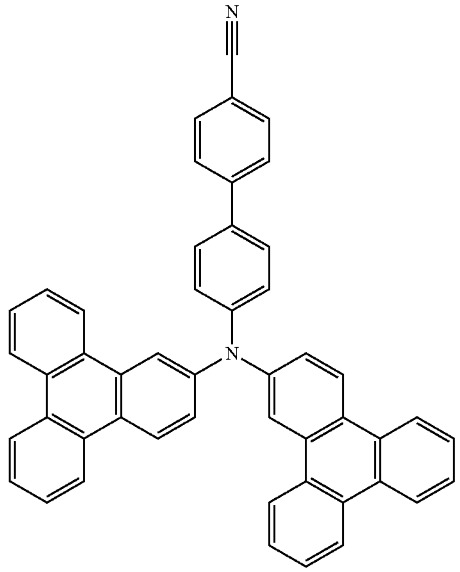
T38
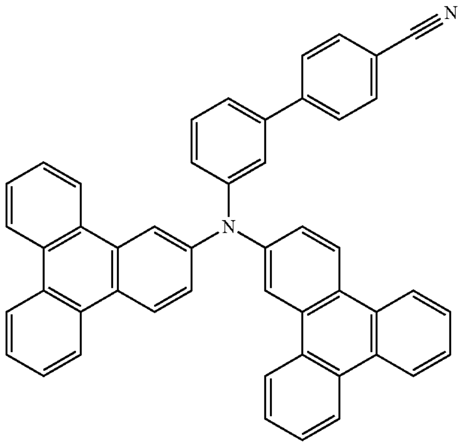

-continued
T39
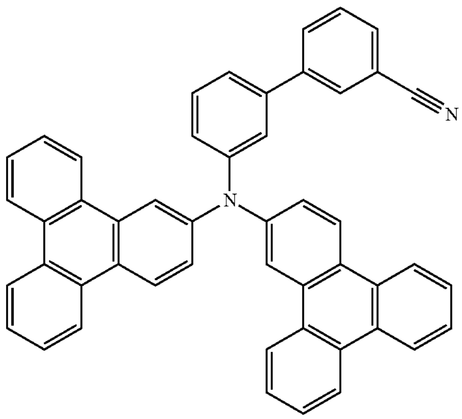
T40
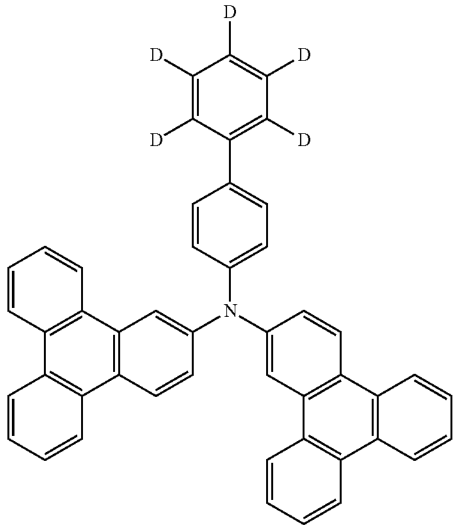
T41
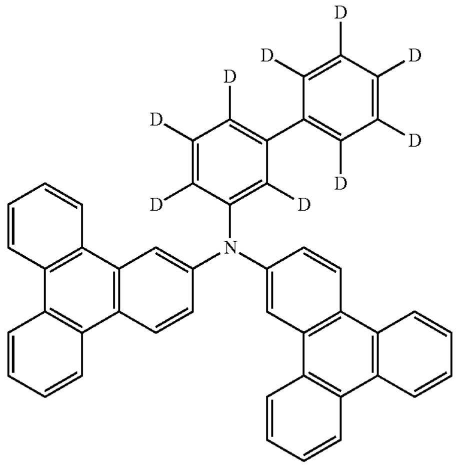
-continued
T42
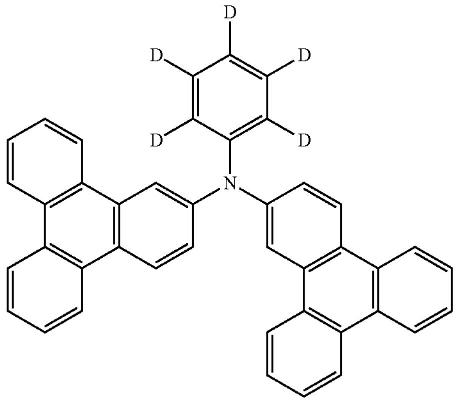
T43
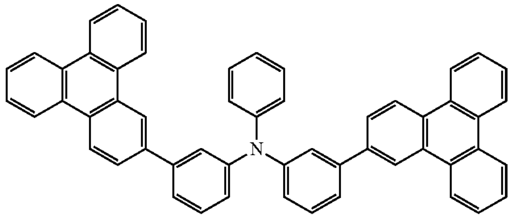
T44
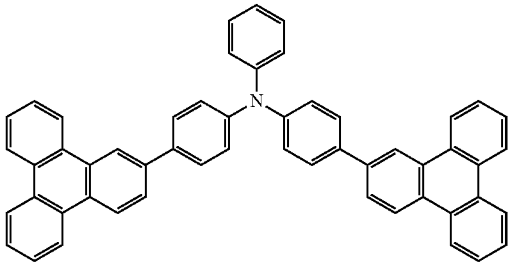
T45
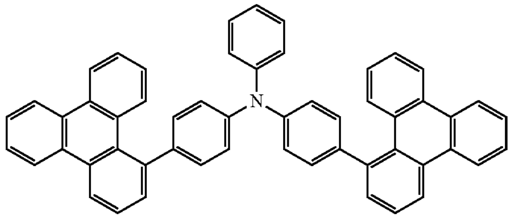
T46
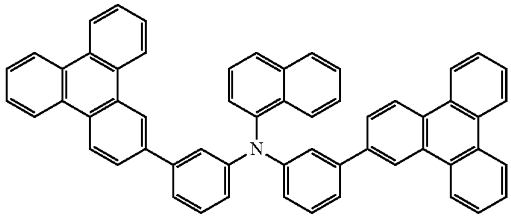
T47
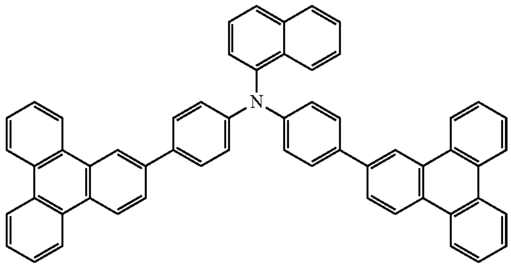

-continued
T48
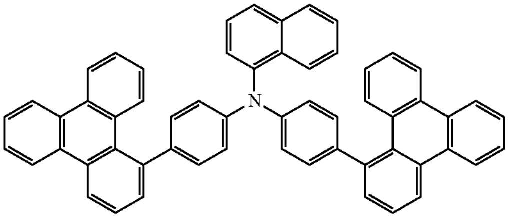
[C6]
T49
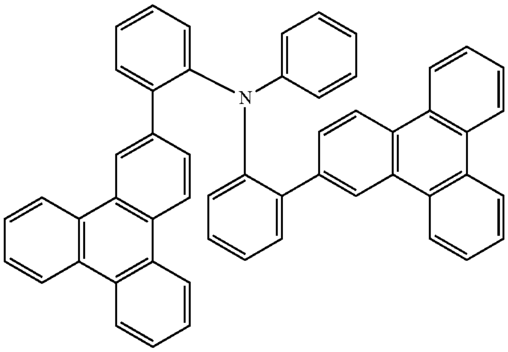
T50
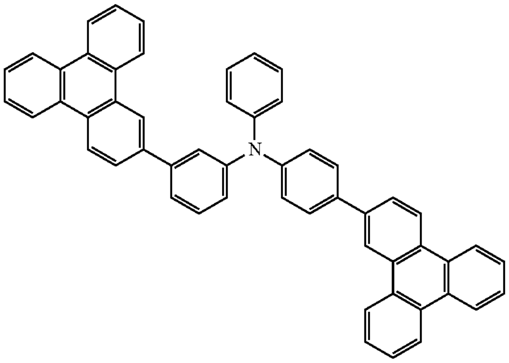
T51
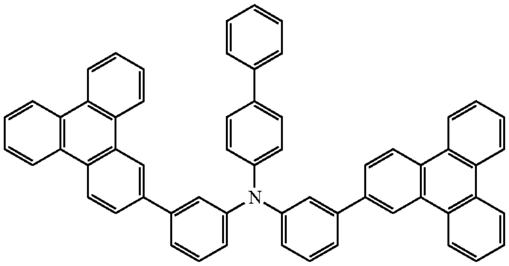
-continued
T52
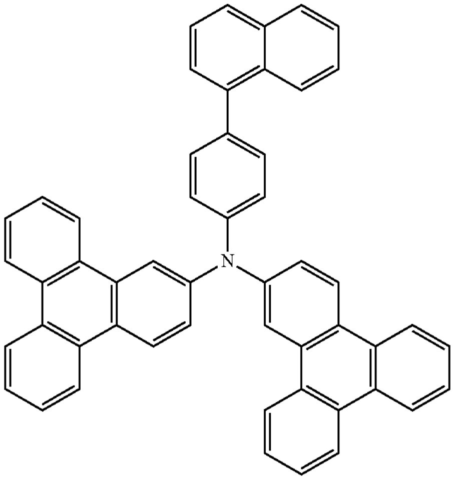
T53
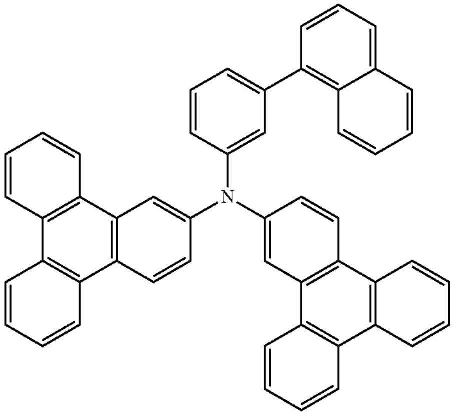
T54
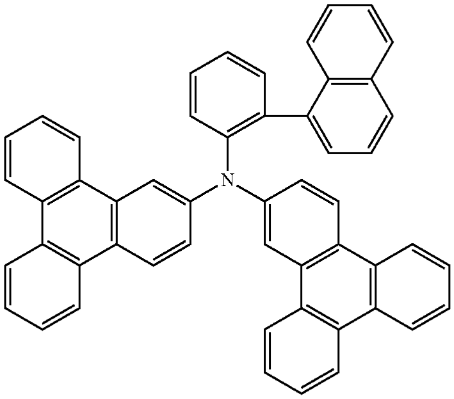
T55
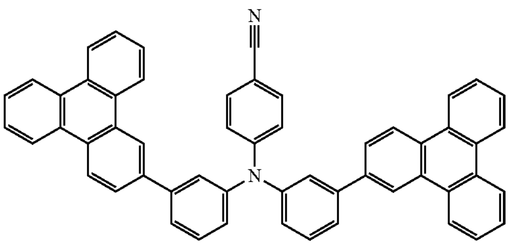

-continued
T56
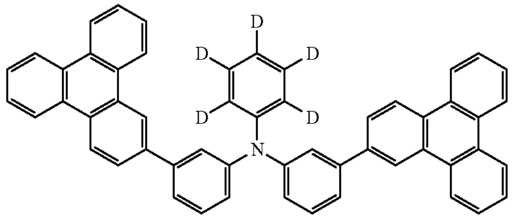
T57
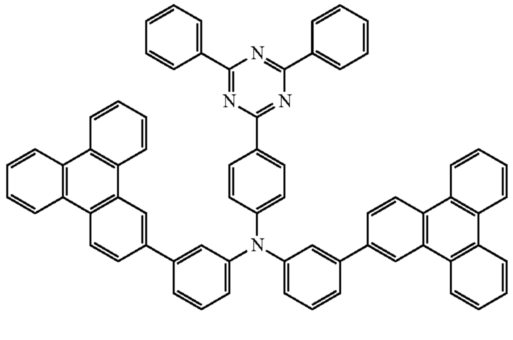
T58
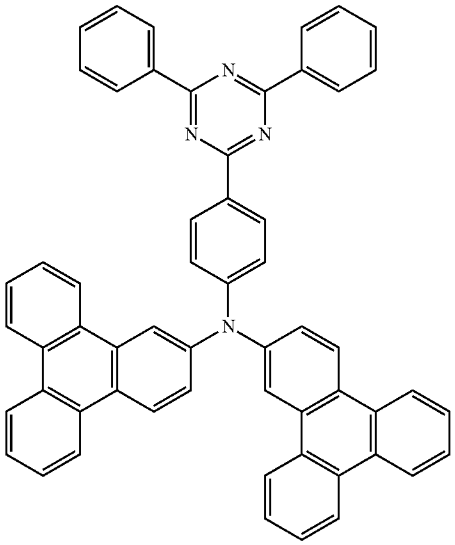
-continued
T59
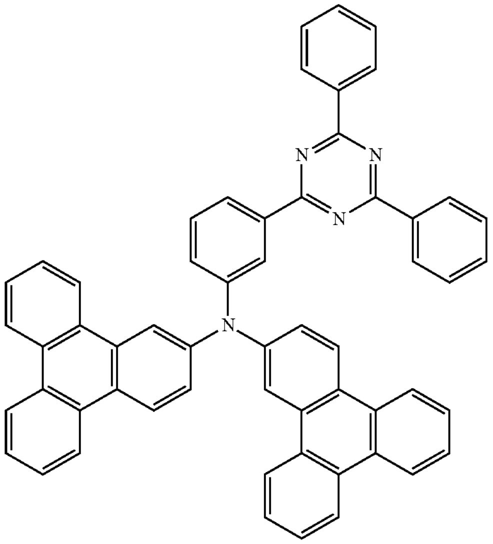
T60
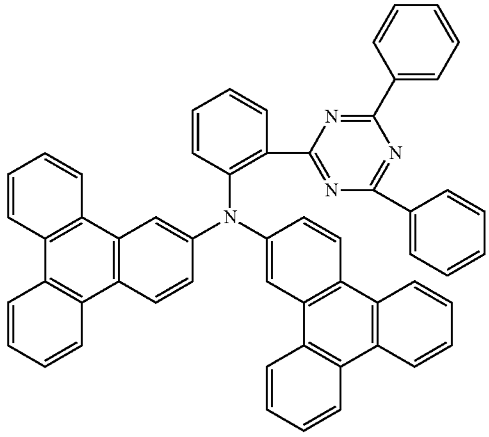
T61
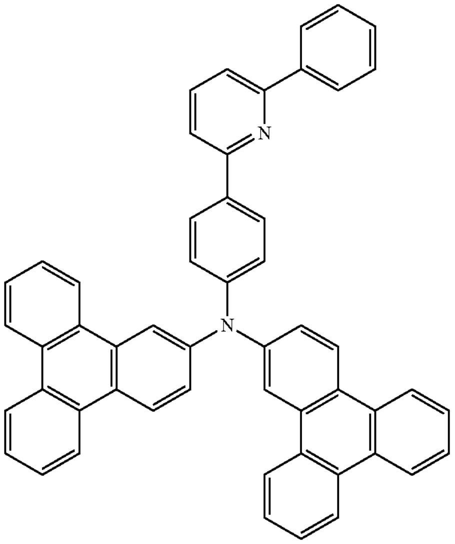

-continued
T62
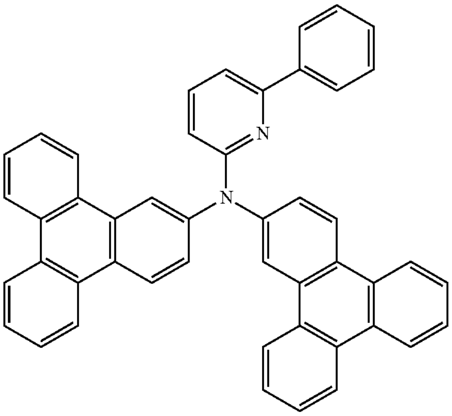
T63
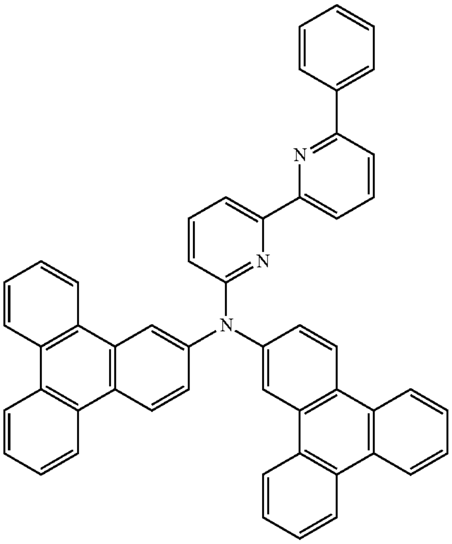
T64
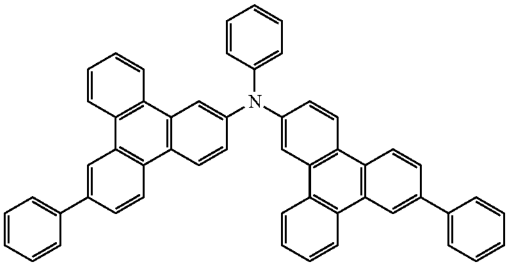
T65
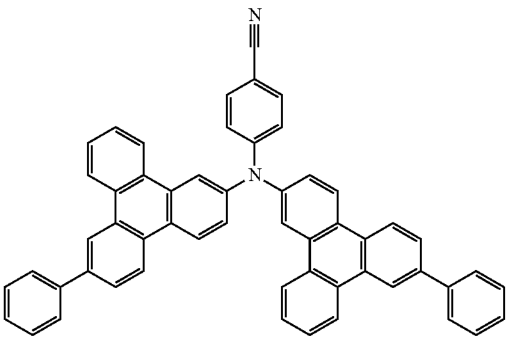
-continued
T66
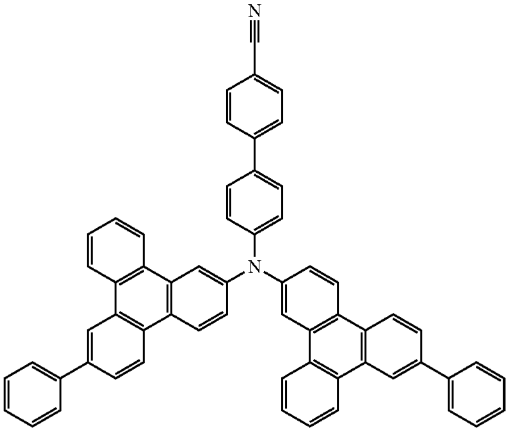
T67
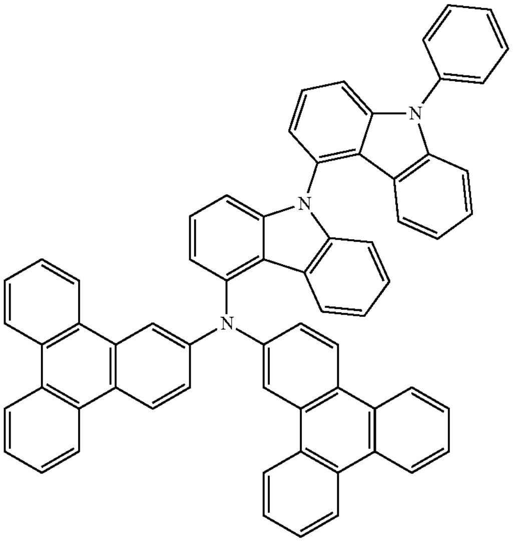
T68
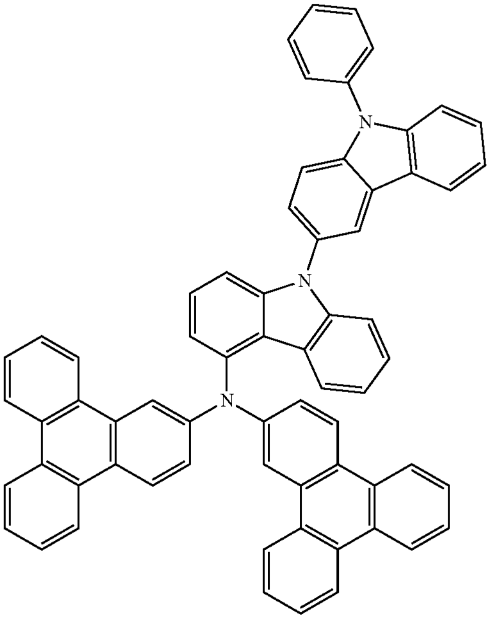

-continued
T69
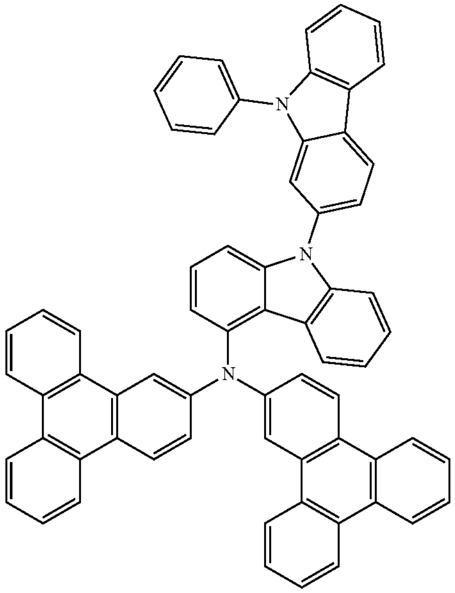
T70
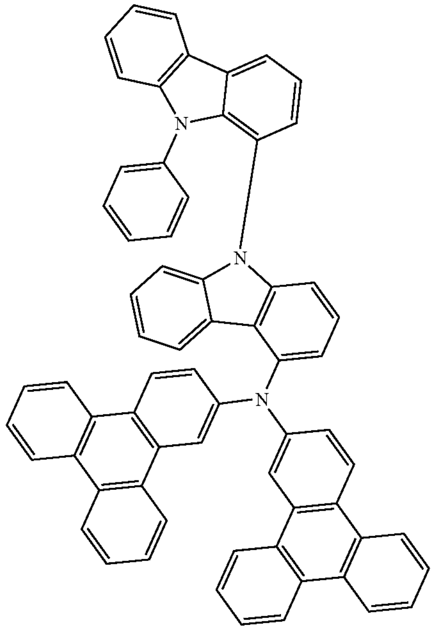
-continued
T71
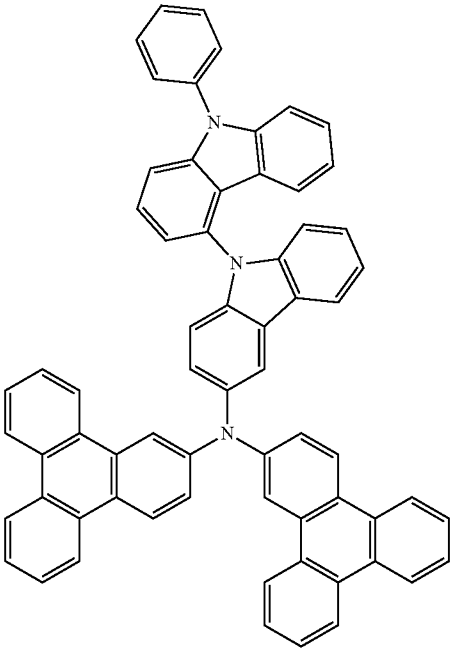
T72
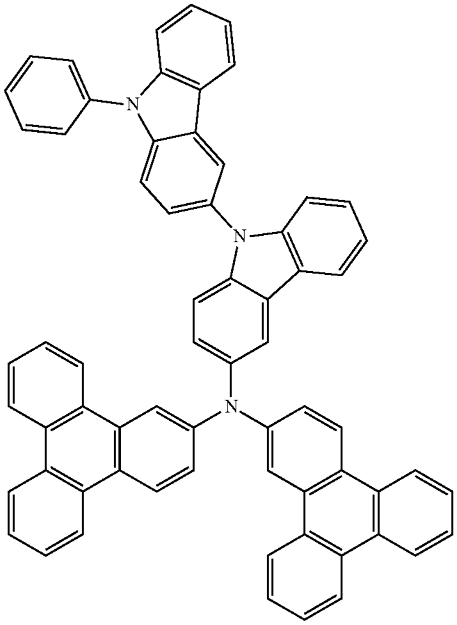

-continued
T73
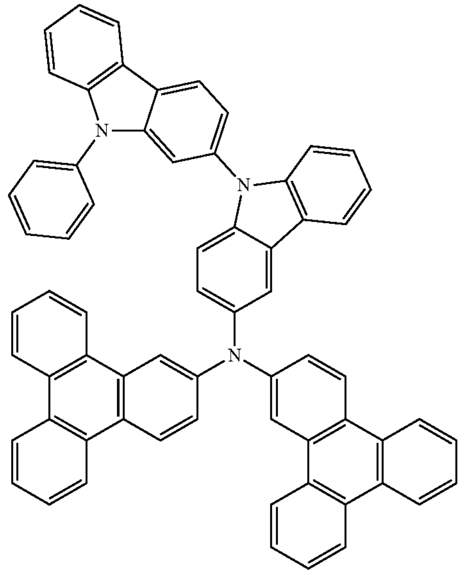
T74
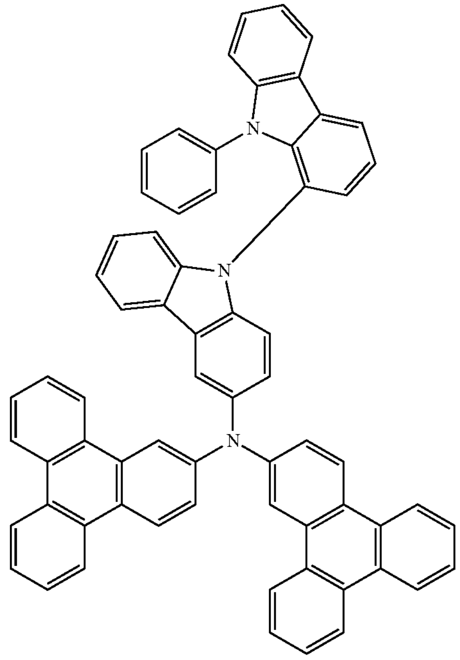
-continued
T75
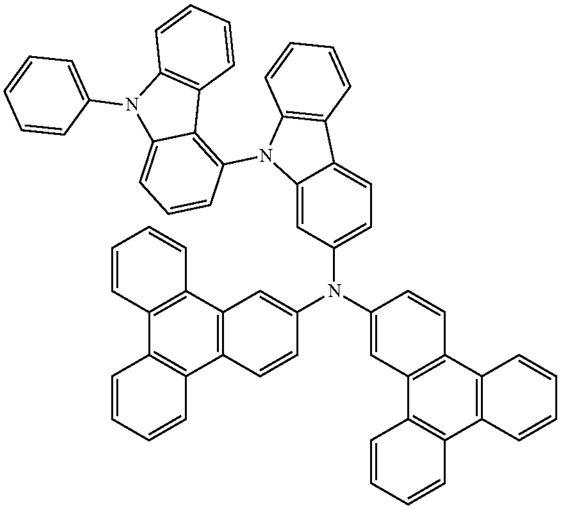
T76
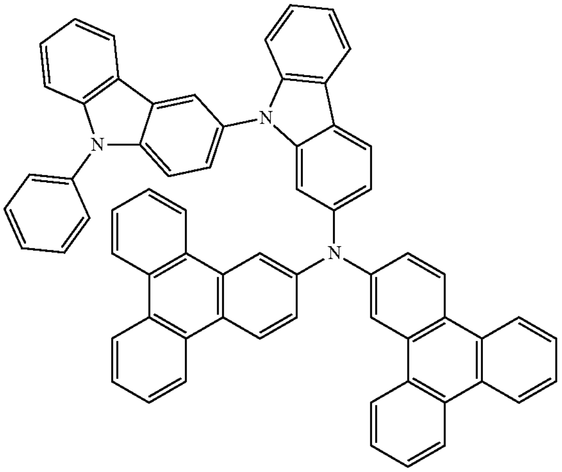
T77
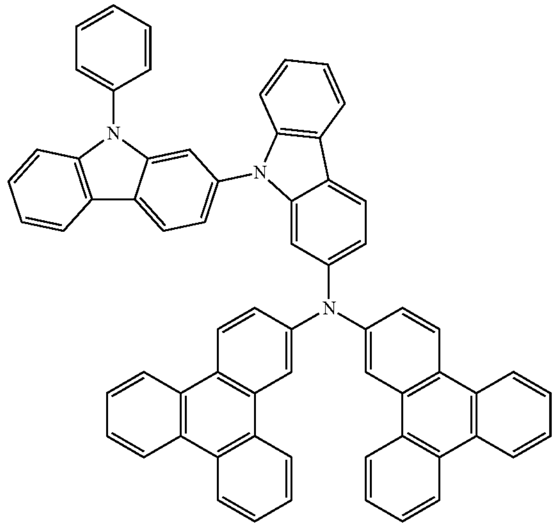

-continued
T78
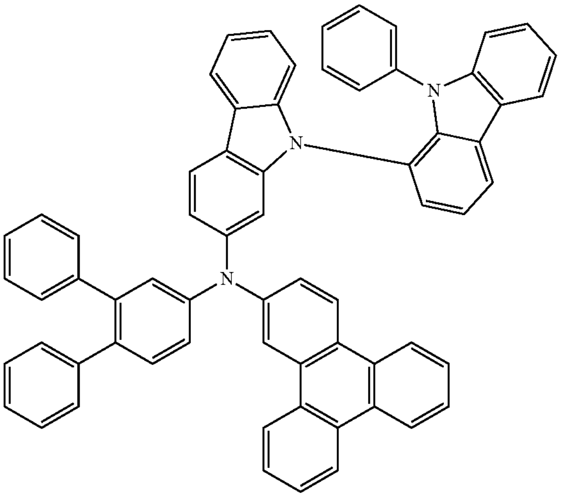
T79
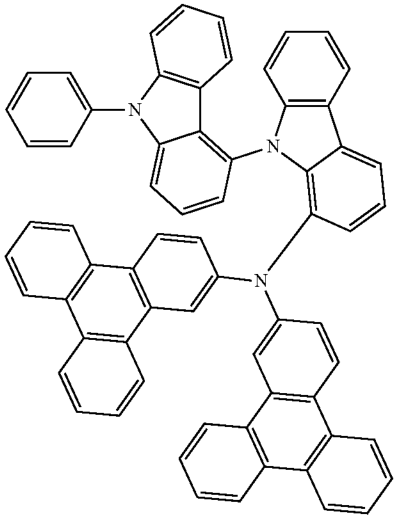
T80
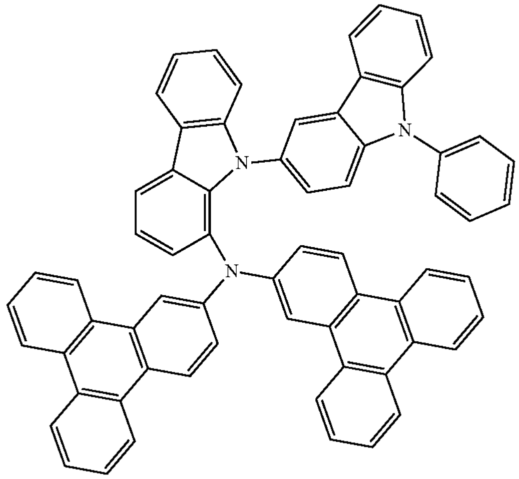
-continued
T81
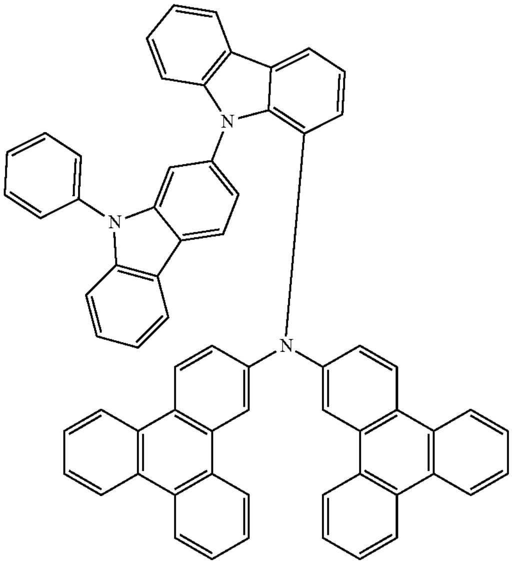
T82
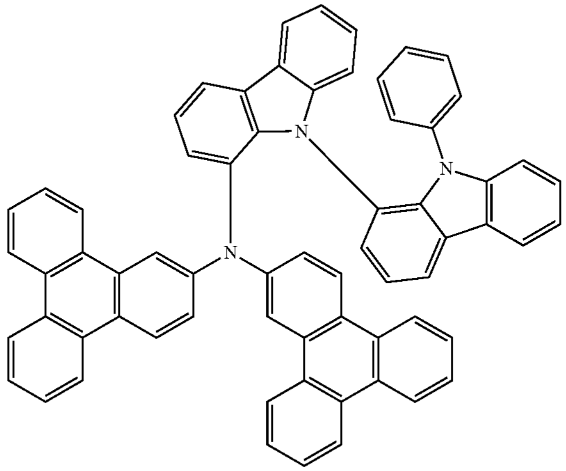
[C7]
P1
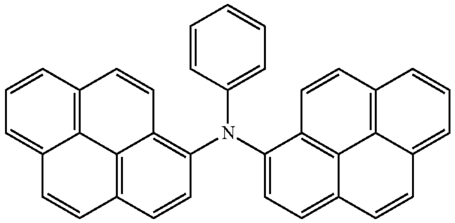

-continued
P2
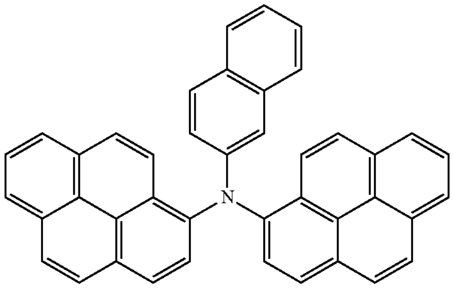
P3
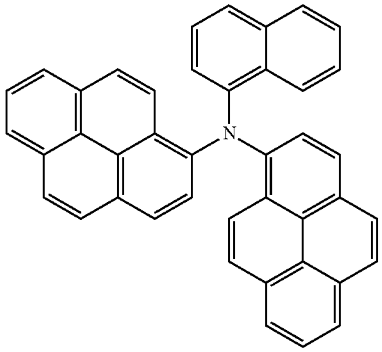
P4
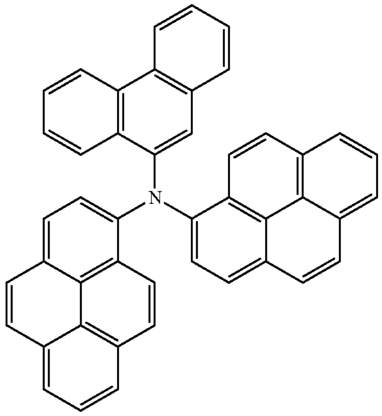
P5
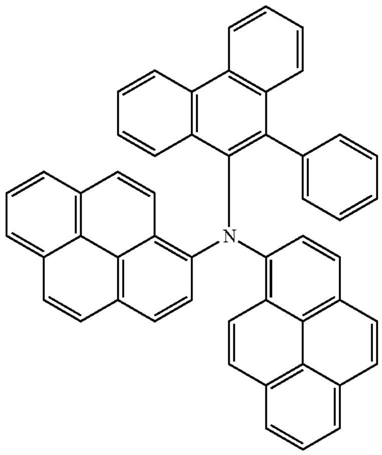
-continued
P6
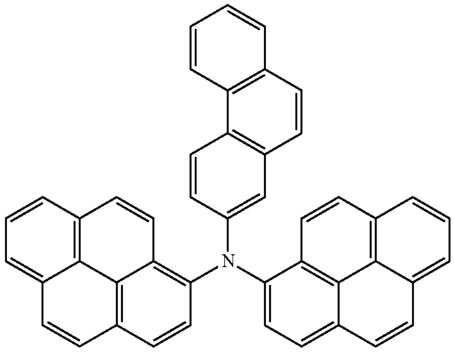
P7
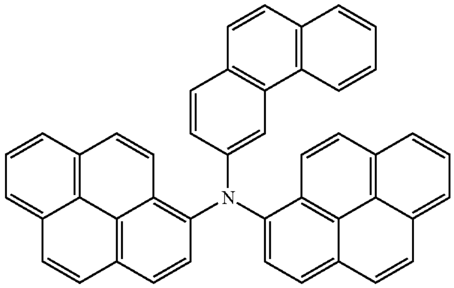
P8
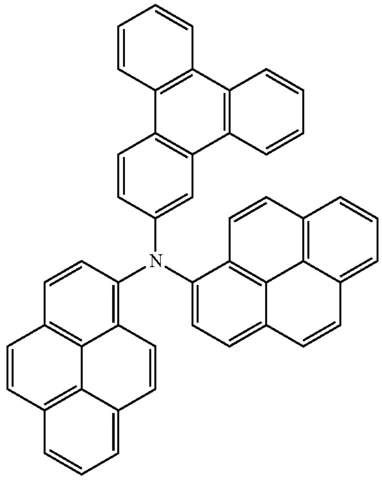
P9
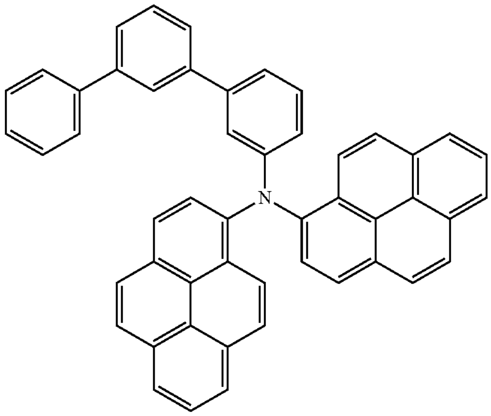

-continued
P10
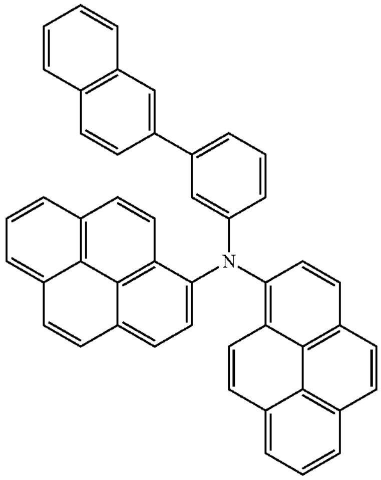
P11
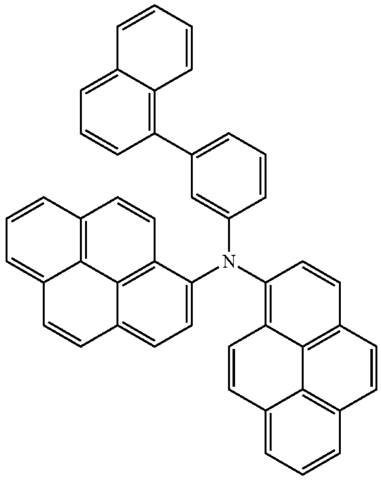
P12
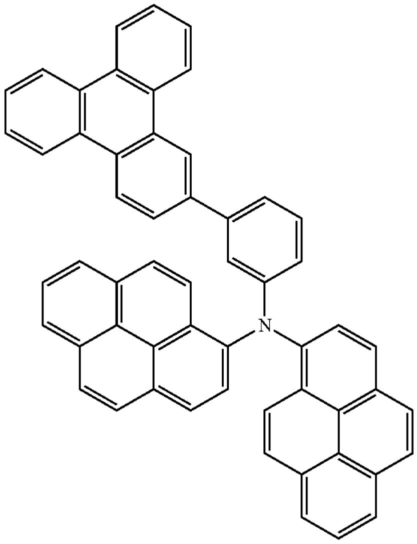
-continued
P13
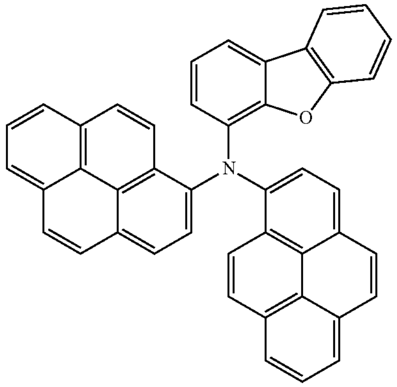
P14
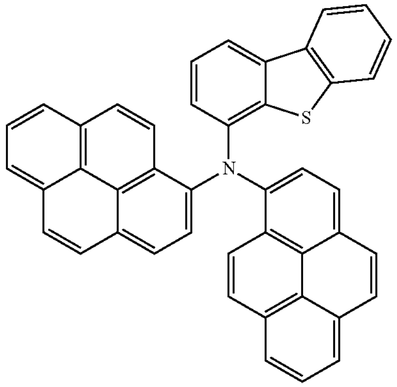
P15
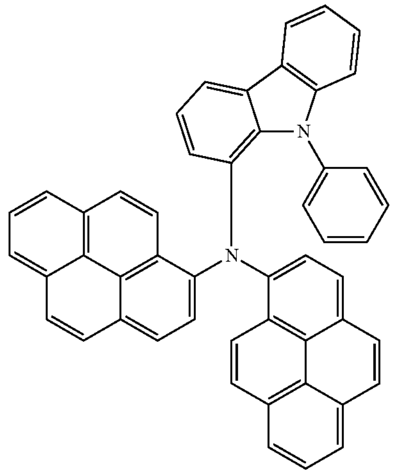
[C8]
P16
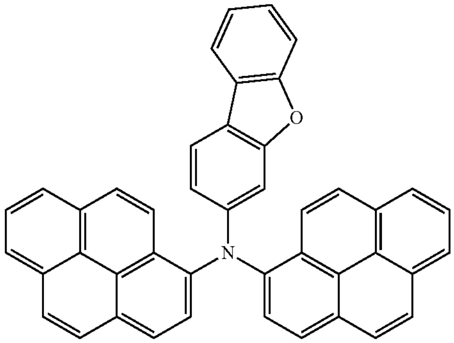

-continued
P17
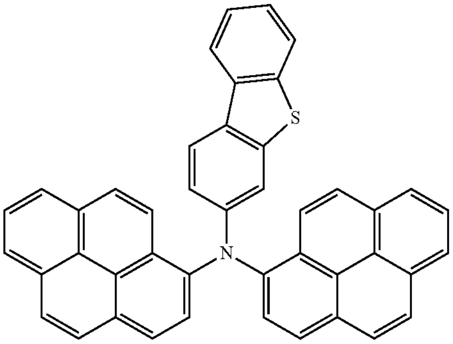
P18
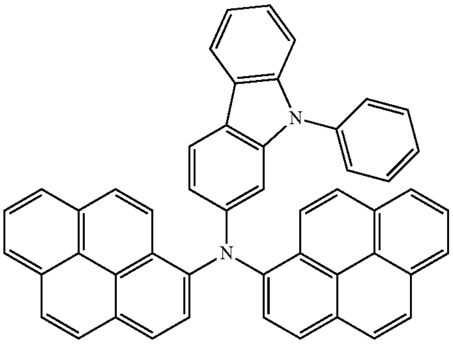
P19
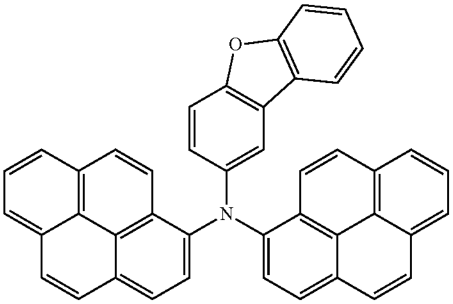
P20
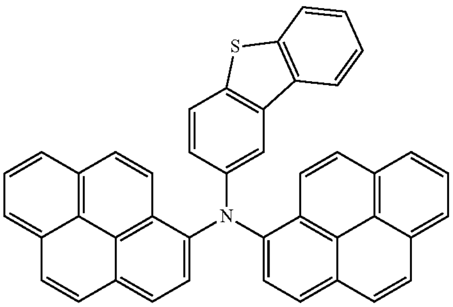
-continued
P21
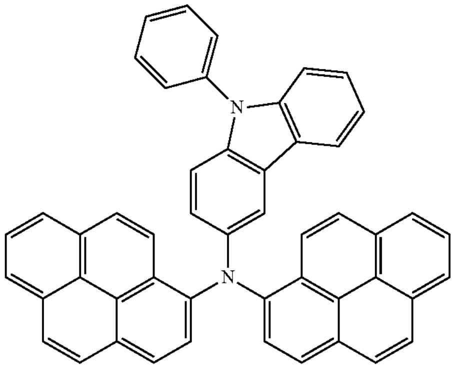
P22
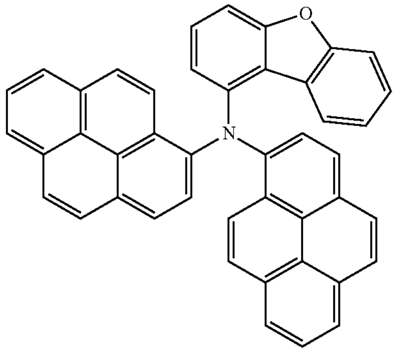
P23
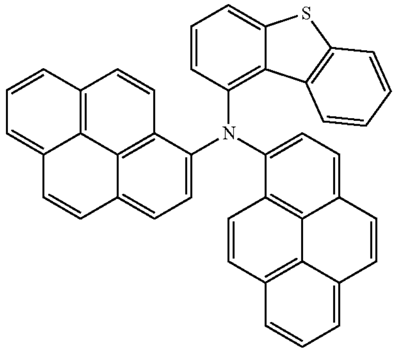
P24
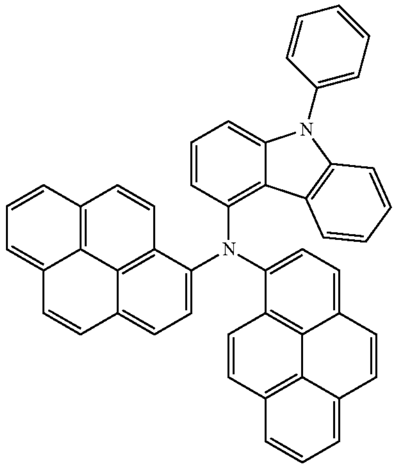

-continued
P25
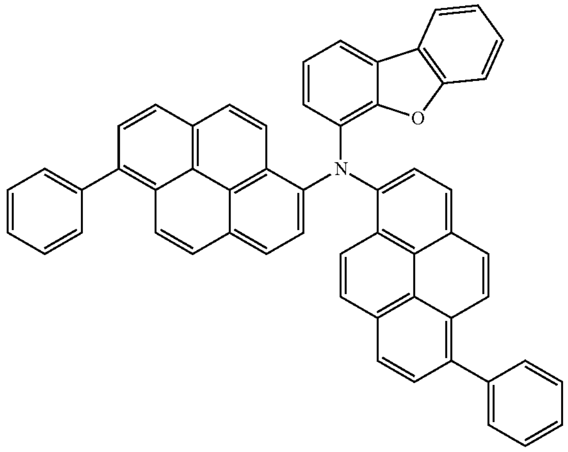
P26
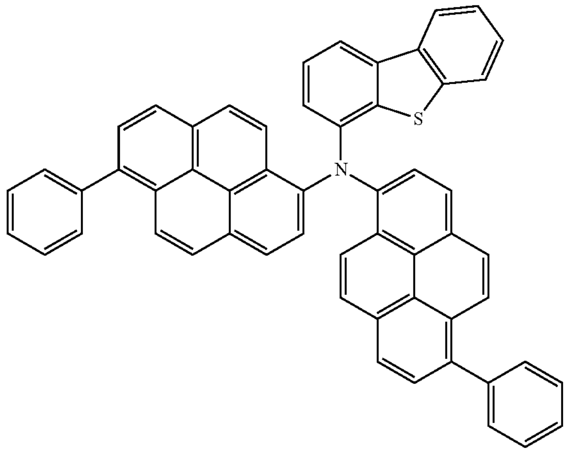
P27
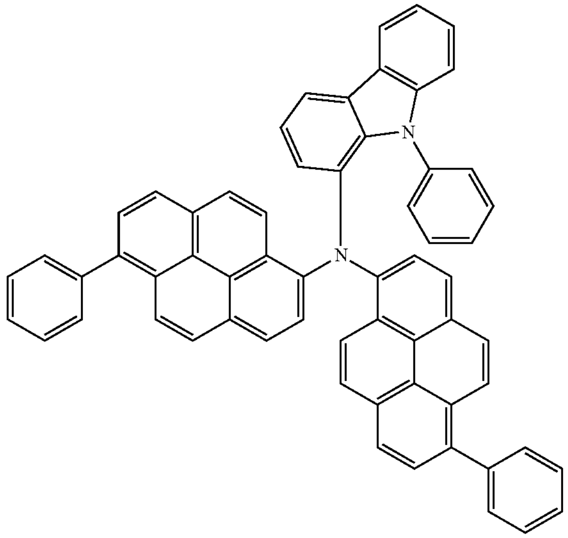
-continued
P28
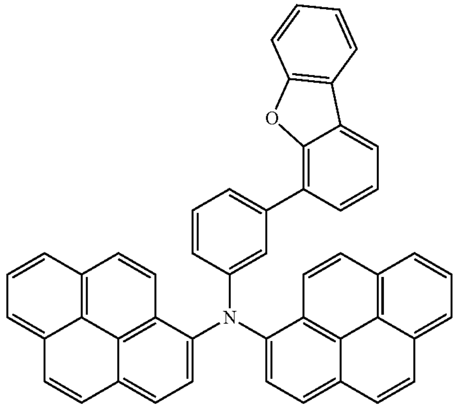
P29
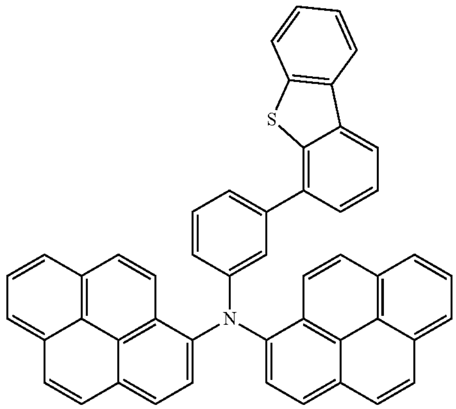
P30
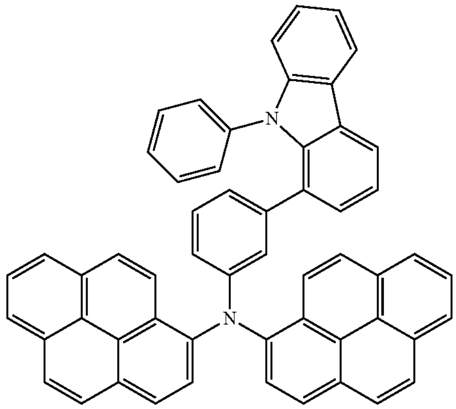
P31
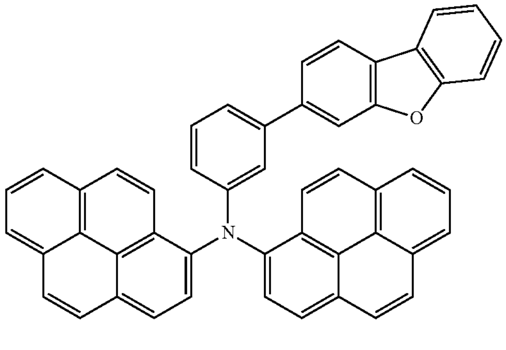

-continued
P32
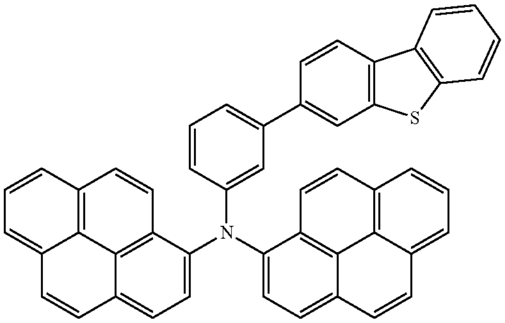
P33
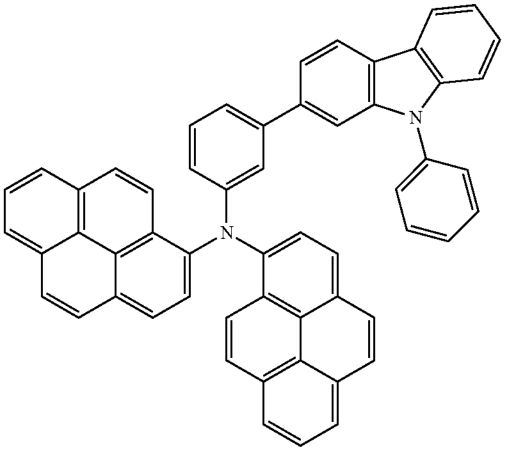
[C9]
P34
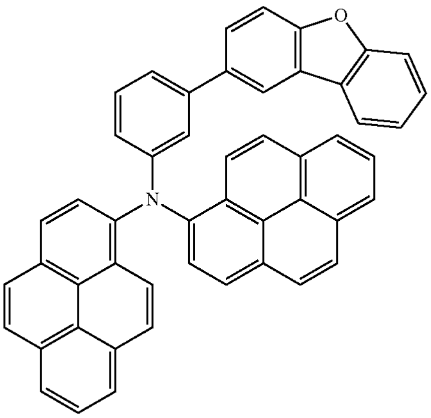
P35
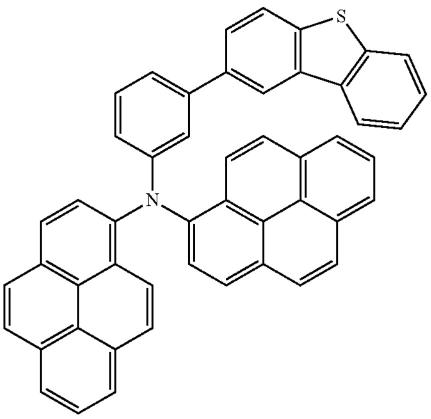
-continued
P36
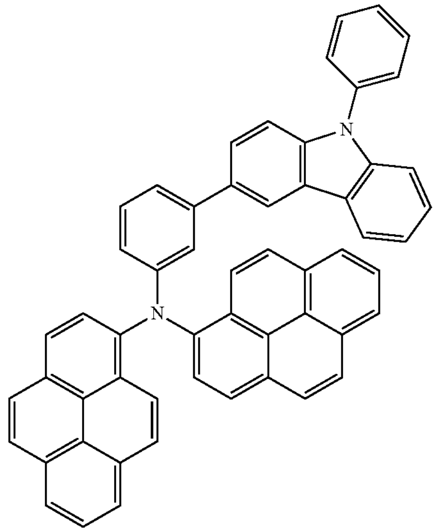
P37
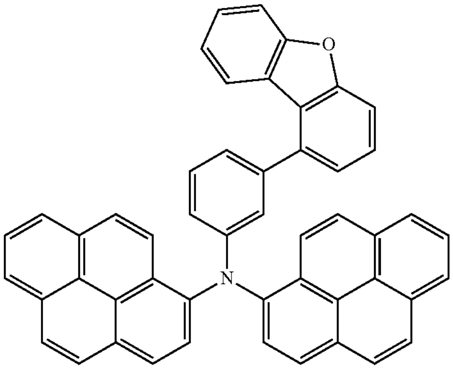
P38
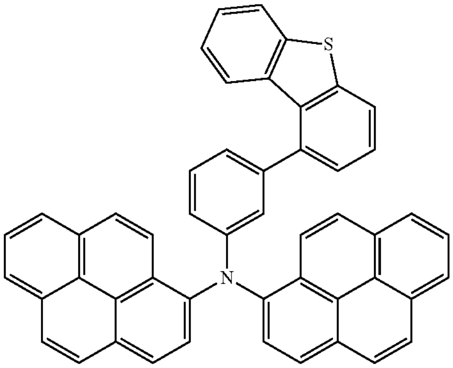

-continued
P39
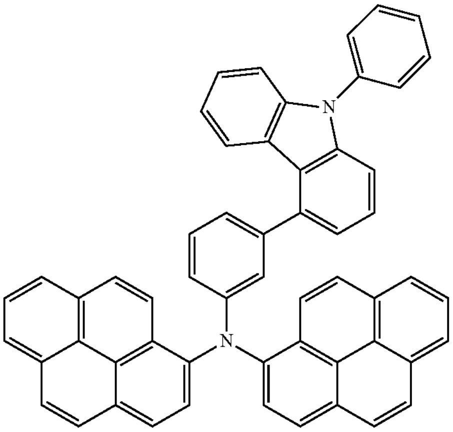
P40
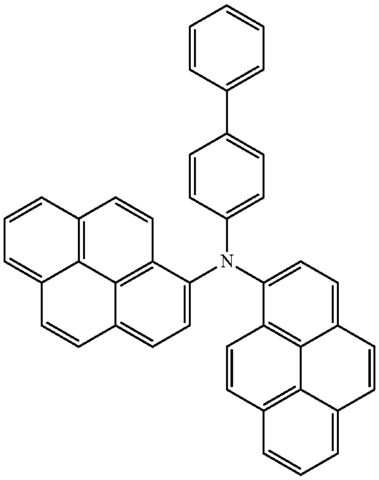
P41
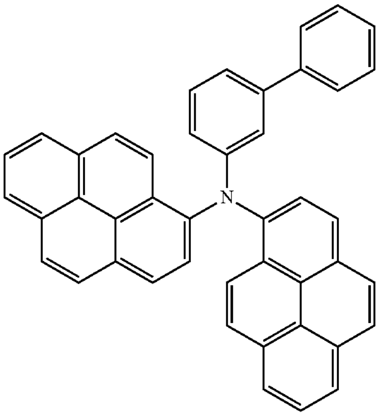
-continued
P42
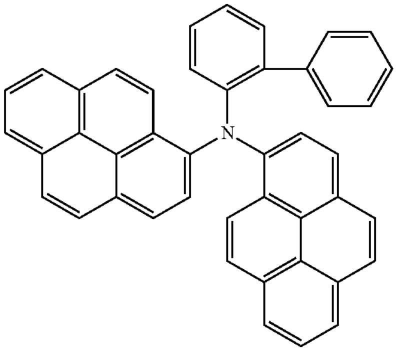
P43
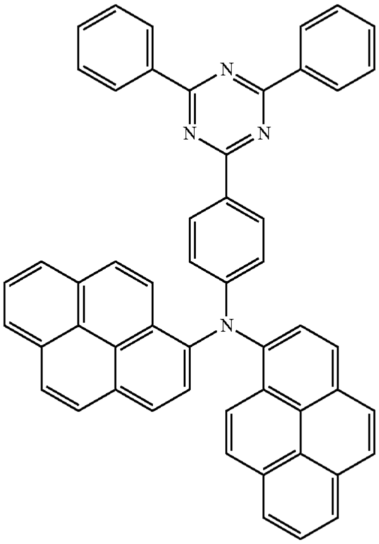
P44
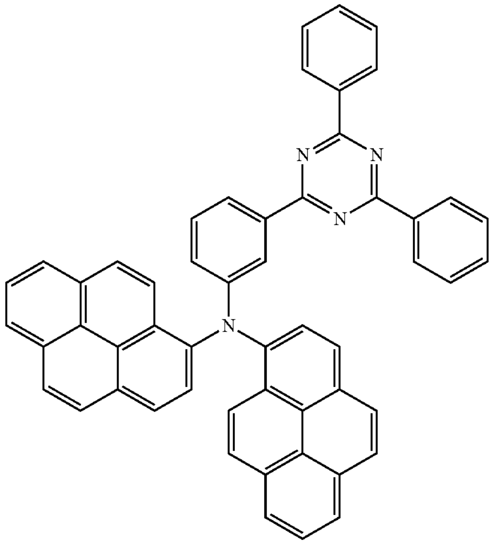

-continued
P45
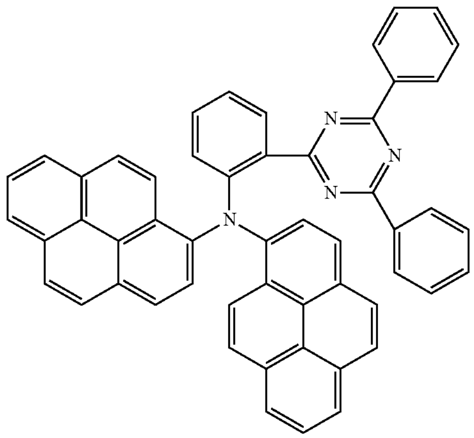
P46
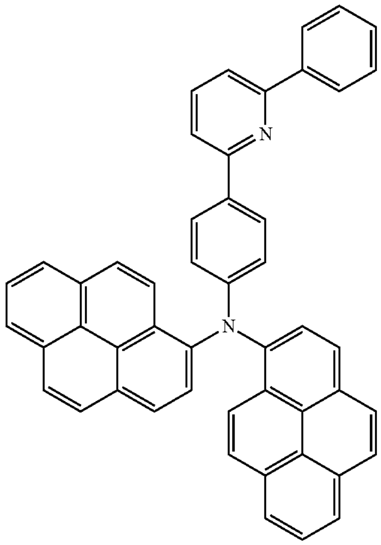
P47
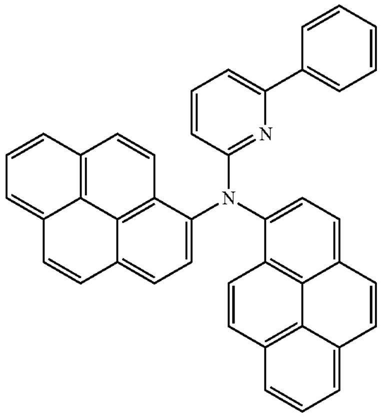
-continued
P48
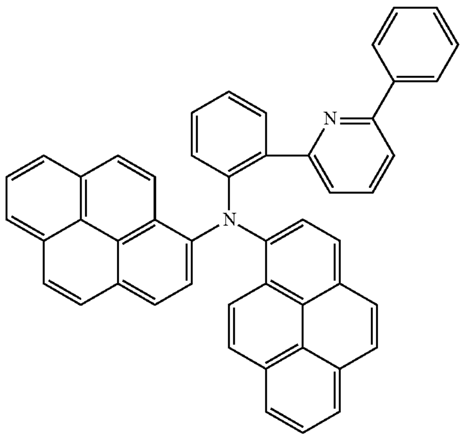
[C10]
P49
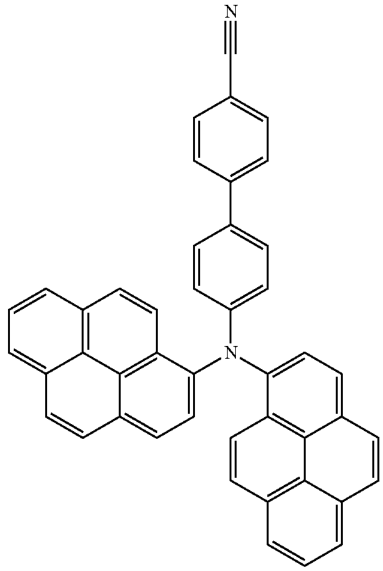
P50
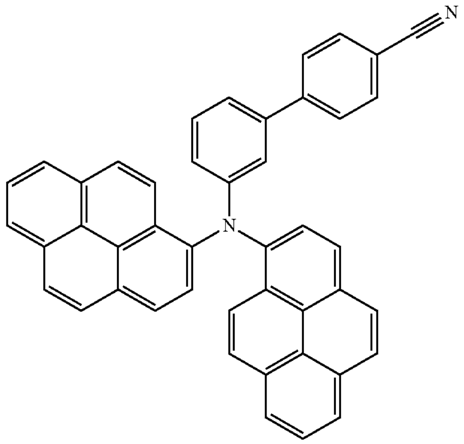

-continued
P51
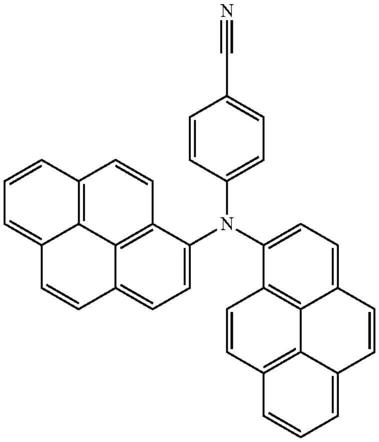
P52
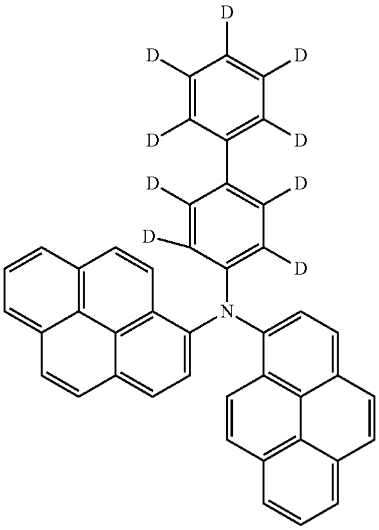
P53
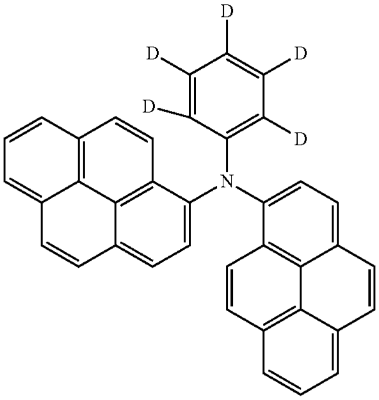
-continued
P54
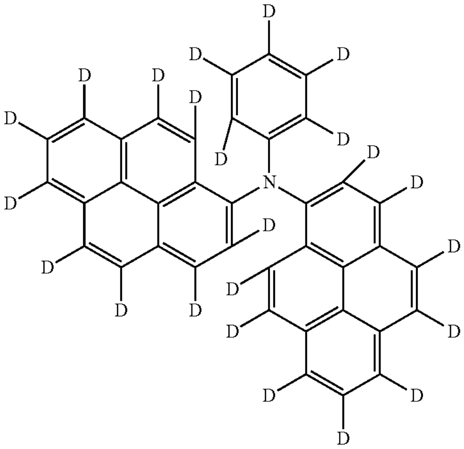
P55
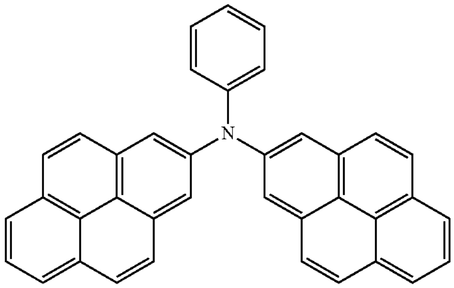
P56
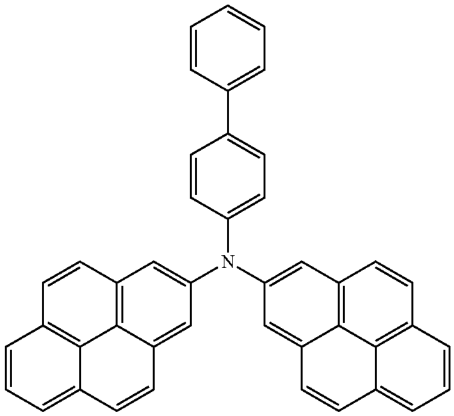
P57
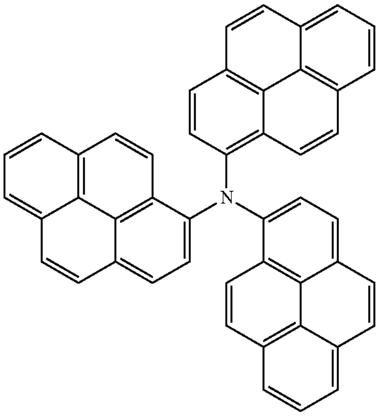

-continued
P58
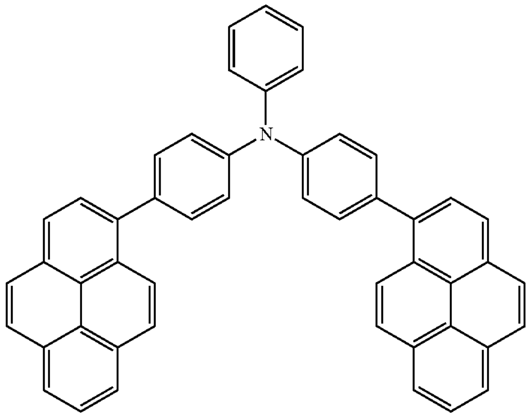
P59
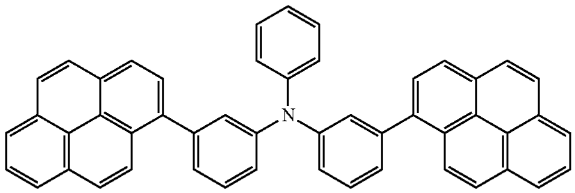
P60
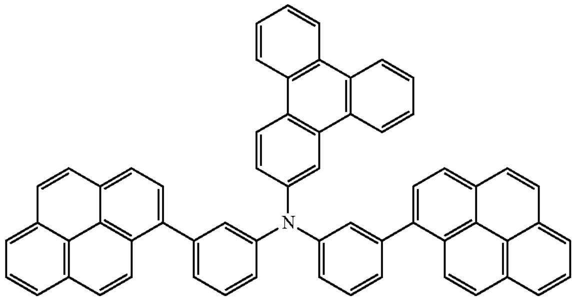
P61
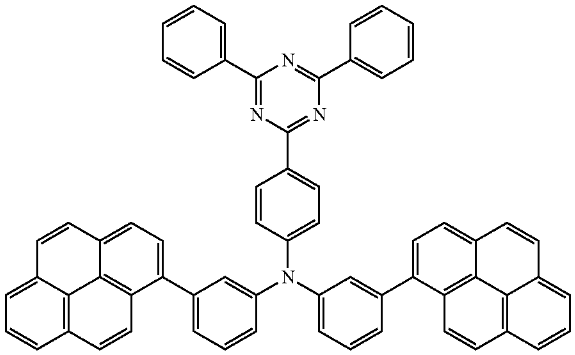
-continued
P62
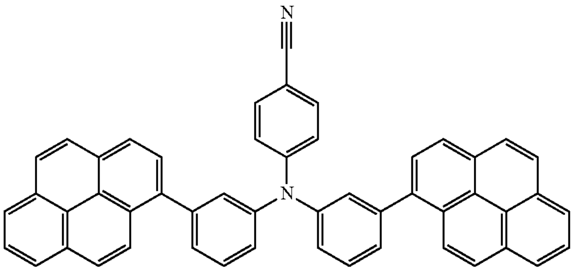
P63
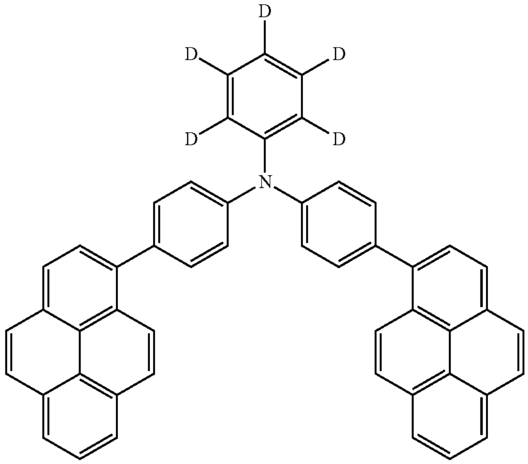
P64
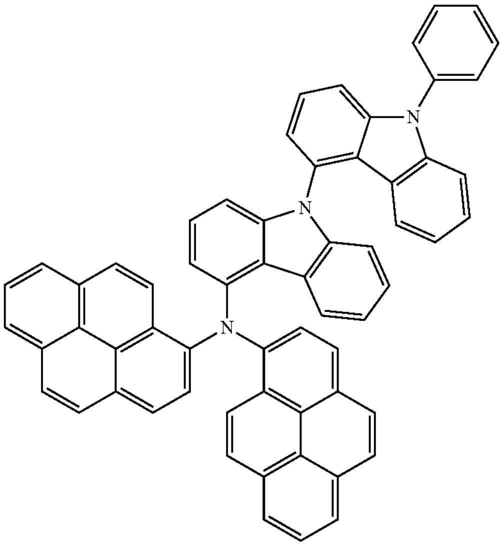

-continued
P65
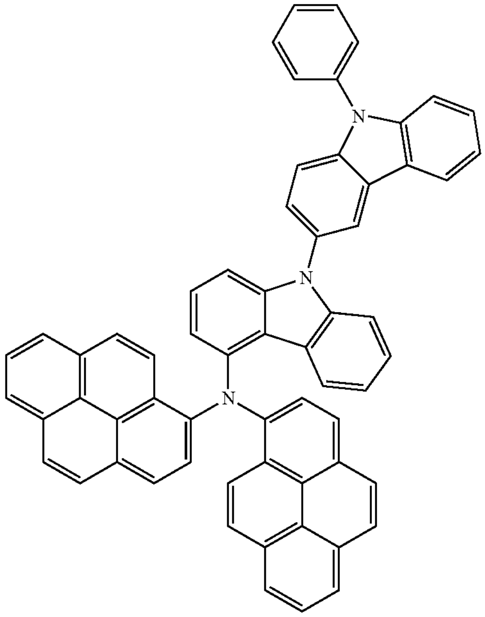
P66
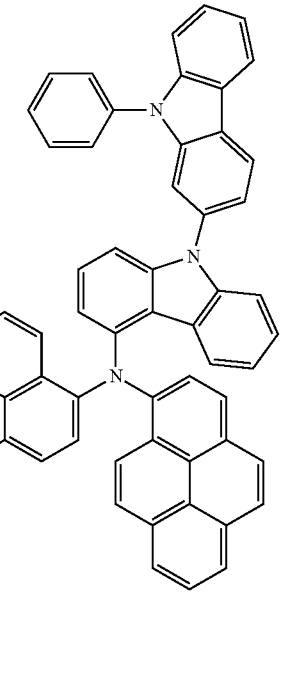
-continued
P67
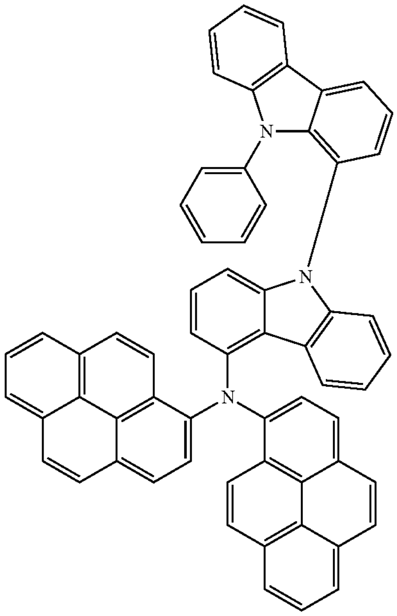
P68
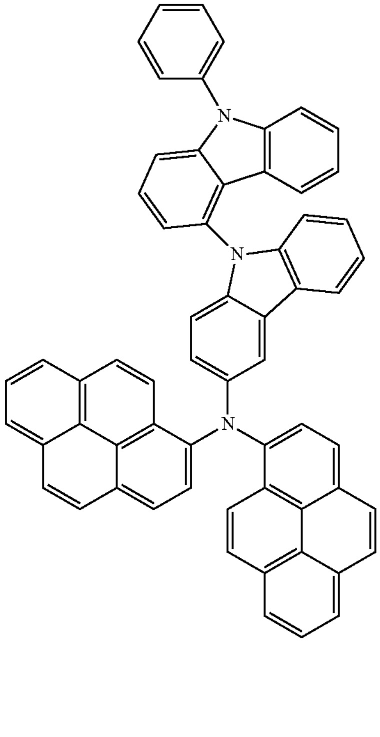

-continued
P69
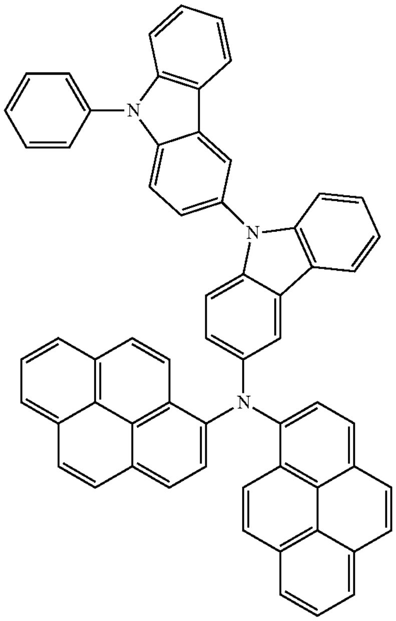
P70
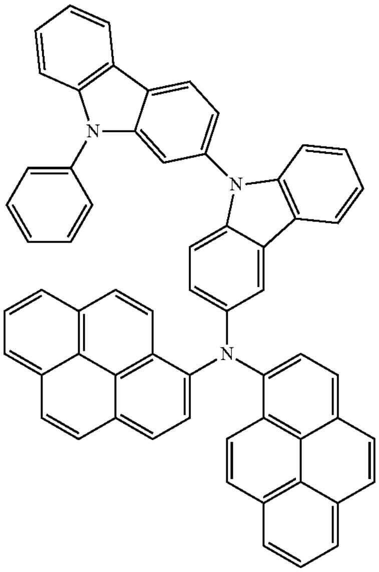
-continued
P71
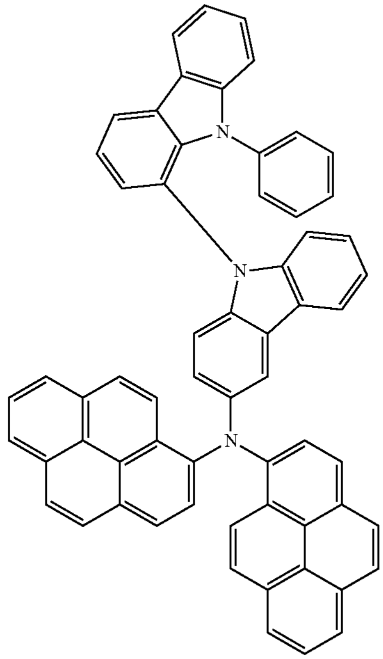
P72
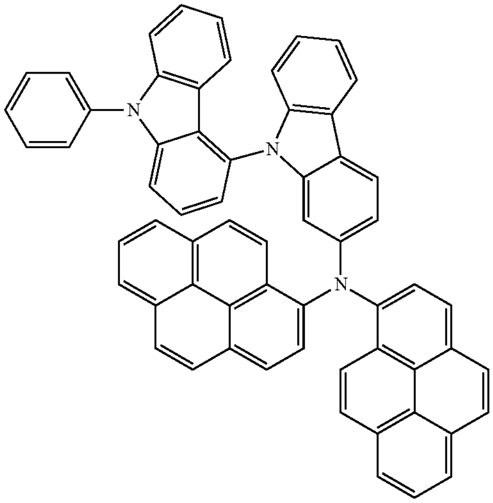
P73
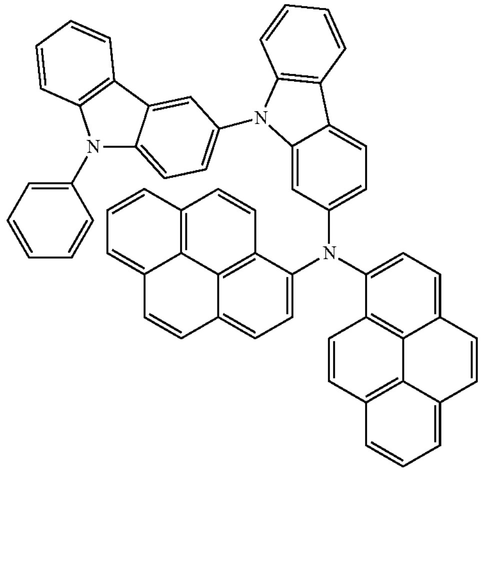

-continued
P74
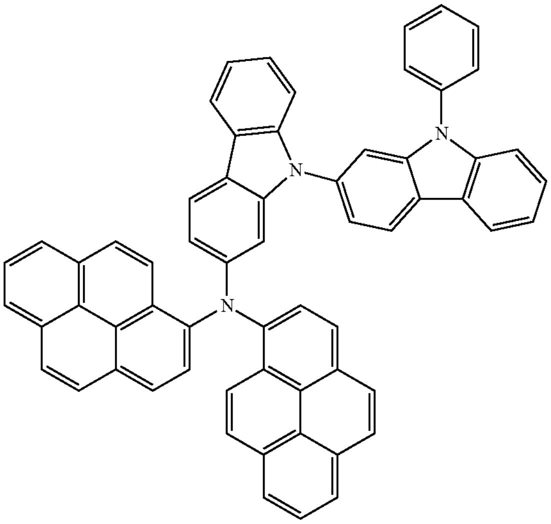
P75
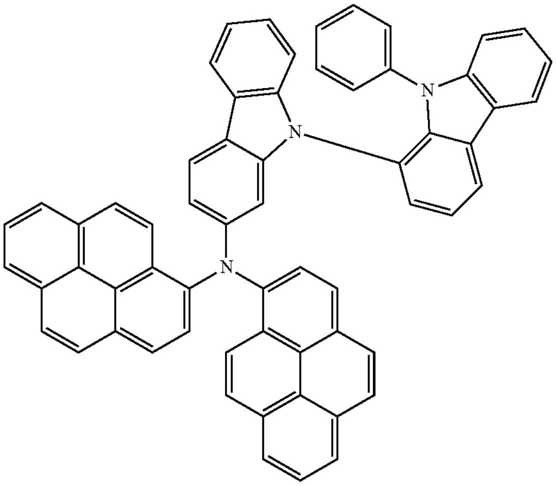
P76
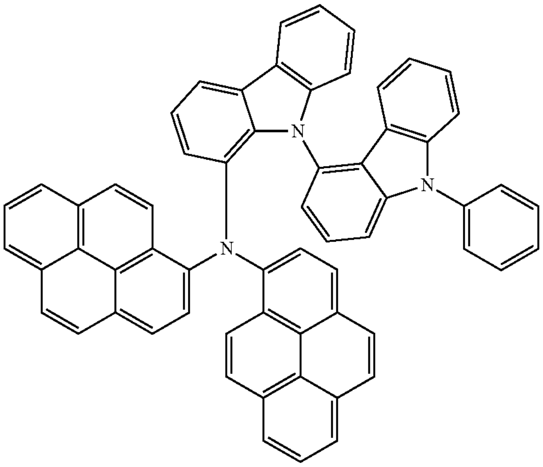
-continued
P77
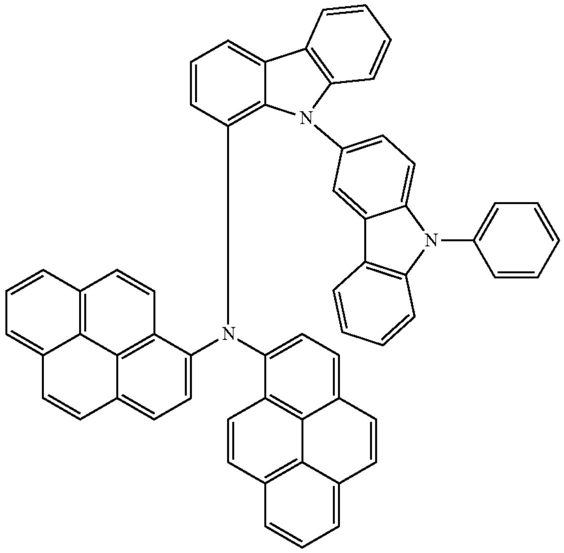
P78
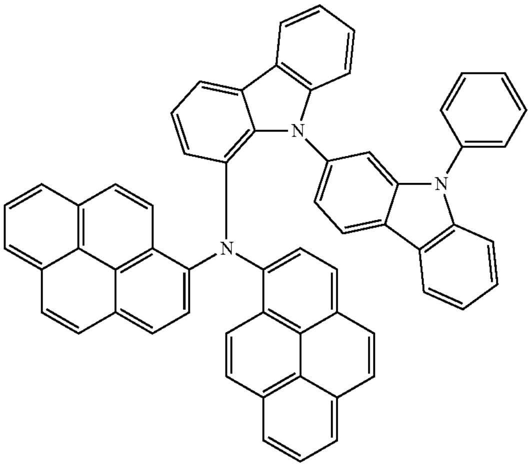
P79
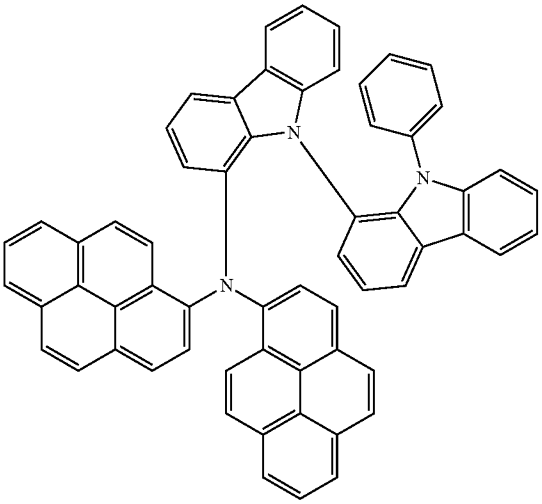

-continued
[C11]
D1
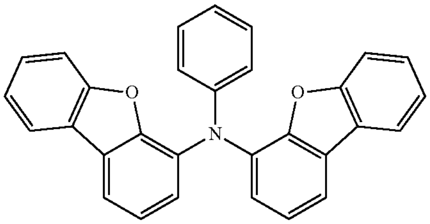
D2
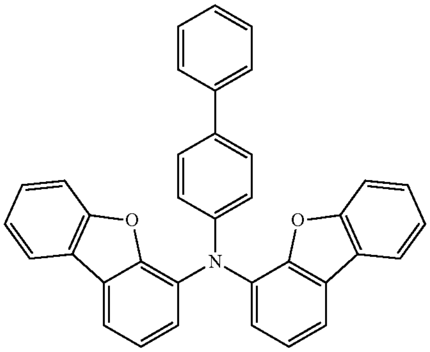
D3
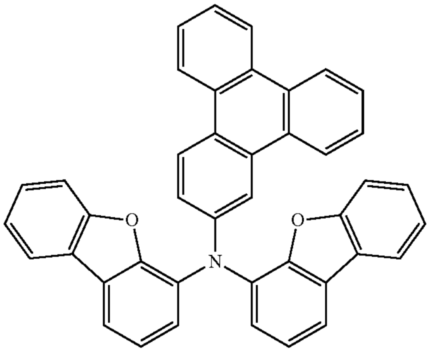
D4
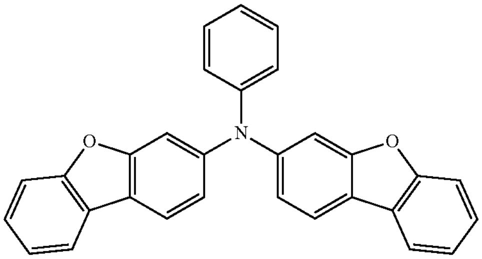
D5
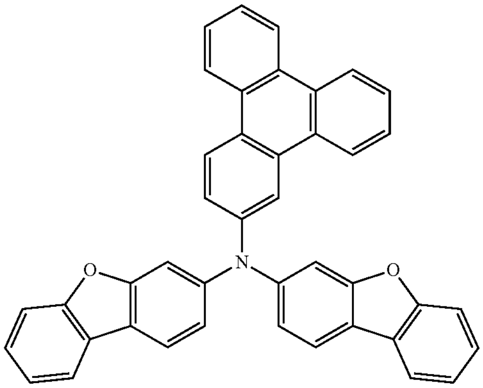
-continued
D6
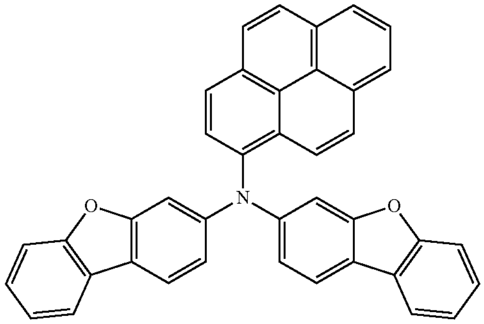
D7
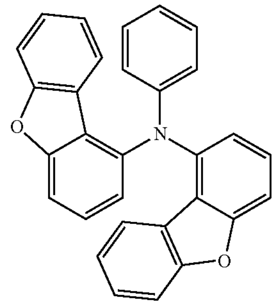
D8
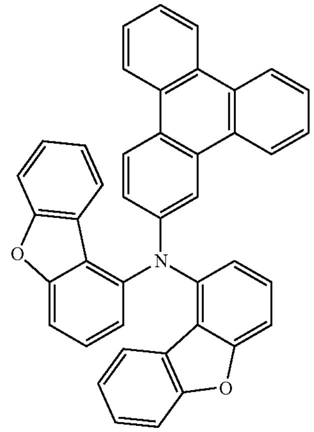
D9
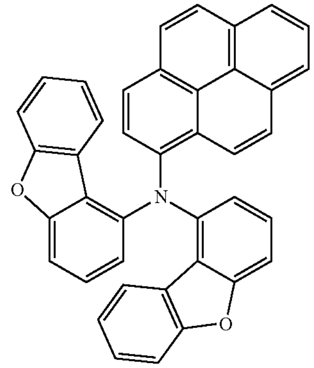

-continued
D10
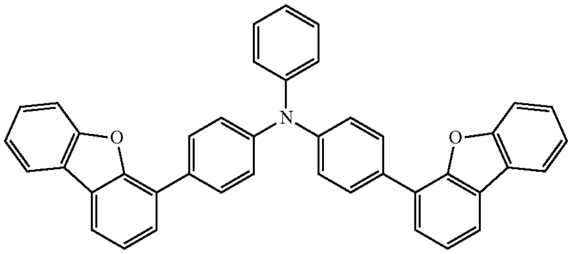
D11
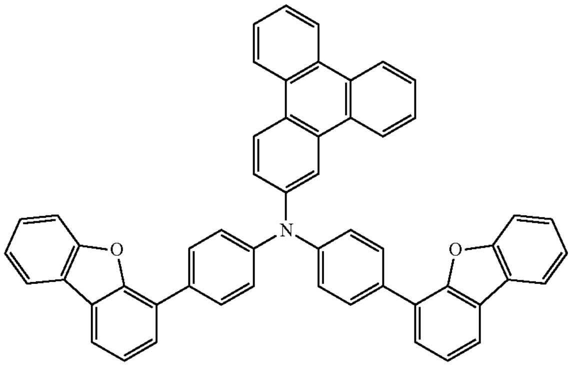
D12
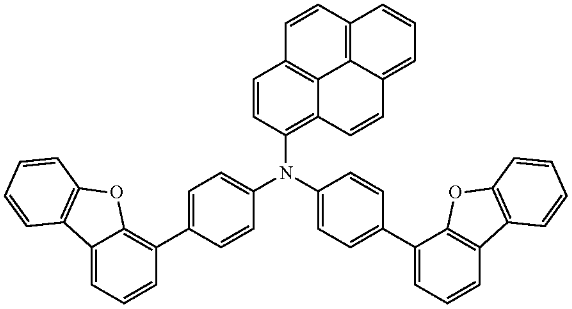
D13
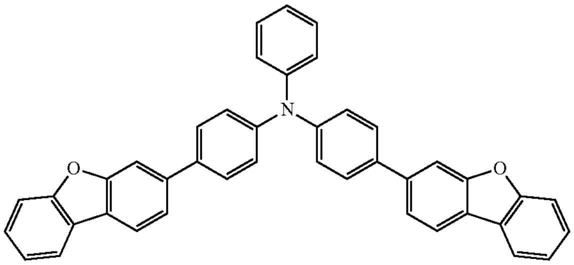
-continued
D14
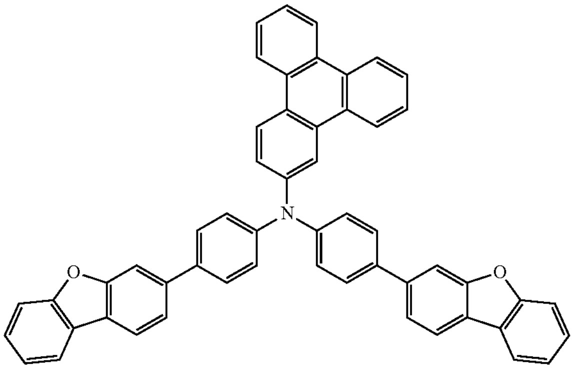
D15
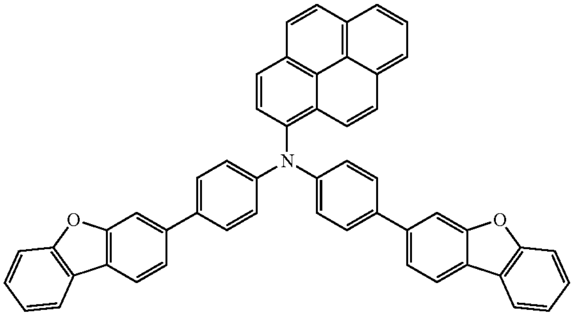
D16
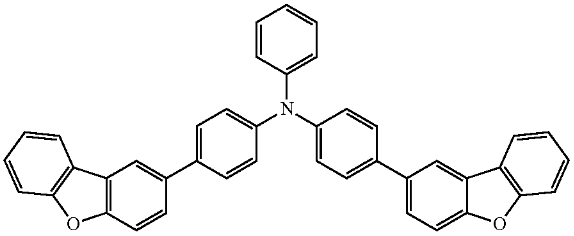
D17
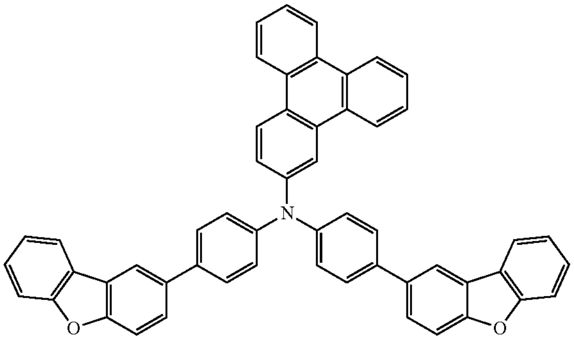

-continued
D18
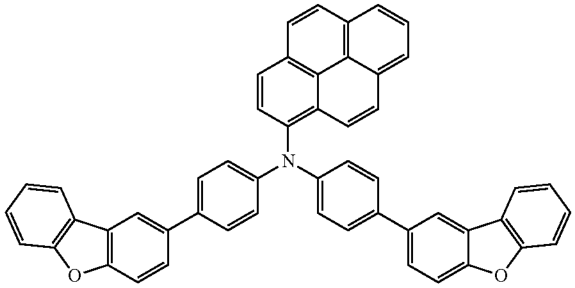
D19
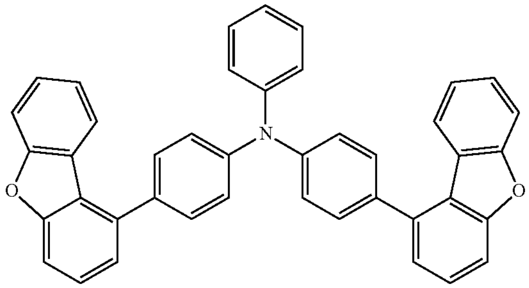
D20
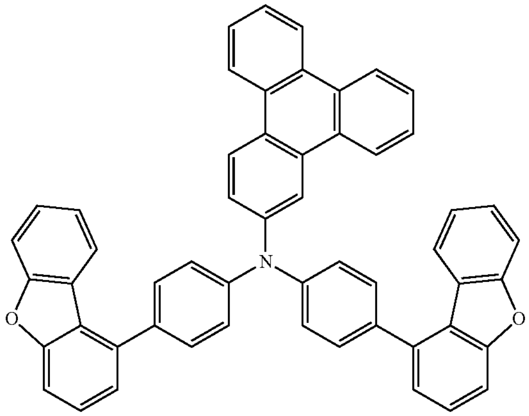
D21
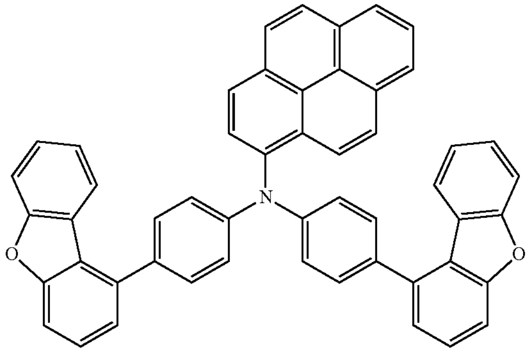
[C12]
D22
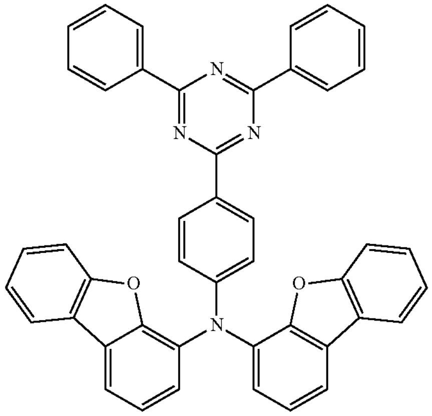
D23
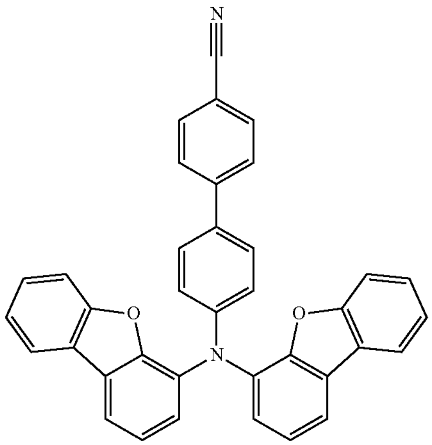
D24
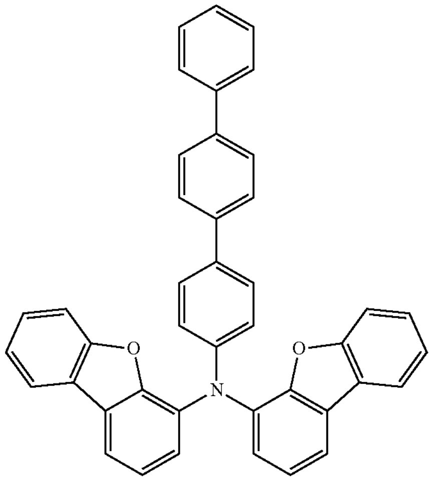
D25
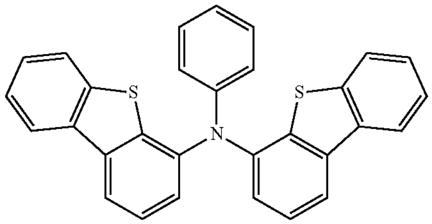

D26
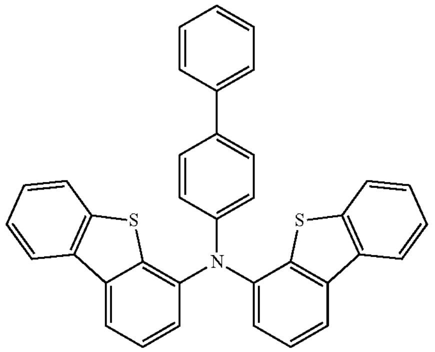
D27
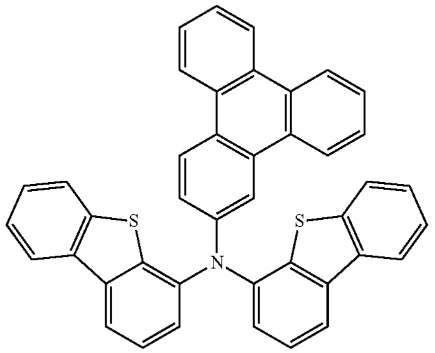
D28
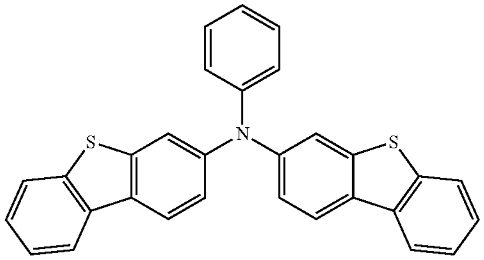
D29
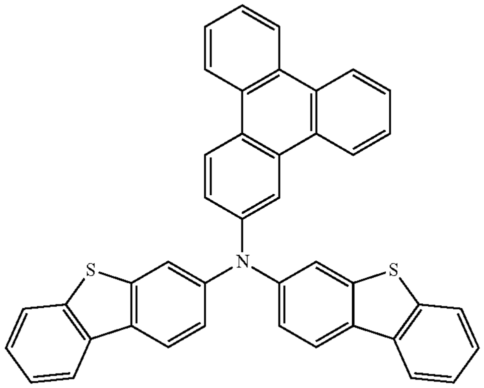
D30
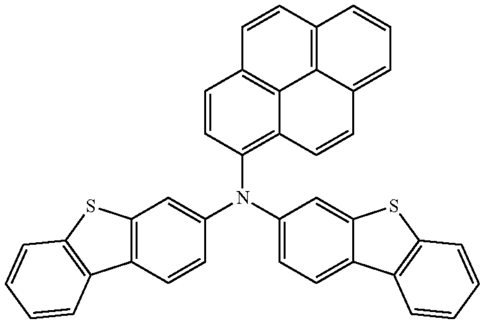
D31
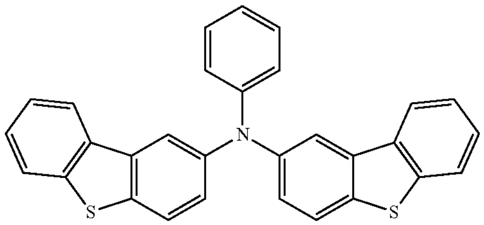
D32
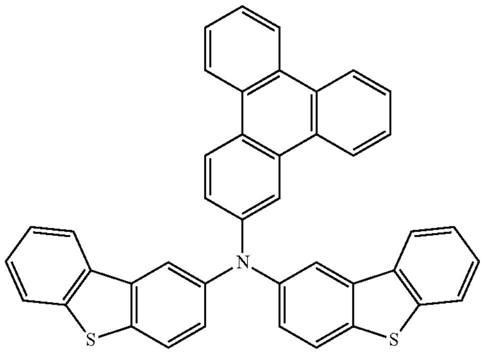
D33
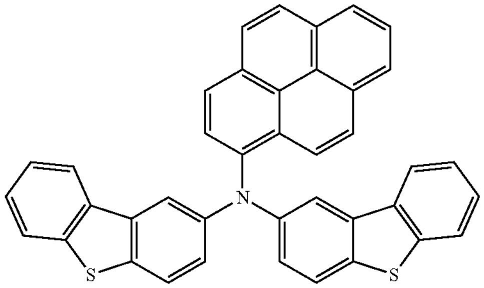
D34
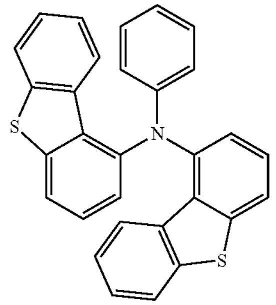

-continued
D35
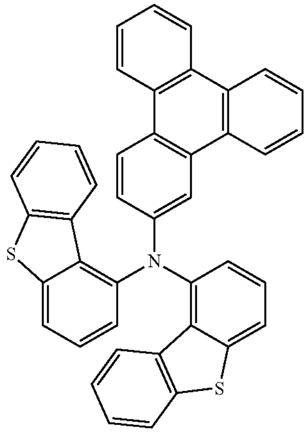
D36
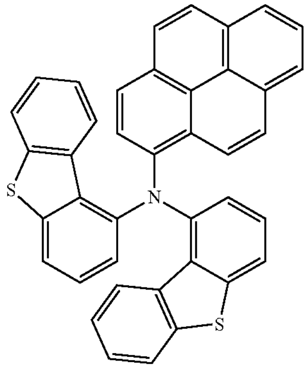
D37
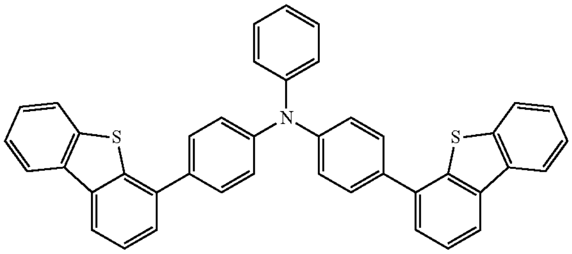
D38
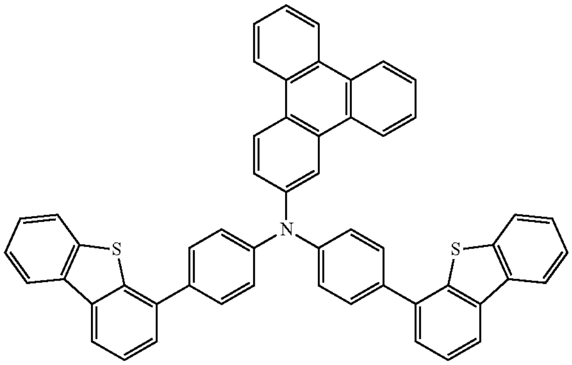
-continued
D39
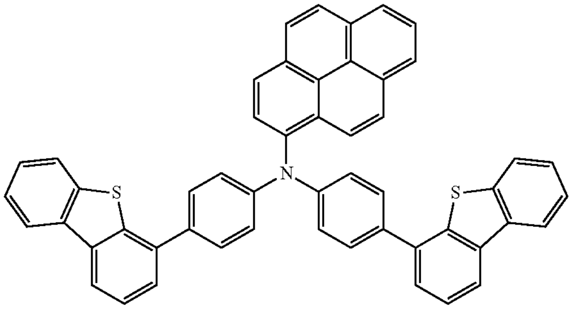
[C13]
D40
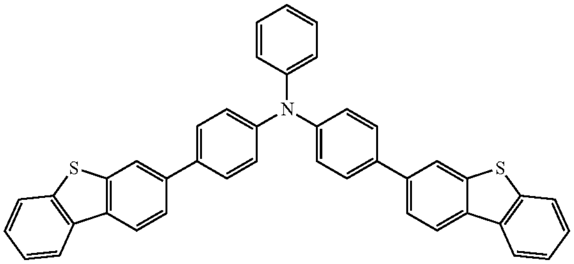
D41
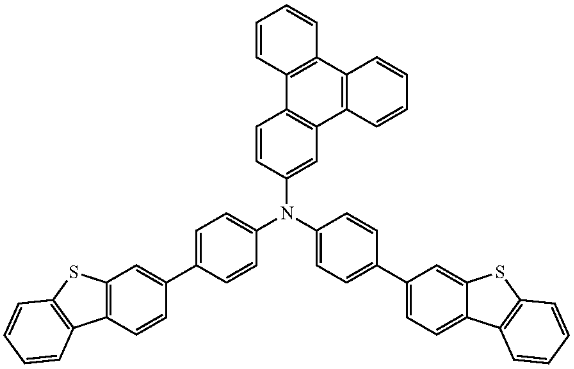
D42
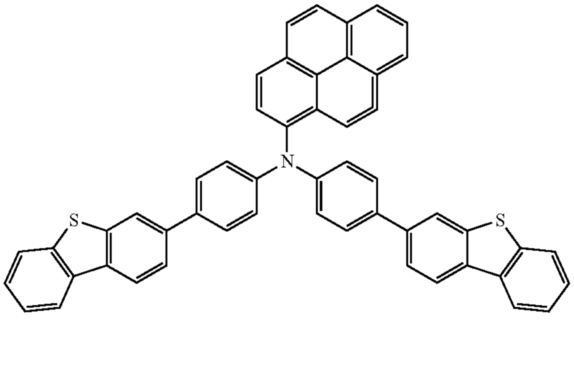

-continued
D43
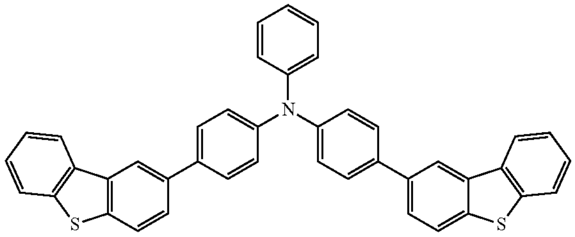
D44
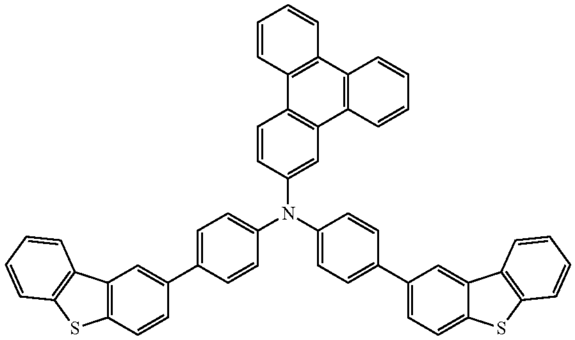
D45
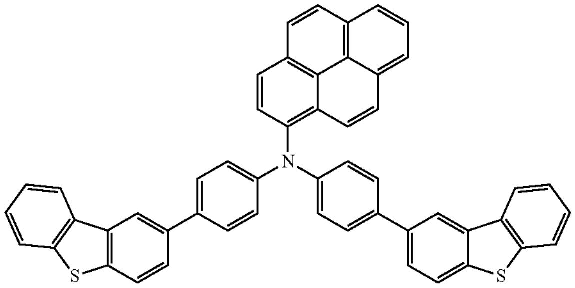
D46
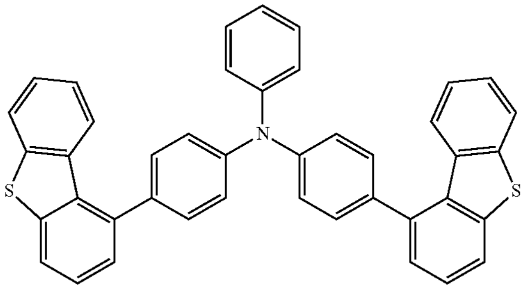
-continued
D47
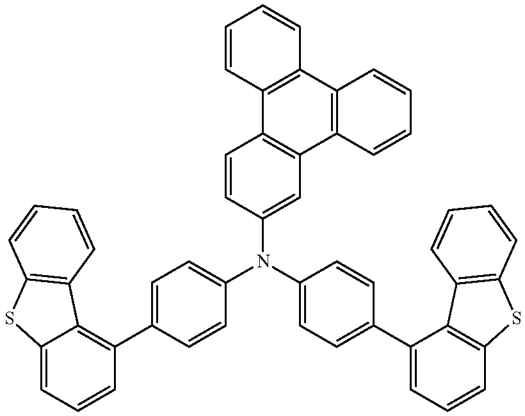
D48
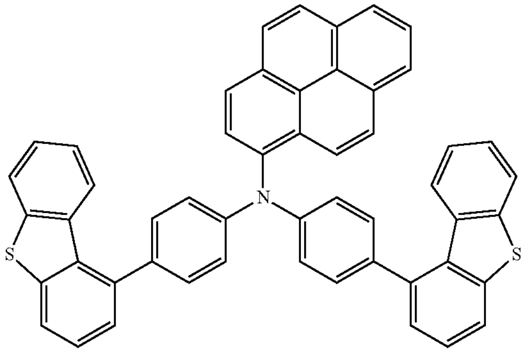
D49
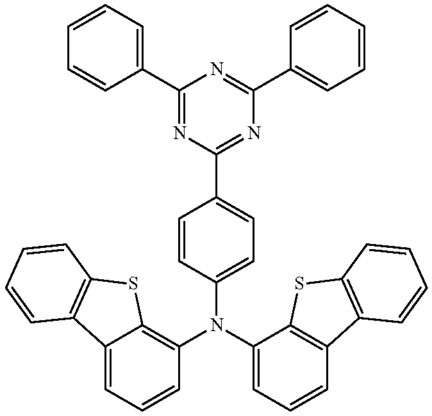

-continued
D50
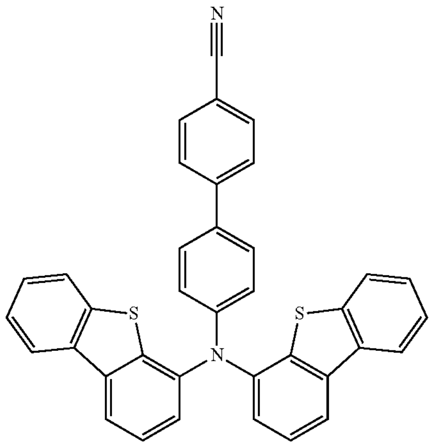
D51
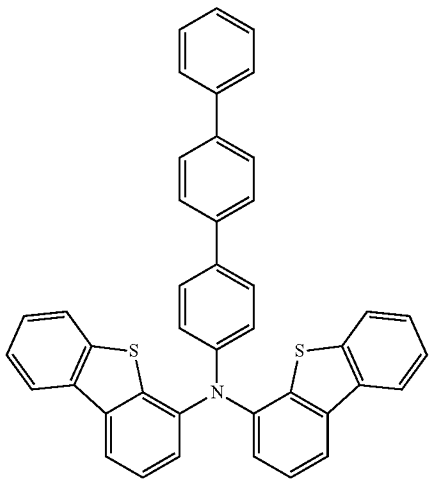
M1
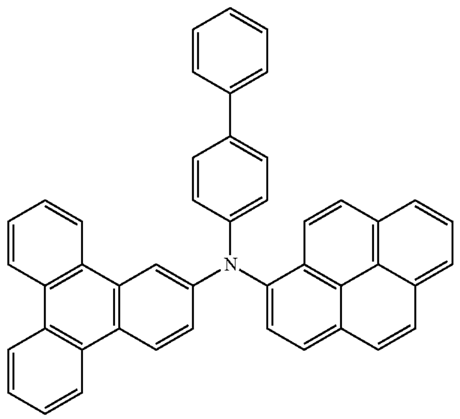
-continued
M2
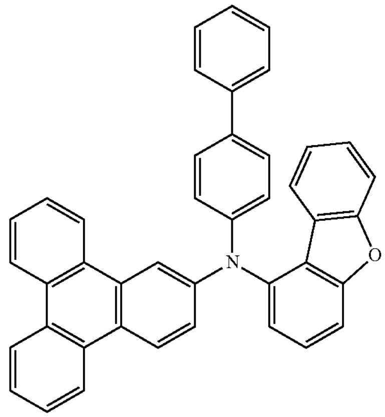
M3
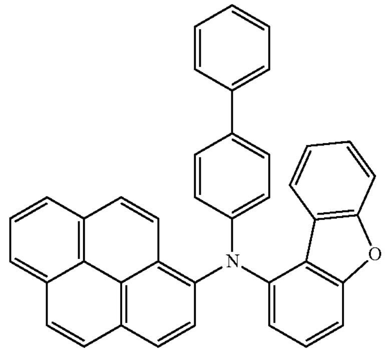
M4
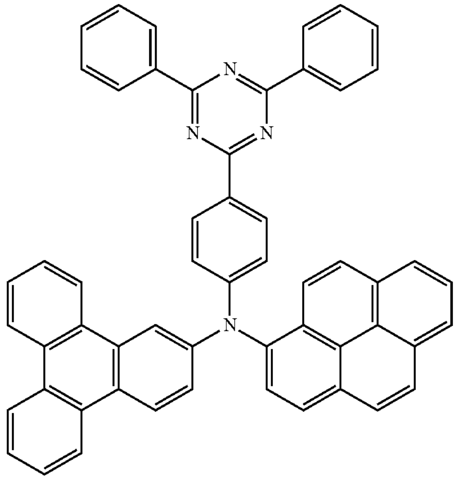

-continued
M5
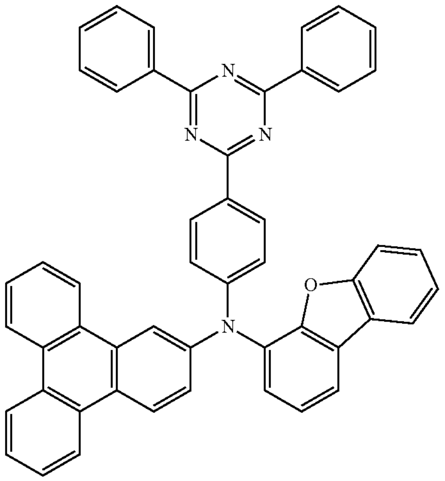
M6
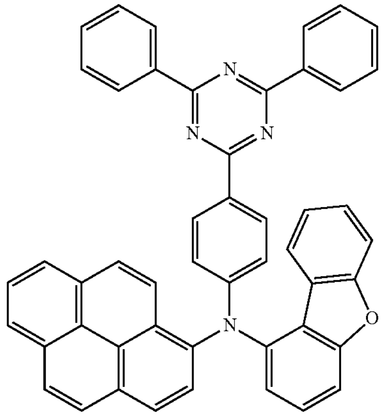
[C14]
M7
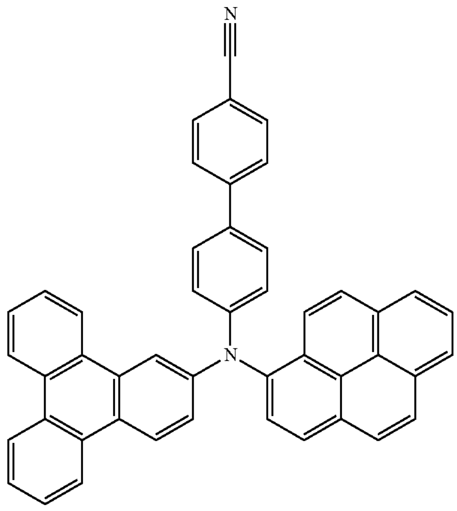
-continued
M8
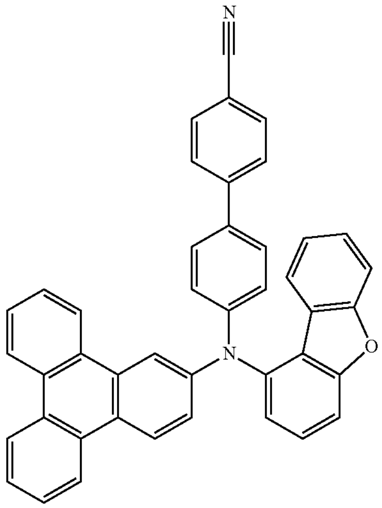
M9
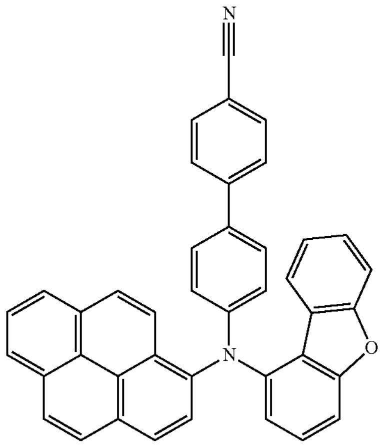
M10
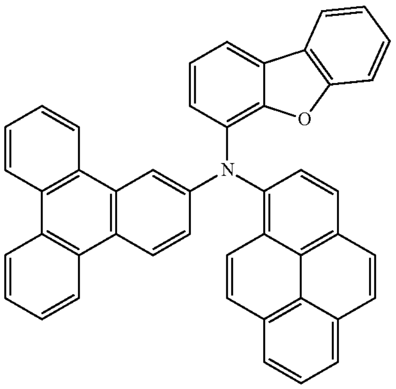

-continued
M11
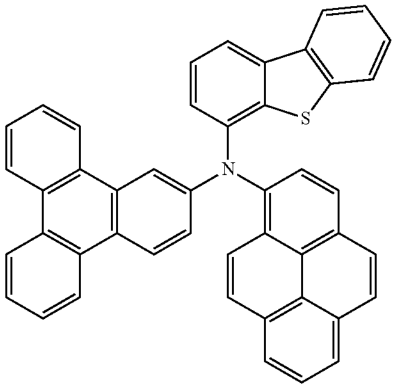
M12
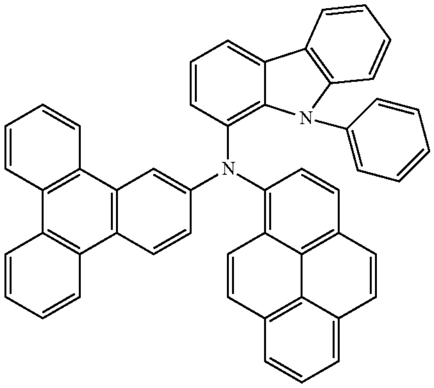
M13
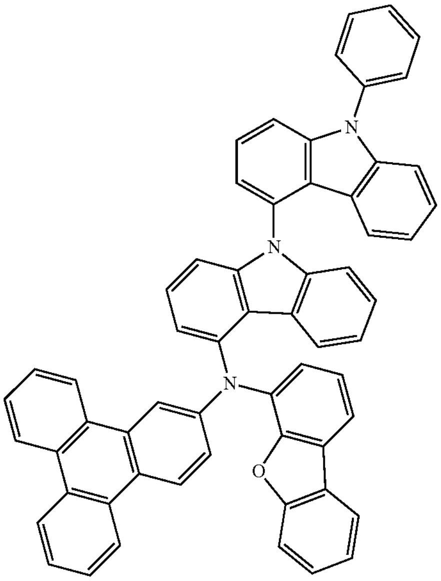
-continued
M14
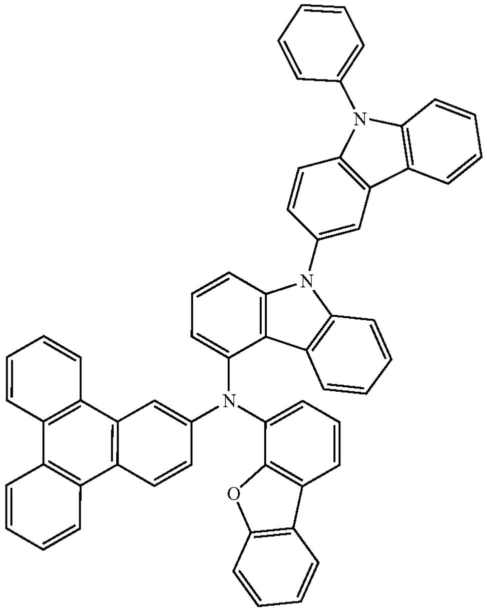
M15
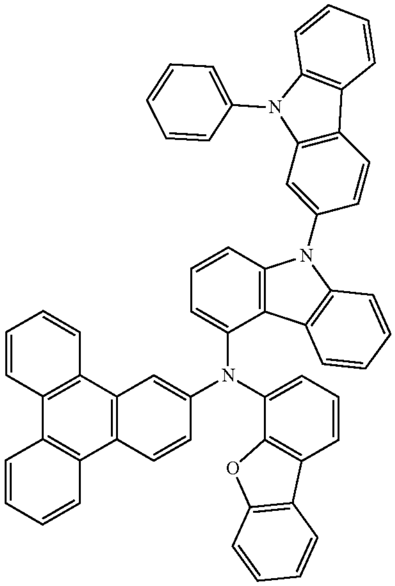

-continued
M16
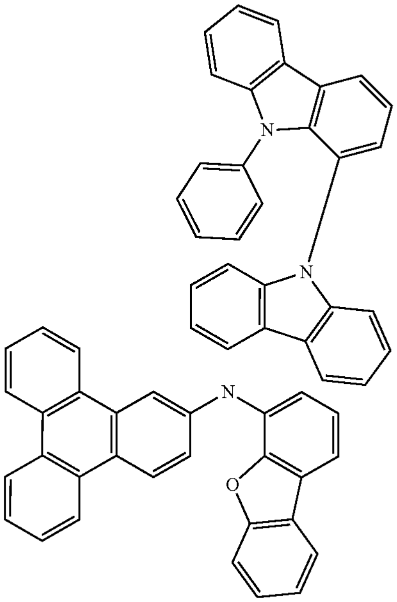
M17
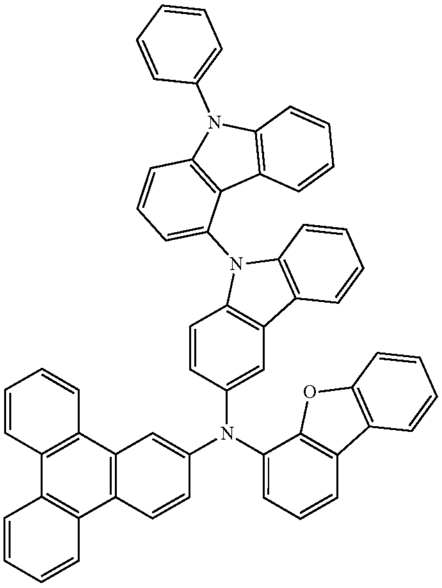
-continued
M18
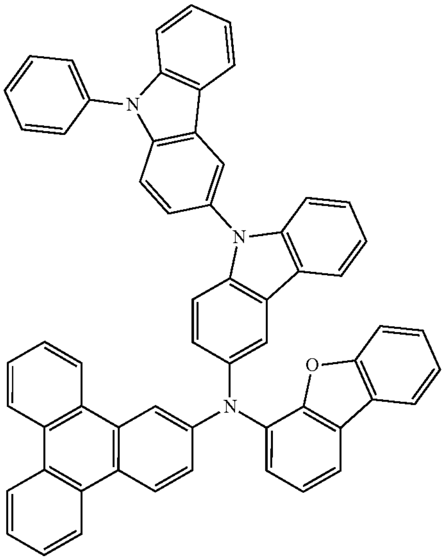
M19
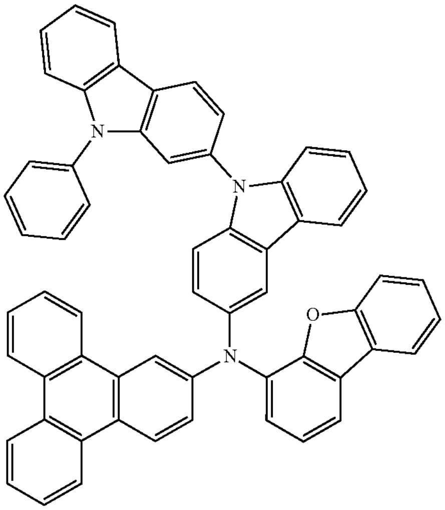
M20
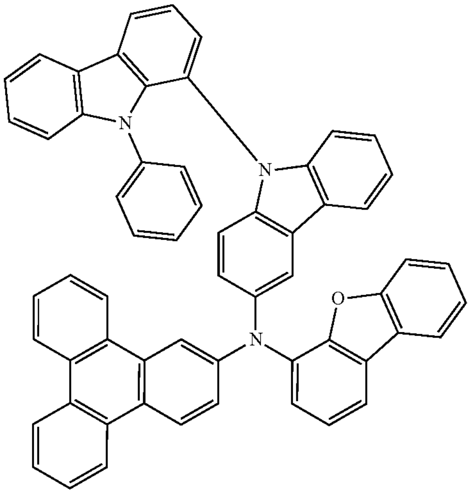

-continued
M21
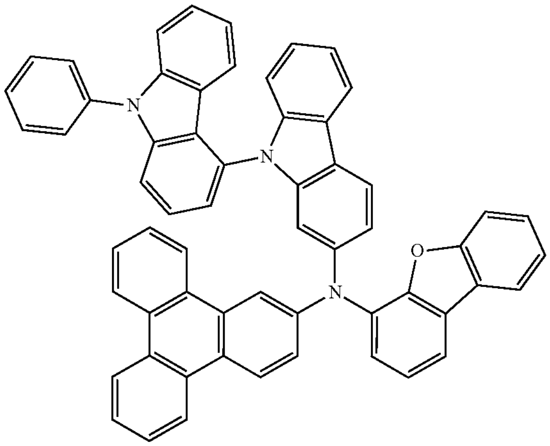
M22
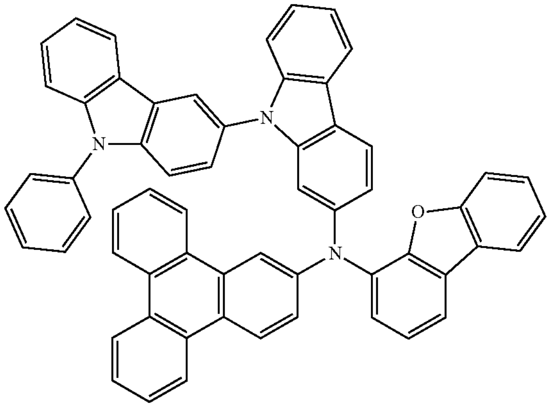
M23
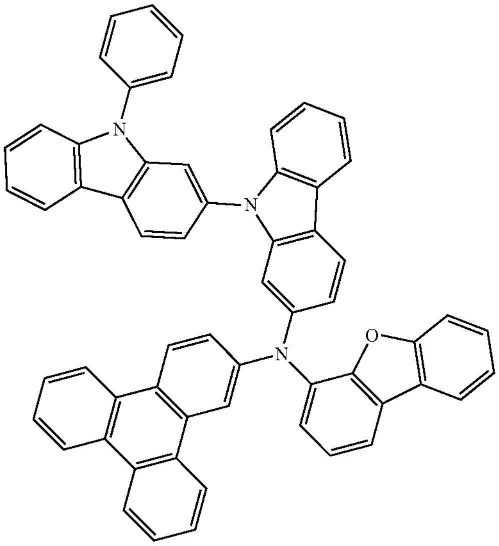
-continued
M24
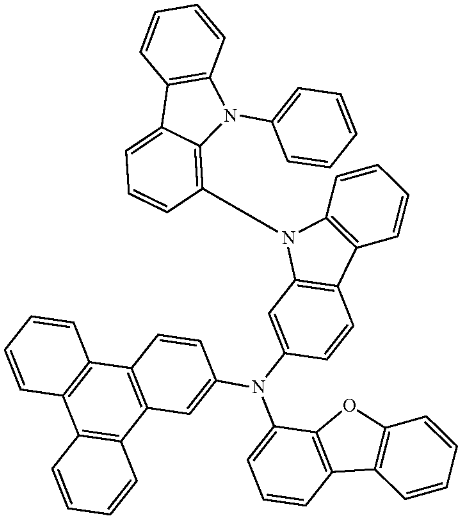
M25
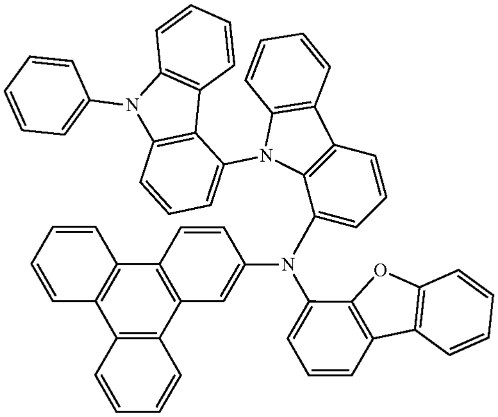
M26
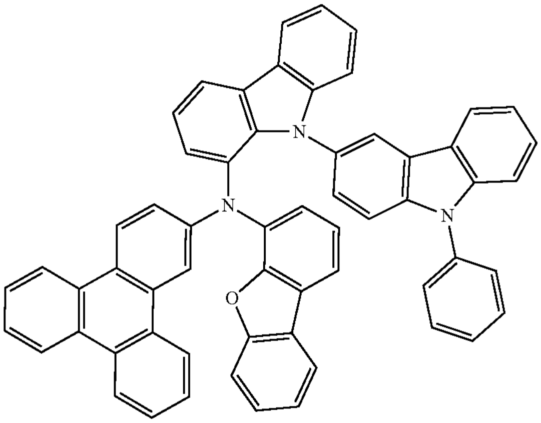

-continued
M27
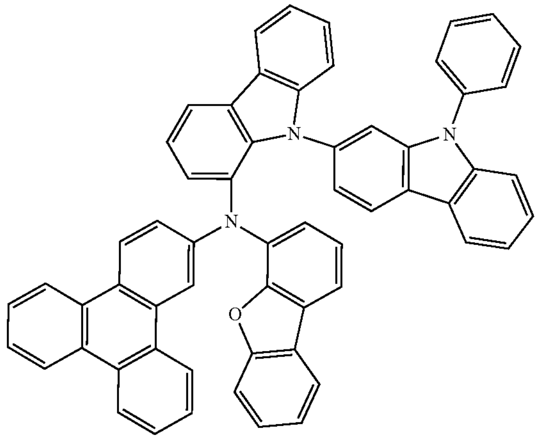
M28
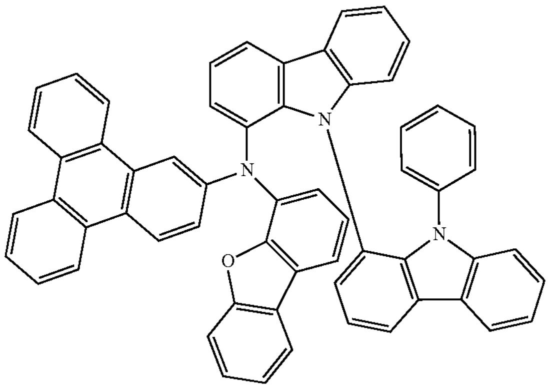
M29
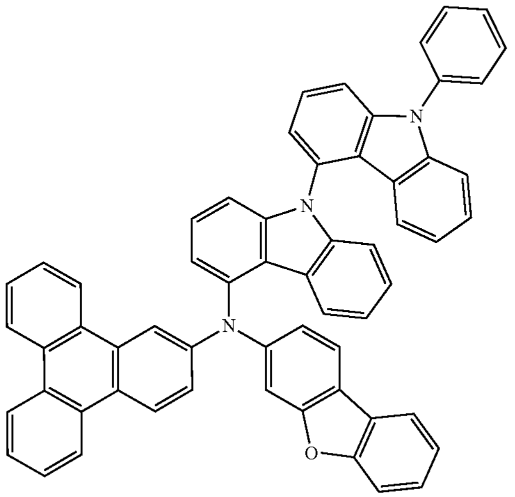
-continued
M30
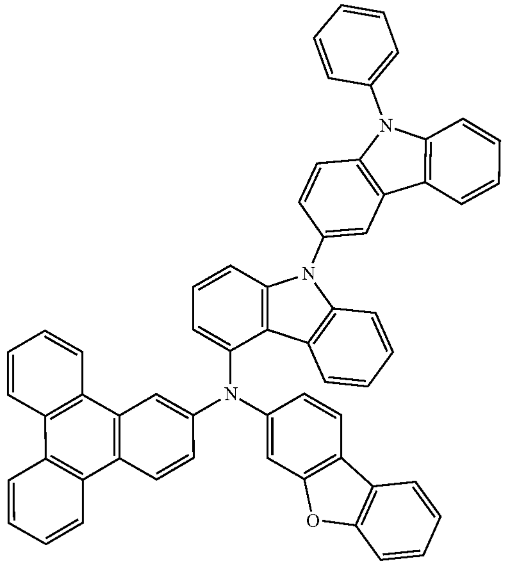
M31
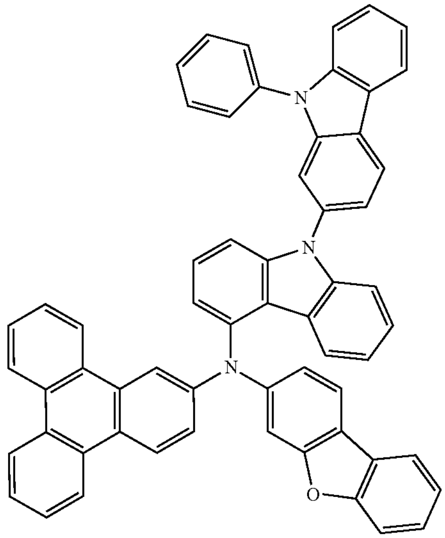
M32
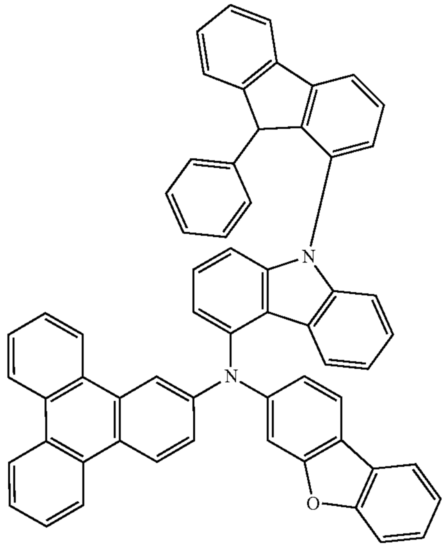

-continued
M33
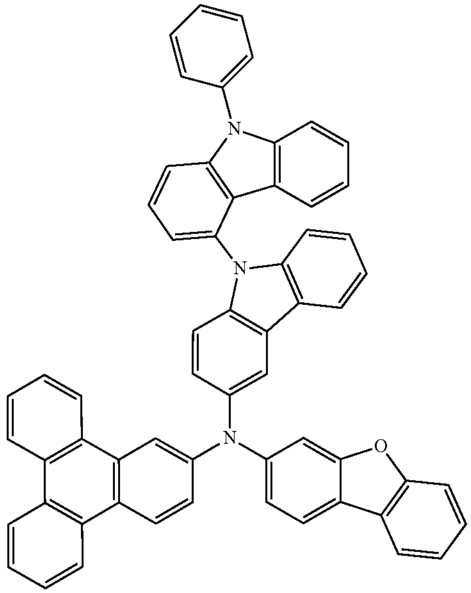
M34
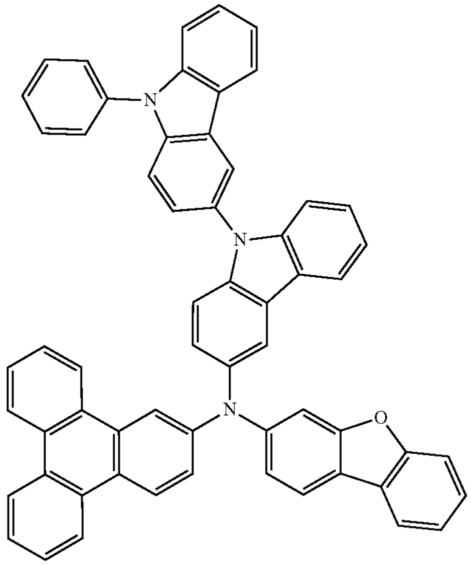
-continued
M35
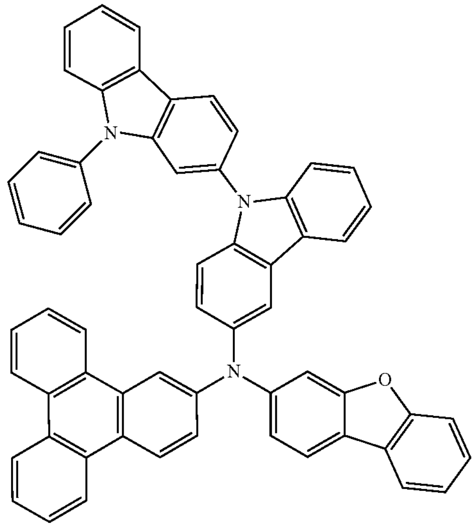
M36
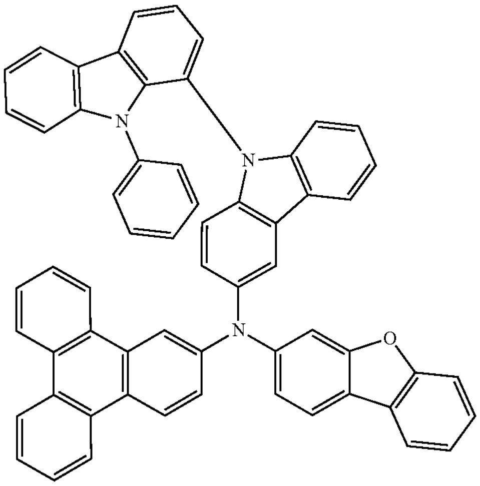
M37
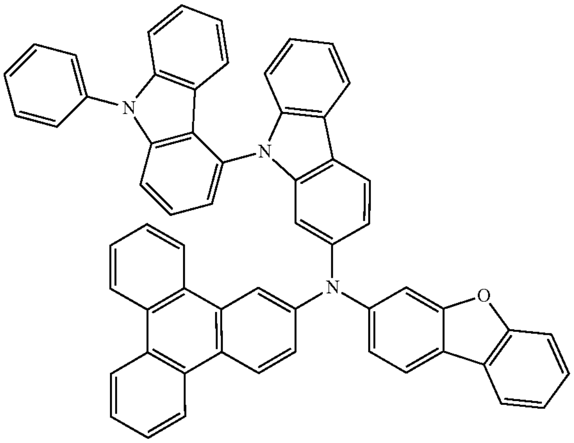

-continued
M38
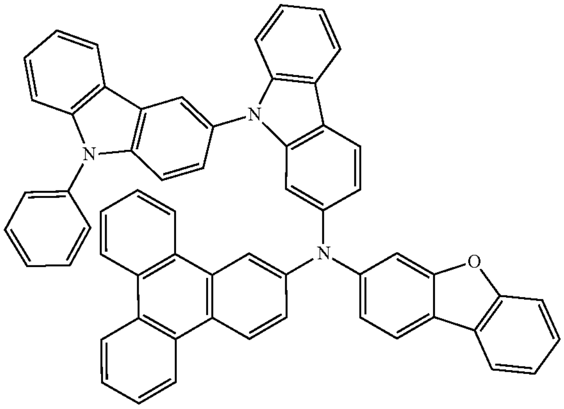
M39
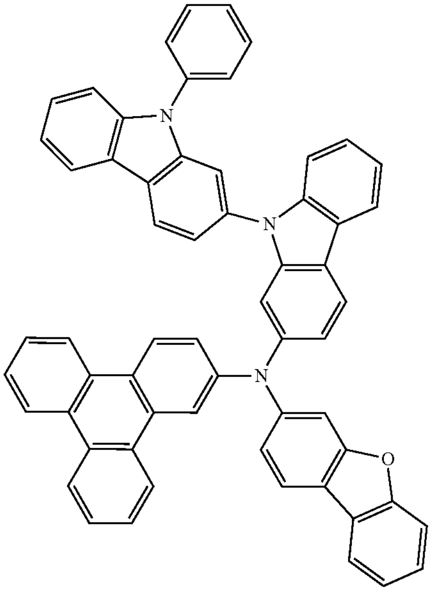
M40
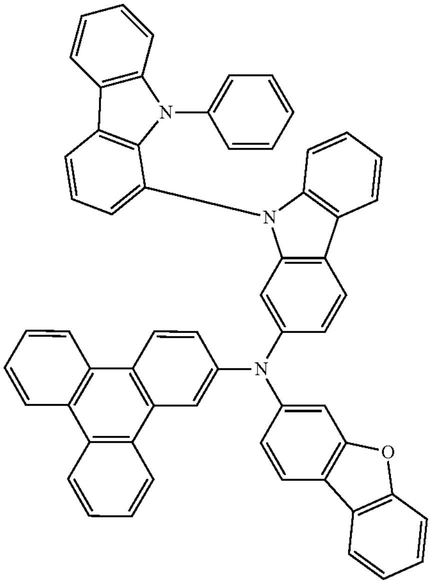
-continued
M41
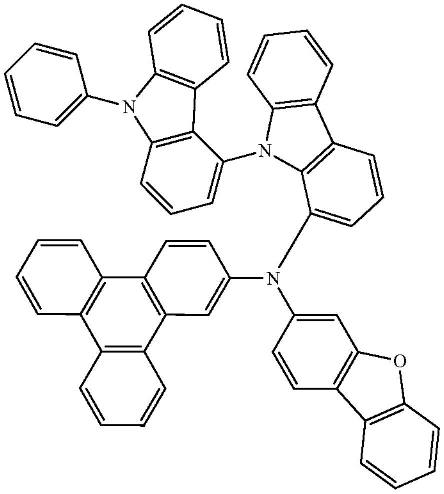
M42
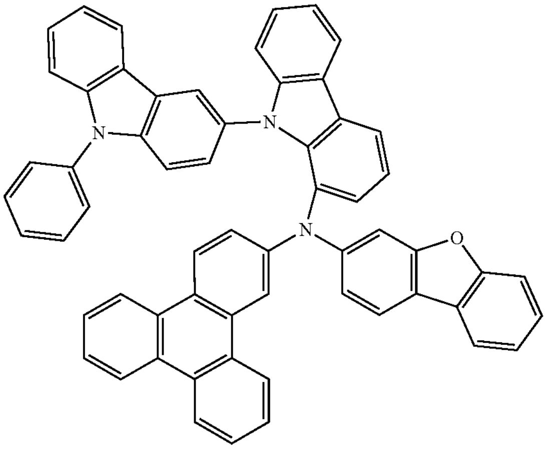
M43
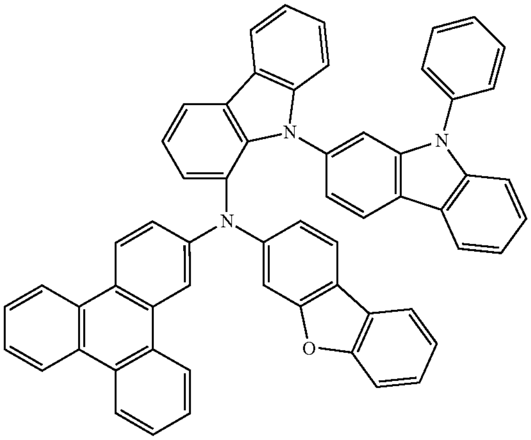

M44
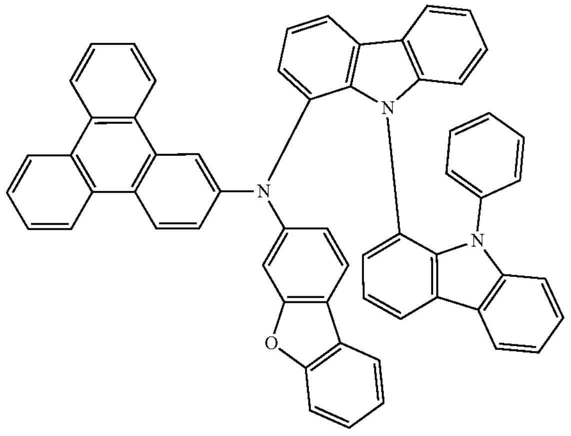
M45
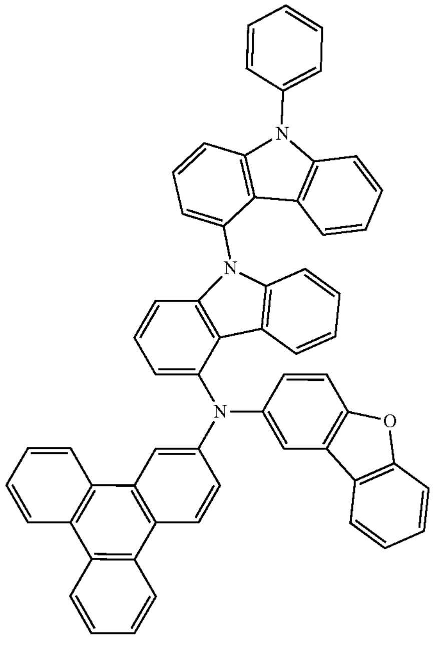
M46
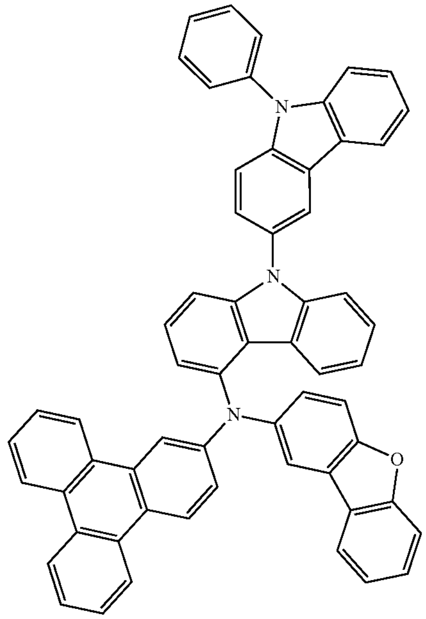
M47
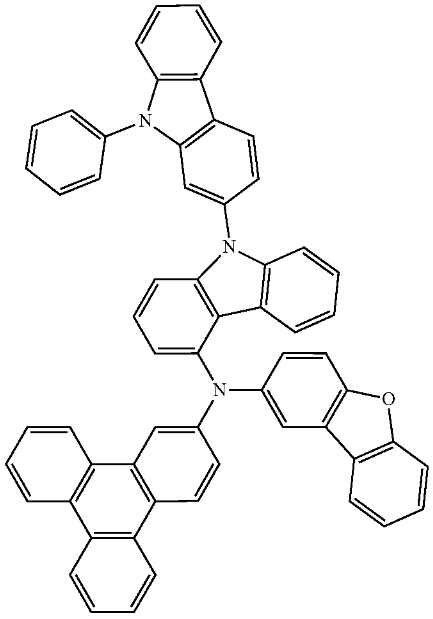

-continued
M48
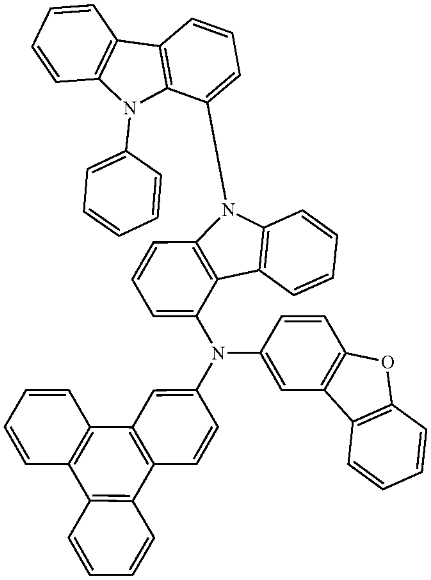
M49
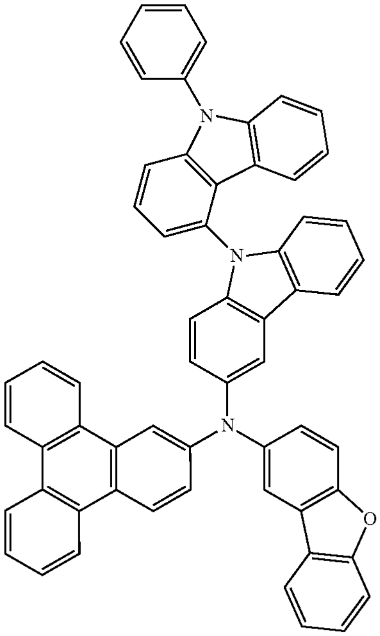
-continued
M50
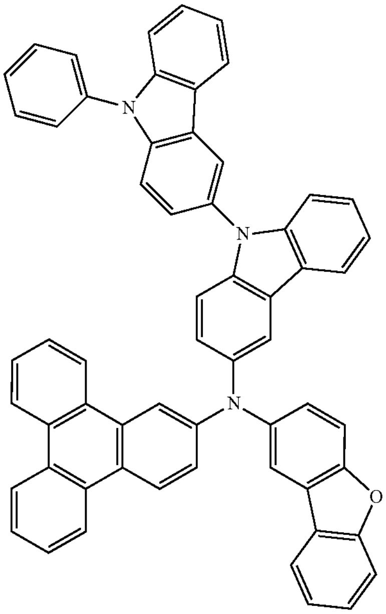
M51
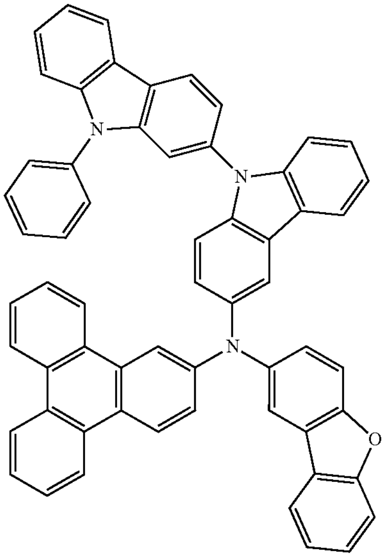

-continued
M52
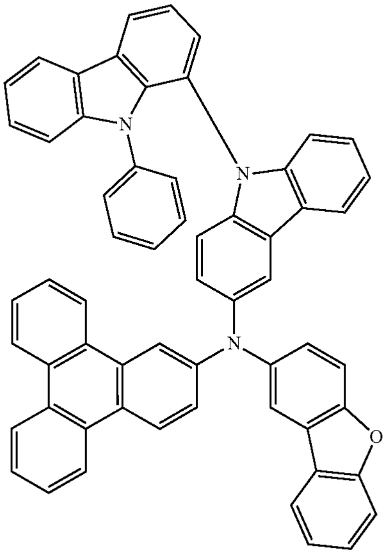
M53
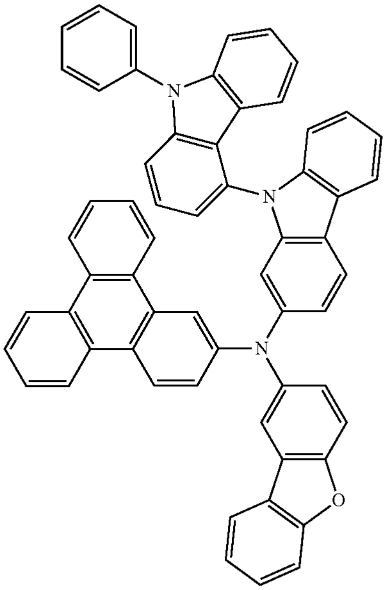
-continued
M54
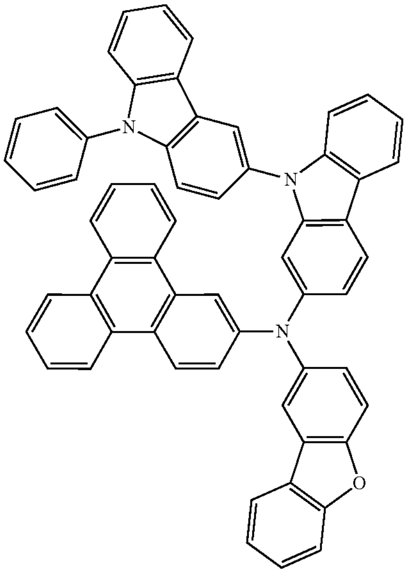
M55
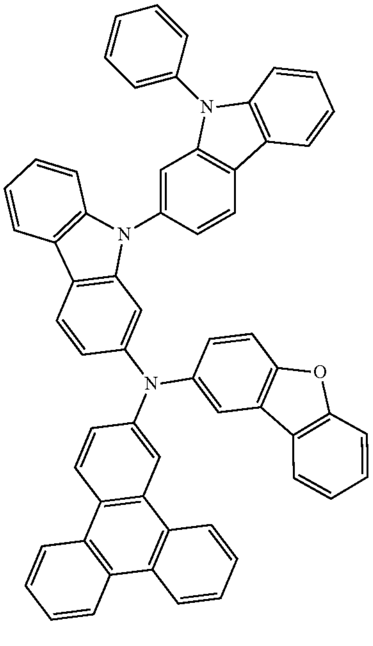

-continued
M56
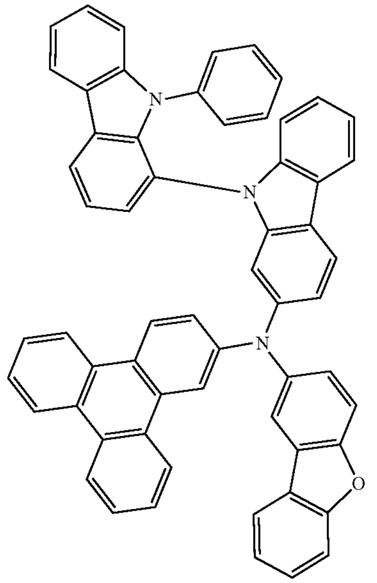
M57
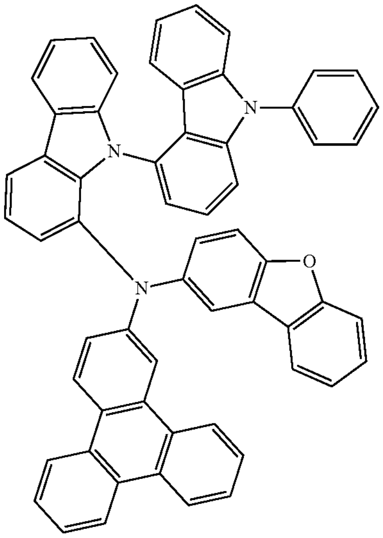
M58
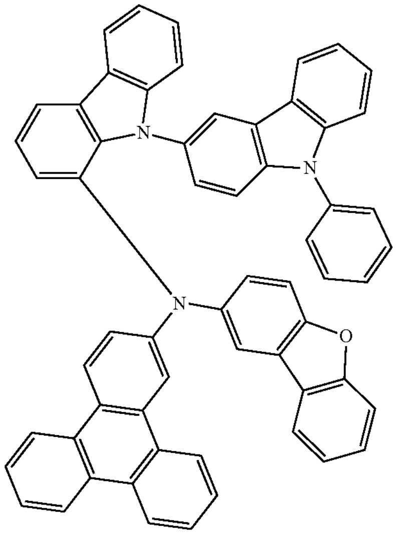
-continued
M59
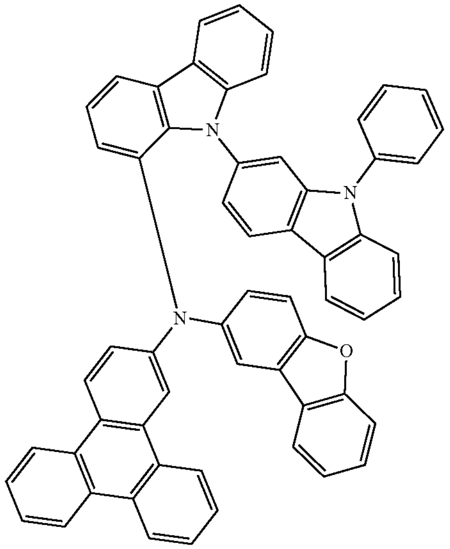
M60
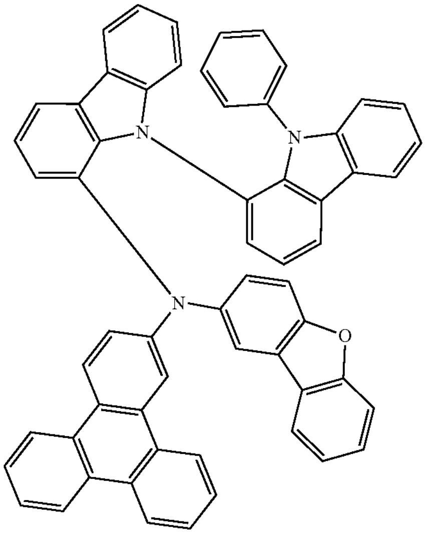

-continued
M61
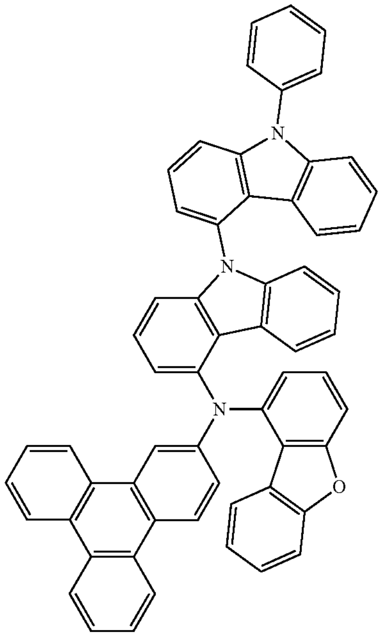
M62
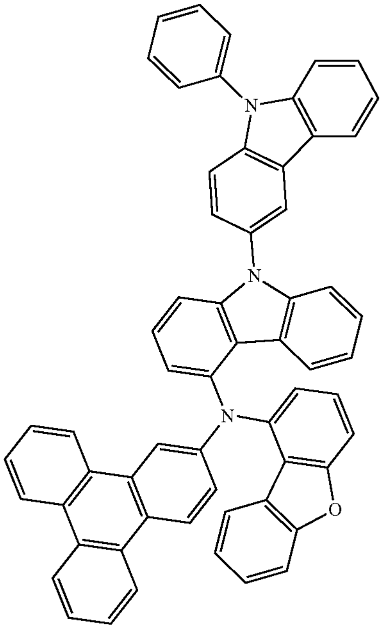
-continued
M63
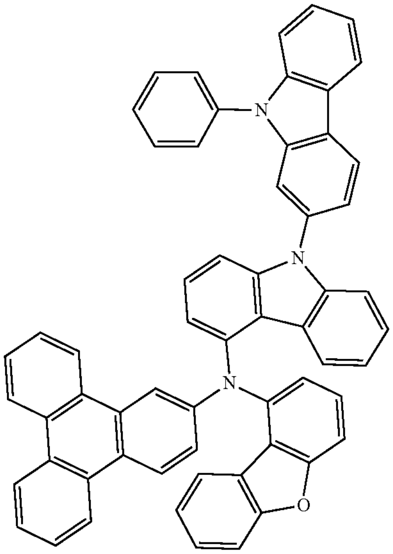
M64
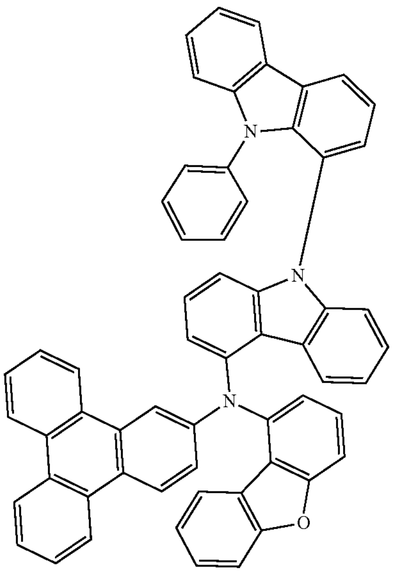

-continued
M65
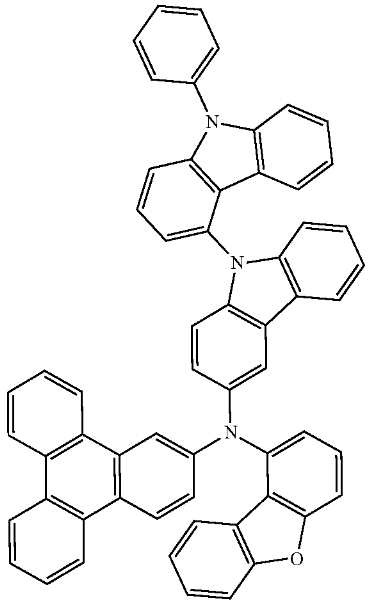
M66
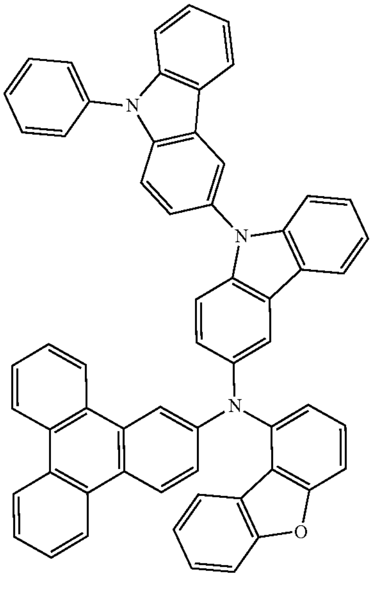
-continued
M67
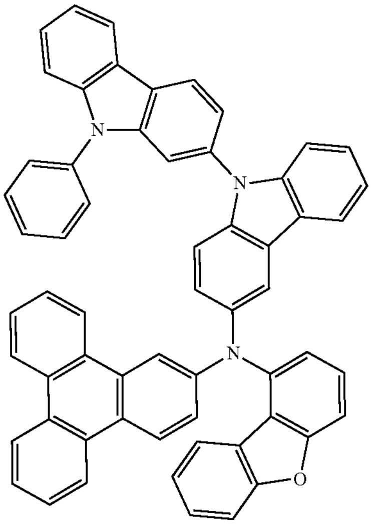
M68
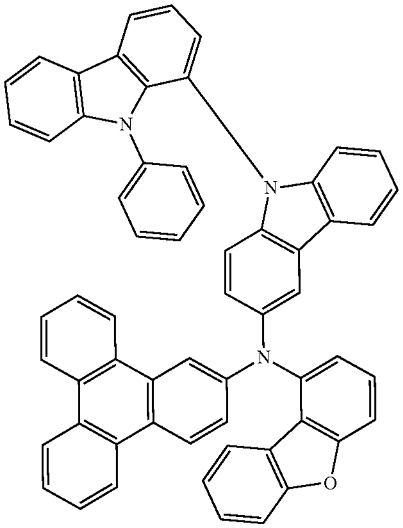
M69
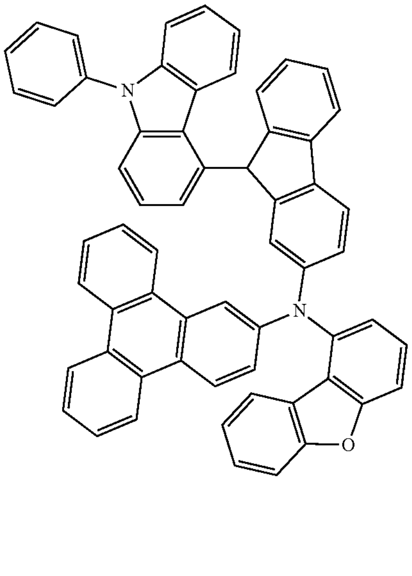

-continued
M70
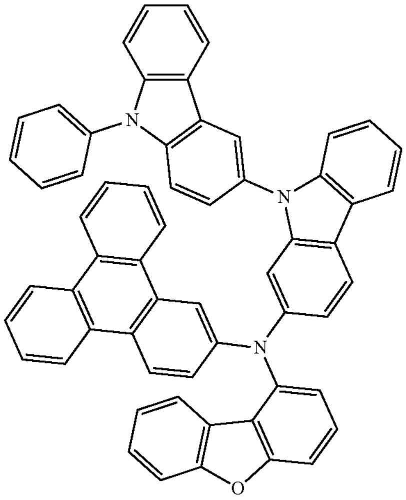
M71
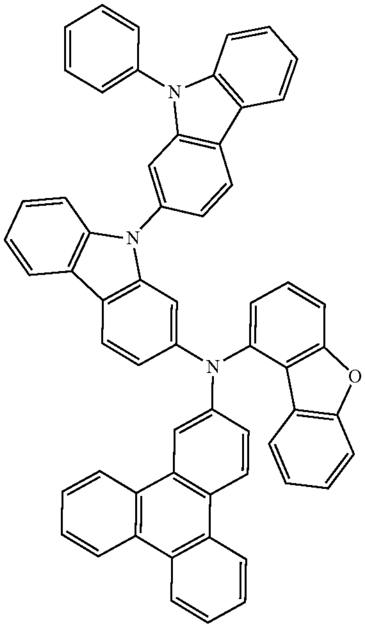
M72
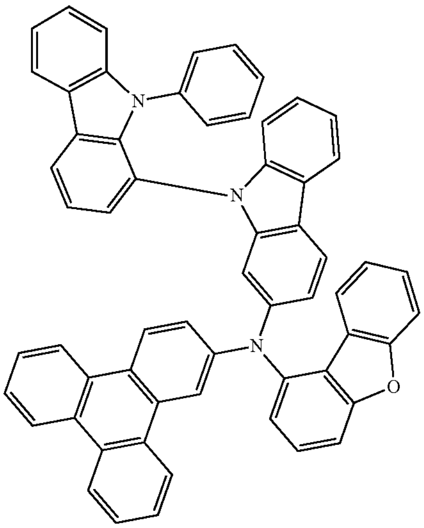
-continued
M73
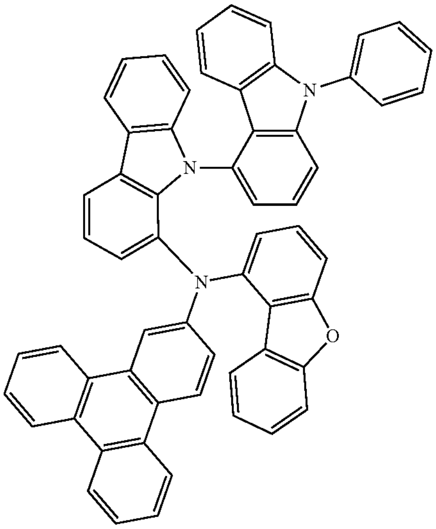
M74
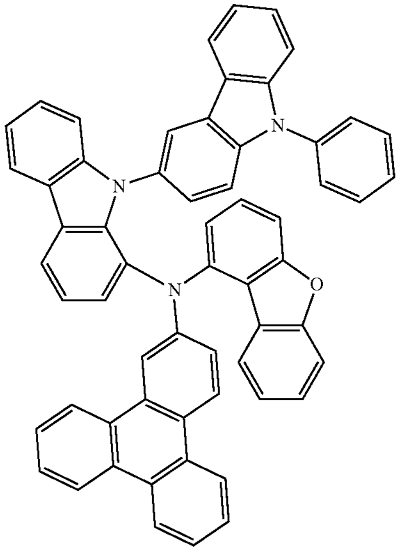
M75
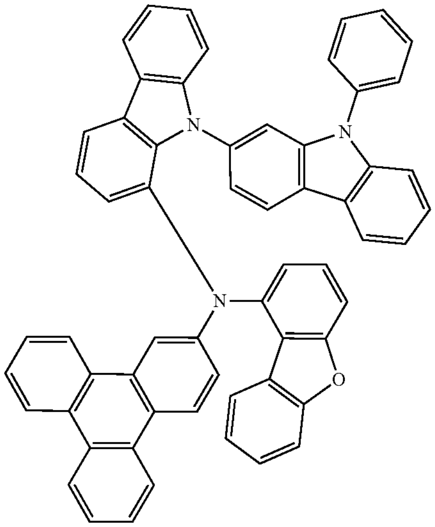

-continued
M76
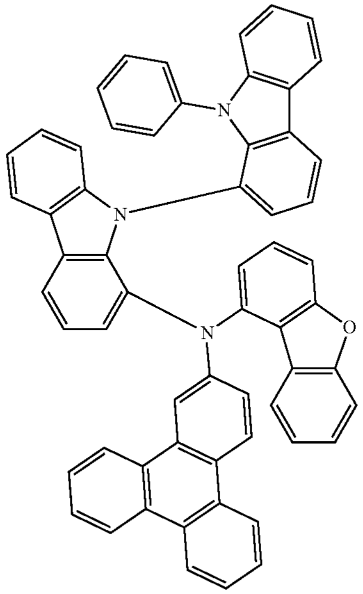
M77
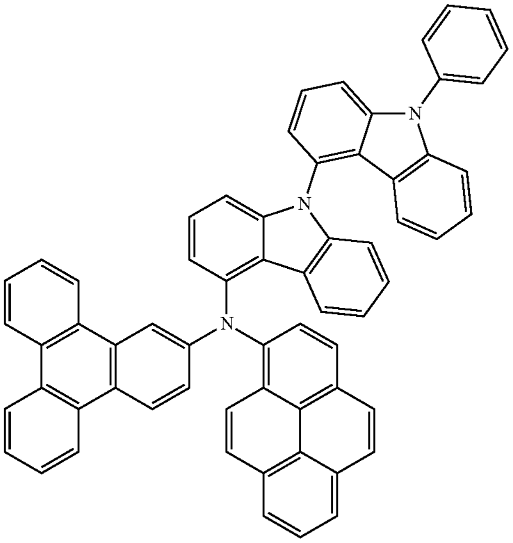
-continued
M78
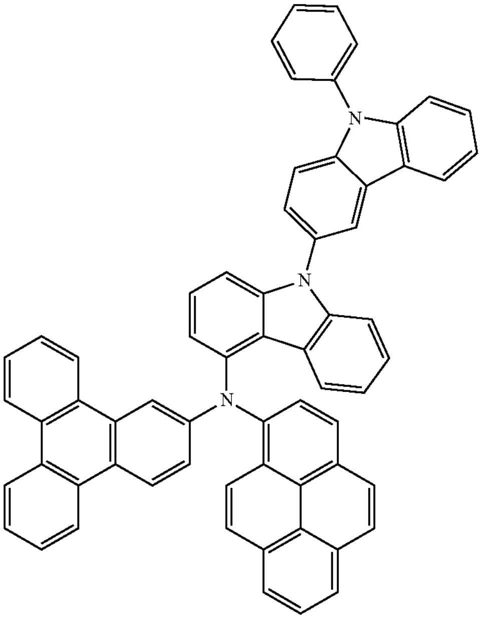
M79
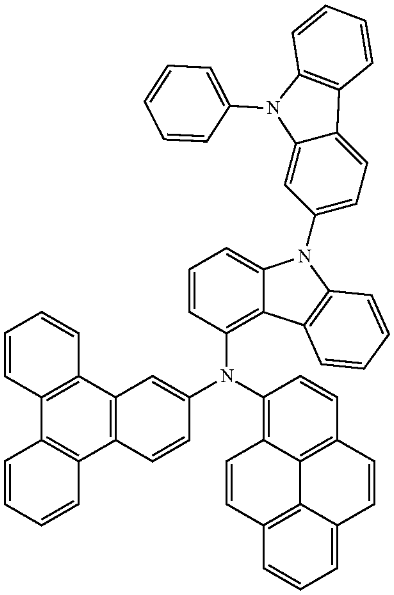

-continued

M80

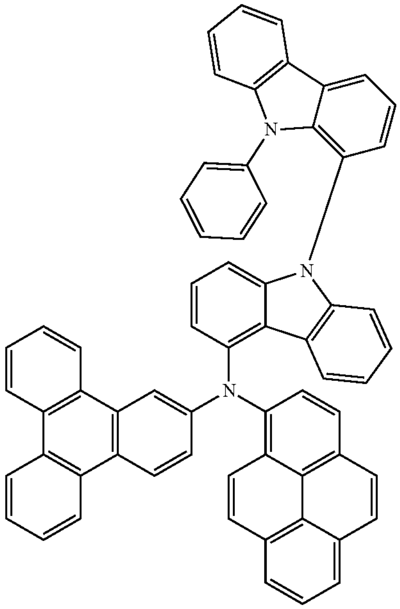

The compound of the present invention represented by the general formula (1) can be obtained by: synthesis by methods of various organic synthetic reactions established in the field of the organic synthetic chemistry including coupling reactions such as Suzuki coupling, Stille coupling, Grignard coupling, Ullmann coupling, Buchwald-Hartwig reaction, and Heck reaction, using commercially available reagents as raw materials; and then purification by using a known method such as recrystallization, column chromatography, and sublimation and purification. The method is not limited to this method.

The material for a photoelectric conversion element of the present invention preferably has an energy level of highest occupied molecular orbital (HOMO) obtained by structural optimization calculation with a density functional calculation B3LYP/6-31G (d) of −4.5 eV or lower, more preferably within a range of −4.5 eV to −6.0 eV.

The material for a photoelectric conversion element of the present invention preferably has an energy level of lowest unoccupied molecular orbital (LUMO) obtained by structural optimization calculation with a density functional calculation B3LYP/6-31G (d) of −2.5 eV or higher, more preferably within a range of −2.5 eV to −0.5 eV.

In the material for a photoelectric conversion element of the present invention, a difference (absolute value) between the HOMO energy level and the LUMO energy level is preferably within a range of 2.0 to 5.0 eV, and more preferably within a range of 2.5 to 4.0 eV.

The material for a photoelectric conversion element of the present invention preferably has a hole mobility of $1\times10^{-6}$ $cm^2/Vs$ to 1 $cm^2/Vs$, more preferably has a hole mobility of $1\times10^{-5}$ $cm^2/Vs$ to $1\times10^{-1}$ $cm^2/Vs$. The hole mobility can be evaluated by known methods such as a method with a FET-type transistor element, a method with a time-of-flight method, and an SCLC method.

The material for a photoelectric conversion element of the present invention is preferably amorphous. The amorphousness can be confirmed by various methods, and can be confirmed by, for example, detecting no peak in an XRD method or by detecting no endothermic peak in a DSC method.

Next, a photoelectric conversion element for imaging using the material for a photoelectric conversion element of the present invention will be described, but a structure of the photoelectric conversion element for imaging of the present invention is not limited thereto. The description will be made with reference to Drawing.

FIG. 1 is a sectional view schematically illustrating a structural example of the photoelectric conversion element for imaging of the present invention. In FIG. 1, 1 represents an electrode, 2 represents an electron blocking layer, 3 represents a photoelectric conversion layer, 4 represents a hole blocking layer, 5 represents an electrode, and 6 represents a substrate. The photoelectric conversion element is not limited to the structure in FIG. 1, and adding or omitting a layer can be made as necessary. An inverted structure of FIG. 1, that is, an electrode 6, a hole blocking layer 5, a photoelectric conversion layer 4, an electron blocking layer 3, and an electrode 2 may be stacked on a substrate 1 in this order. In this case, adding or omitting a layer can also be made as necessary. In the photoelectric conversion element for imaging as noted above, the layers constituting the stacked structure on the substrate other than electrodes, such as a positive electrode and a negative electrode, may be collectively referred to as an organic layer.

Electrode

An electrode used for the photoelectric conversion element for imaging using the material for a photoelectric conversion element for imaging of the present invention has a function of trapping a hole and an electron generated in the photoelectric conversion layer. A function to let light enter the photoelectric conversion layer is also required. Thus, at least one of two electrodes is desirably transparent or semi-transparent. A material used for the electrode is not particularly limited as long as it has conductivity, and examples thereof include: conductive transparent materials, such as ITO, IZO, $SnO_2$, ATO (antimony-doped tin oxide), ZnO, AZO (Al-doped zinc oxide), GZO (gallium-doped zinc oxide), $TiO_2$, and FTO; metals, such as gold, silver, platinum, chromium, aluminum, iron, cobalt, nickel, and tungsten; inorganic conductive substances, such as copper iodide and copper sulfide; and conductive polymers, such as polythiophene, polypyrrole, and polyaniline. A plurality of these materials may be mixed to use as necessary. In addition, two or more layers thereof may be stacked.

Photoelectric Conversion layer

The photoelectric conversion layer is a layer in which a hole and an electrode are generated by charge separation of an exciton generated by the incident light. The photoelectric conversion layer may be formed with a single photoelectric converting material, or may be formed by combination with a P-type organic semiconductor material being a hole transport material and an N-type organic semiconductor material being an electron transport material. Two or more kinds of the P-type organic semiconductor may be used, and two or more kinds of the N-type organic semiconductor may be used. One or more kinds of these P-type organic semiconductor and/or N-type organic semiconductor desirably use a dye material having a function of absorbing light with a desired wavelength in the visible region. As the P-type organic semiconductor material being the hole transport material, the compound of the present invention represented by the general formula (1) can be used.

The P-type organic semiconductor material may be any material having a hole transportability. The material represented by the general formula (1) is preferably used, but another P-type organic semiconductor material may be used. In addition, two or more kinds of the material represented by the general formula (1) may be mixed to use. Furthermore, the compound represented by the general formula (1) and another P-type organic semiconductor material may be mixed to use.

The another P-type organic semiconductor material may be any material having the hole transportability, and for example, usable are: compounds having a fused polycyclic aromatic group such as naphthalene, anthracene, phenanthrene, pyrene, chrysene, naphthacene, triphenylene, perylene, fluoranthene, fluorene, and indene; compounds having a π-excess aromatic group such as a cyclopentadiene derivative, a furan derivative, a thiophene derivative, a pyrrole derivative, a benzofuran derivative, a dibenzothiophene derivative, a dinaphthothienothiophene derivative, an indole derivative, a pyrazoline derivative, a dibenzofuran derivative, a dibenzothiophene derivative, a carbazole derivative, and indolocarbazole; an aromatic amine derivative, a styrylamine derivative, a benzidine derivative, a porphyrin derivative, a phthalocyanine derivative, and a quinacridone derivative.

In addition, examples of a polymer P-type organic semiconductor material include a polyphenylene-vinylene derivative, a polyparaphenylene derivative, a polyfluorene derivative, a polyvinylcarbazole derivative, and a polythiophene derivative. Two or more kinds selected from the compound represented by the general formula (1), the P-type organic semiconductor material, and the polymer P-type organic semiconductor material may be mixed to use.

The N-type organic semiconductor material may be any material having the electron transportability, and examples thereof include naphthalenetetracarboxylic diimide and perylenetetracarboxylic diimide, fullerenes, and azole derivatives such as imidazole, thiazole, thiadiazole, oxazole, oxadiazole, and triazole. Two or more kinds selected from the N-type organic semiconductor materials may be mixed to use.

Electron Blocking Layer

The electron blocking layer is provided in order to inhibit a dark current generated by injecting an electron from one electrode into the photoelectric conversion layer when a bias voltage is applied between the two electrodes. The electron blocking layer also has a function of hole transportation for transporting a hole generated by charge separation in the photoelectric conversion layer toward the electrode. A single layer or multiple layers of the electron blocking layer can be disposed as necessary. For the electron blocking layer, a P-type organic semiconductor material being the hole transport material can be used. The P-type organic semiconductor material may be any material having the hole transportability. Although the compound represented by the general formula (1) is preferably used, another P-type organic semiconductor material may be used. The compound represented by the general formula (1) and another P-type organic semiconductor material may be mixed to use. The other P-type organic semiconductor material may be any material having the hole transportability, and for example, usable are: compounds having a fused polycyclic aromatic group such as naphthalene, anthracene, phenanthrene, pyrene, chrysene, naphthacene, triphenylene, perylene, fluoranthene, fluorene, and indene; compounds having a T-excess aromatic group such as a cyclopentadiene derivative, a furan derivative, a thiophene derivative, a pyrrole derivative, a benzofuran derivative, a dibenzothiophene derivative, a dinaphthothienothiophene derivative, an indole derivative, a pyrazoline derivative, a dibenzofuran derivative, a dibenzothiophene derivative, and a carbazole derivative; an aromatic amine derivative, a styrylamine derivative, a benzidine derivative, a porphyrin derivative, a phthalocyanine derivative, and a quinacridone derivative.

In addition, examples of a polymer P-type organic semiconductor material include a polyphenylene-vinylene derivative, a polyparaphenylene derivative, a polyfluorene derivative, a polyvinylcarbazole derivative, and a polythiophene derivative. Two or more kinds selected from the compound of the present invention represented by the general formula (1), the P-type organic semiconductor material, and the polymer P-type organic semiconductor material may be mixed to use.

Hole Blocking Layer

The hole blocking layer is provided in order to inhibit a dark current generated by injecting a hole from one electrode into the photoelectric conversion layer when a bias voltage is applied between the two electrodes. The hole blocking layer also has a function of electron transportation for transporting an electron generated by charge separation in the photoelectric conversion layer toward the electrode. A single layer or multiple layers of the hole blocking layer can be disposed as necessary. For the hole blocking layer, the N-type organic semiconductor material having the electron transportability can be used. The N-type organic semiconductor material may be any material having the electron transportability, and examples thereof include: polycyclic aromatic multivalent carboxylic anhydride or imidized products thereof, such as naphthalenetetracarboxylic diimide and perylenetetracarboxylic diimide; fullerenes, such as C60 and C70; azole derivatives, such as imidazole, thiazole, thiadiazole, oxazole, oxadiazole, and triazole; a tris(8-quinolinolate)aluminum (III) derivative, a phosphine oxide derivative, a nitro-substituted fluorene derivative, a diphenylquinone derivative, a thiopyran dioxide derivative, a carbodiimide, a fluorenylidene methane derivative, an anthraquinodimethane derivative and an anthrone derivative, a bipyridine derivative, a quinoline derivative, and an indolocarbazole derivative. Two or more kinds of these N-type organic semiconductor materials may be mixed to use.

Hydrogen in the material of the present invention may be deuterium. That is, a part or all of hydrogens on the aromatic rings in the general formula (1) or formulae (2) to (4), and hydrogen of the substituents may be deuterium. Furthermore, a part or all of hydrogens in a compound used as the N-type organic semiconductor material and the P-type organic semiconductor material may be deuterium.

A method for producing a film of each layer in producing the photoelectric conversion element for imaging of the present invention is not particularly limited. The photoelectric conversion element may be produced by any one of dry process and wet process. The organic layer containing the material for a photoelectric conversion element of the present invention may be a plurality of the layers as necessary.

EXAMPLES

Hereinafter, the present invention will be described in more detail with Examples, but the present invention is not limited to these Examples.

Calculation Example Calculation of HOMO and LUMO

Calculated were HOMO and LUMO of the above compounds T1, T28, T37, T43, T58, T72, P22, P43, D3, D22, and M17. The calculation was performed by using a density functional theory (DFT), using Gaussian as a calculation program, and with structural optimization calculation of a density functional calculation B3LYP/6-31G (d). Table 1 shows the results. It can be mentioned that any of the materials for the photoelectric conversion element for imaging of the present invention has preferable HOMO and LUMO values.

As comparison, HOMO and LUMO of the compounds H1 and H2 were calculated by the same method.

[C15]

(H1)

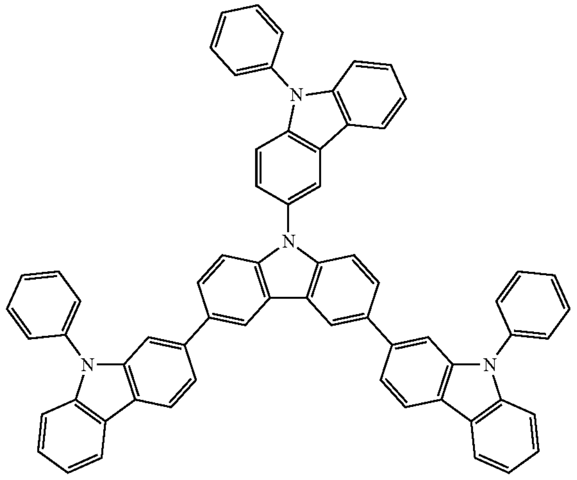

(H2)

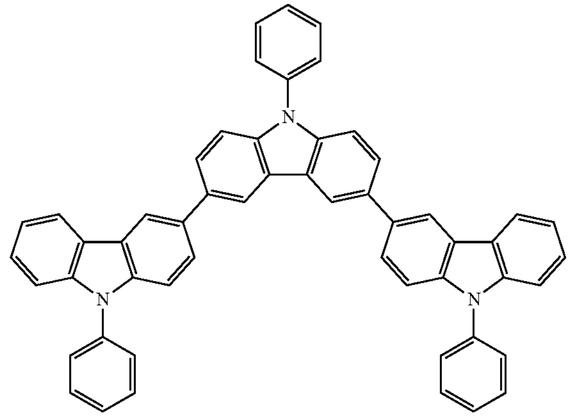

TABLE 1

| Compound | HOMO[eV] | LUMO[eV] | Compound | HOMO[eV] | LUMO[eV] |
|---|---|---|---|---|---|
| T1 | -4.9 | -1.1 | P43 | -5.0 | -1.8 |
| T28 | -4.9 | -1.1 | D3 | -5.0 | -1.0 |
| T37 | -5.1 | -1.7 | D22 | -5.2 | -1.6 |
| T43 | -5.0 | -1.2 | M17 | -4.7 | -1.0 |
| T58 | -5.0 | -1.8 | H1 | -4.9 | -1.0 |
| T72 | -4.6 | -1.0 | H2 | -4.9 | -0.7 |
| P22 | -4.9 | -1.6 | | | |

Synthesis examples of the compounds T28, T37, T43, and P22 will be described below as representative examples. The other compounds were also synthesized by similar methods.

Synthesis Example 1 (Synthesis of Compound T28)

[C16]

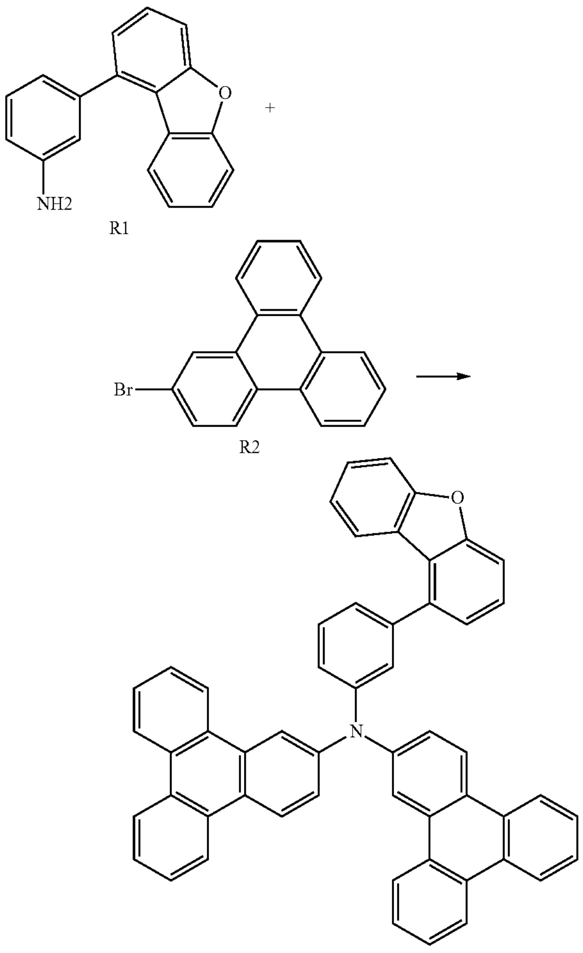

R1 + R2 → T28

Into a three-necked 1000-ml flask with degassed and nitrogen-replenished, R1 (19.3 mmol), R2 (39.5 mmol), trisdibenzylideneacetone dipalladium (1.0 mmol), tritertiarybutylphosphine (3.9 mmol), and sodium tertiarybutoxide (57.8 mmol) were added, 100 ml of xylene was added thereinto, and then the mixture was stirred at 120° C. for 3 hours. The mixture was once cooled to a room temperature, and then 200 ml of water and 200 ml of dichloromethane were added and transferred to a separatory funnel, and separation into an organic layer and an aqueous layer was performed. The organic layer was washed three times with 500 ml of water, the obtained organic layer was dehydrated with magnesium sulfate, and then concentrated under a reduced pressure. The obtained residue was purified by column chromatography to obtain T28 (pale yellow solid). The obtained solid was evaluated by an XRD method but no peak was detected. Thus, this compound was found to be amorphous.

Synthesis Example 2 (Synthesis of Compound T37)

[C17]

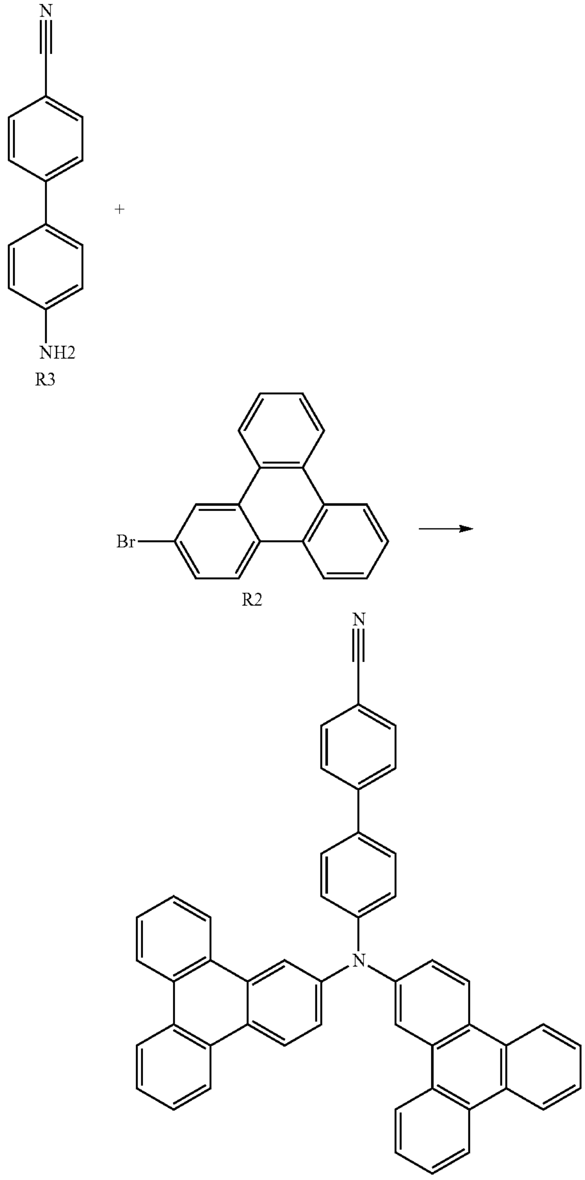

R3

R2

T37

Into a three-necked 1000-ml flask with degassed and nitrogen-replenished, R3 (25.7 mmol), R2 (54.1 mmol), trisdibenzylideneacetone dipalladium (0.8 mmol), tritertiarybutylphosphine (3.9 mmol), and sodium tertiarybutoxide (103.0 mmol) were added, 100 ml of xylene was added thereinto, and then the mixture was stirred at 120° C. for 3 hours. The mixture was once cooled to a room temperature, then 200 ml of water and 200 ml of dichloromethane were added, the mixture was transferred into a separatory funnel and separation into an organic layer and an aqueous layer was performed. The organic layer was washed three times with 500 ml of water, the obtained organic layer was dehydrated with magnesium sulfate, and then concentrated under a reduced pressure. The obtained residue was purified by column chromatography to obtain T37 (pale yellow solid). The obtained solid was evaluated by an XRD method but no peak was detected.

Synthesis Example 3 (Synthesis of Compound T43)

[C18]

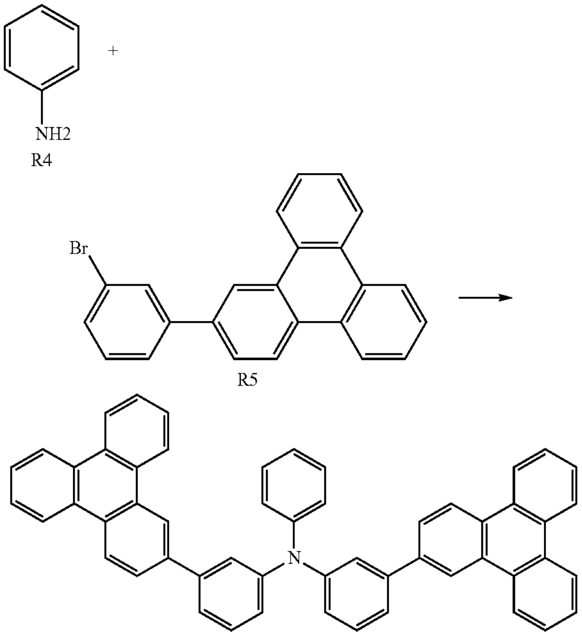

R4

R5

T43

Into a three-necked 1000-ml flask with degassed and nitrogen-replenished, R4 (21.5 mmol), R5 (47.2 mmol), trisdibenzylideneacetone dipalladium (0.9 mmol), tritertiarybutylphosphine (4.3 mmol), and sodium tertiarybutoxide (53.7 mmol) were added, 100 ml of xylene was added thereinto, and then the mixture was stirred at 120° C. for 3 hours. The mixture was once cooled to a room temperature, then 200 ml of water and 200 ml of dichloromethane were added, the mixture was transferred into a separatory funnel and separation into an organic layer and an aqueous layer was performed. The organic layer was washed three times with 500 ml of water, the obtained organic layer was dehydrated with magnesium sulfate, and then concentrated under a reduced pressure. The obtained residue was purified by column chromatography to obtain T43 (pale yellow solid). The obtained solid was evaluated by an XRD method but no peak was detected.

Synthesis Example 4 (Synthesis of Compound P22)

[C19]

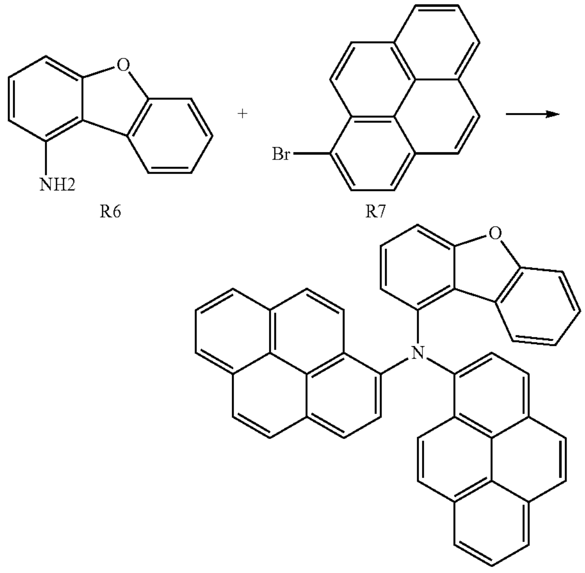

R6 R7 P22

Into a three-necked 1000-ml flask with degassed and nitrogen-replenished, R6 (16.4 mmol), R7 (33.6 mmol), trisdibenzylideneacetone dipalladium (0.8 mmol), tritertiarybutylphosphine (2.5 mmol), and sodium tertiarybutoxide (49.1 mmol) were added, 100 ml of xylene was added thereinto, and then the mixture was stirred at 120° C. for 3 hours. The mixture was once cooled to a room temperature, then 200 ml of water and 200 ml of dichloromethane were added, the mixture was transferred into a separatory funnel and separation into an organic layer and an aqueous layer was performed. The organic layer was washed three times with 500 ml of water, the obtained organic layer was dehydrated with magnesium sulfate, and then concentrated under a reduced pressure. The obtained residue was purified by column chromatography to obtain P22 (pale yellow solid). The obtained solid was evaluated by an XRD method but no peak was detected.

Example of Physical Properties Evaluation

On a glass substrate on which a transparent electrode composed of ITO with 110 nm in film thickness was formed, the compound T1 was produced to a film as an organic layer by a vacuum deposition method under a condition that a film thickness was approximately 3 μm. Subsequently, charge mobility was measured by a time-of-flight method using an element in which aluminum (Al) was formed with 70 nm in thickness as an electrode. As a result, the hole mobility was $4.5\times10^{-4}$ $cm^2/Vs$.

The hole mobilities were evaluated in the same procedure as above except that T37, T43, T72, P22, D3, D22, M17, H1 or H2 was used instead of the compound T1. Table 2 shows the results.

TABLE 2

| Compound | Hole mobility [$cm^2/Vs$] | Compound | Hole mobility [$cm^2/Vs$] |
|---|---|---|---|
| T1 | $4.5 \times 10^{-4}$ | D3 | $7.1 \times 10^{-4}$ |
| T37 | $3.5 \times 10^{-4}$ | D22 | $2.8 \times 10^{-4}$ |
| T43 | $2.1 \times 10^{-4}$ | M17 | $9.3 \times 10^{-4}$ |
| T72 | $8.1 \times 10^{-4}$ | H1 | $2.5 \times 10^{-5}$ |
| P22 | $2.1 \times 10^{-4}$ | H2 | $1.2 \times 10^{-5}$ |

Example 1

On a glass substrate on which an electrode composed of ITO with 70 nm in film thickness was formed, a 100-nm film of the compound T1 was formed with a vacuum degree of $4.0\times10^{-5}$ Pa as an electron blocking layer. Then, a 100-nm thin film of quinacridone was formed as a photoelectric conversion layer. Finally, a 70-nm aluminum film was formed as an electrode to produce a photoelectric conversion element for imaging. A current in a dark place was $5.6\times10^{-10}$ $A/cm^2$ with the electrodes of ITO and aluminum and with applying a voltage of 2 V. When a voltage of 2 V was applied on the ITO electrode (transparent conductive glass) side and the side was irradiated with light to be an irradiation light wavelength of 500 nm, a current was $5.9\times10^{-7}$ $A/cm^2$. A contrast ratio with applying a voltage of 2 V on the transparent conductive glass side was $1.0\times10^{3}$.

Comparative Example 1

On a glass substrate on which an electrode composed of ITO with 70 nm in film thickness was formed, a 100-nm film of the compound H1 was formed with a vacuum degree of $4.0\times10^{-5}$ Pa as an electron blocking layer. Then, a 100-nm thin film of quinacridone was formed as a photoelectric conversion layer. Finally, a 70-nm aluminum film was formed as an electrode to produce a photoelectric conversion element for imaging. A current in a dark place was $3.6\times10^{-9}$ $A/cm^2$ with the electrodes of ITO and aluminum and with applying a voltage of 2 V. When a voltage of 2 V was applied on the ITO electrode side and the side was irradiated with light to be an irradiation light wavelength of 500 nm, a current was $5.2\times10^{-7}$ $A/cm^2$. A contrast ratio with applying a voltage of 2 V on the transparent conductive glass side was $1.4\times10^{2}$.

Example 2

On an electrode composed of ITO with 70 nm in film thickness and formed on a glass substrate, a 10-nm film of the compound T1 was formed with a vacuum degree of $4.0\times10^{-5}$ Pa as an electron blocking layer. Then, 2Ph-BTBT, F6-SubPc-OC6F5, and fullerene (C60) were co-deposited at a deposition rate ratio of 4:4:2 with 200 nm to form a film as a photoelectric conversion layer. Subsequently, 10-nm of dpy-NDI was deposited to form a hole blocking layer. Finally, an aluminum film was formed with 70 nm in thickness as an electrode to produce a photoelectric conversion element. A current in a dark place (dark current) was $4.6\times10^{-10}$ $A/cm^2$ with the electrodes of ITO and aluminum and with applying a voltage of 2.6 V. When a voltage of 2.6 V was applied and the ITO electrode side was irradiated with light with an LED adjusted to be an irradiation light wavelength of 500 nm and 1.6 μW from a height of 10 cm, a current (bright current) was $2.5\times10^{-7}$ A/cm$^2$. A contrast ratio was $5.4\times10^2$ with applying a voltage of 2.6 V. Table 3 shows the results.

Examples 3 to 6

Photoelectric conversion elements were produced in the same manner as in Example 2 except that compounds shown in Table 3 were used as the electron blocking layer.

Comparative Examples 2 and 3×

Photoelectric conversion elements were produced in the same manner as in Example 2 except that compounds shown in Table 3 were used as the electron blocking layer.

Table 3 shows the results of Examples 3 to 6 and Comparative Examples 2 and 3.

The compounds used in Examples and Comparative Examples are shown below.

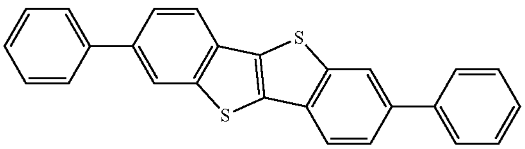

2Ph-BTBT

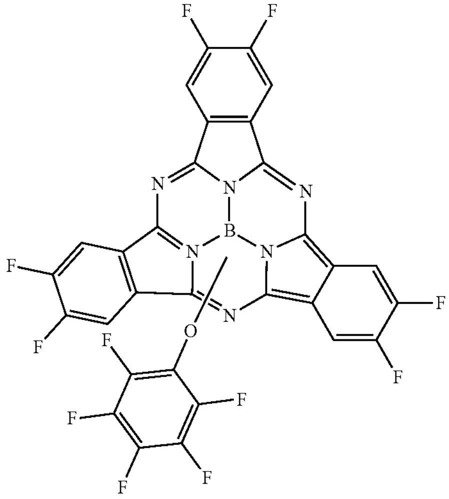

F6-SubPc-0C6F5

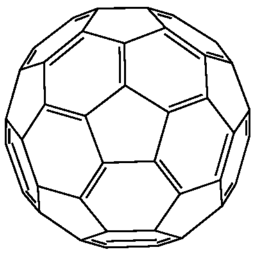

C60

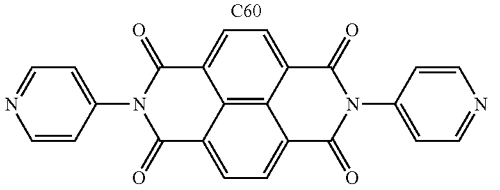

dpy-NDI

TABLE 3

| | Compound | Current value in dark place [A/cm$^2$] | Current value in light irradiation [A/cm$^2$] | Contrast ratio |
|---|---|---|---|---|
| Example 2 | T1 | $4.6\times10^{-10}$ | $2.5\times10^{-7}$ | $5.4\times10^{2}$ |
| Example 3 | T43 | $3.0\times10^{-10}$ | $2.3\times10^{-7}$ | $7.7\times10^{2}$ |
| Example 4 | T72 | $3.3\times10^{-10}$ | $2.2\times10^{-7}$ | $6.7\times10^{2}$ |
| Example 5 | D3 | $4.8\times10^{-10}$ | $2.5\times10^{-7}$ | $5.2\times10^{2}$ |
| Example 6 | M17 | $5.1\times10^{-10}$ | $2.5\times10^{-7}$ | $4.9\times10^{2}$ |
| Comparative Example 2 | H1 | $1.1\times10^{-9}$ | $2.1\times10^{-7}$ | $1.9\times10^{2}$ |
| Comparative Example 3 | H2 | $7.7\times10^{-10}$ | $2.4\times10^{-7}$ | $3.1\times10^{2}$ |

It is found from the results in Table 3 that the photoelectric conversion elements using the compound of the present invention exhibit a low dark current value and a high contrast ratio.

INDUSTRIAL APPLICABILITY

Using the material for a photoelectric conversion element for imaging of the present invention can achieve appropriate move of the hole and the electron in the photoelectric conversion element for imaging, and consequently enables to reduce a leakage current generated by applying a bias voltage during the conversion of light into electric energy. As a result, it is considered that a photoelectric conversion element that achieves a low dark current value and a high contrast ratio has been obtained. Therefore, the material of the present invention is useful as a material for a photoelectric conversion element for a photoelectric-converting film-stacked imaging device.

REFERENCE SIGNS LIST

1 Electrode
2 Electron blocking layer
3 Photoelectric conversion layer
4 Hole blocking layer
5 Electrode
6 Substrate

The invention claimed is:

1. A photoelectric conversion element for imaging, comprising a photoelectric conversion layer and an electron blocking layer between two electrodes, wherein at least one layer of the photoelectric conversion layer or the electron blocking layer contains a material for a photoelectric conversion element comprising a compound represented by the following formula (1);

(1)

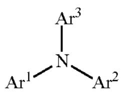

wherein $Ar^1$ to $Ar^3$ each independently represent a substituted or unsubstituted aromatic hydrocarbon group having 6 to 30 carbon atoms, a substituted or unsubstituted aromatic heterocyclic group having 3 to 30 carbon atoms, or a substituted or unsubstituted linked aromatic group in which two to six of the aromatic hydrocarbon group or the aromatic heterocyclic group are linked, at least two groups of $Ar^1$ to $Ar^3$ have an aromatic ring structure represented by any of the following formulae (2) to (4), and the aromatic ring structure optionally has a substituent, (2)

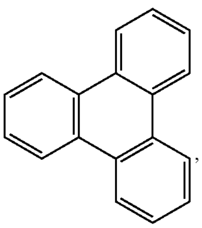

, (3)

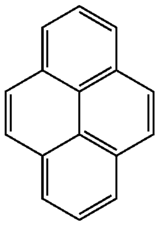

, (4)

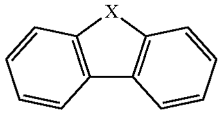

wherein X represents O or S.

2. The photoelectric conversion element for imaging, according to claim 1, wherein the electron blocking layer contains the material for a photoelectric conversion element according to claim 1.

3. The photoelectric conversion element for imaging according to claim 1, wherein the photoelectric conversion layer contains an electron transport material.

4. The photoelectric conversion element for imaging according to claim 1, wherein an energy level of the material of a highest occupied molecular orbital (HOMO) obtained by structural optimization calculation with a density functional calculation B3LYP/6-31G(d) is-4.5 eV or lower.

5. The photoelectric conversion element for imaging according to claim 4, wherein an energy level of the material of a lowest unoccupied molecular orbital (LUMO) obtained by the structural optimization calculation is −2.5 eV or higher.

6. The photoelectric conversion element for imaging according to claim 1, wherein the material has a hole mobility of $1\times10^{-6}$ $cm^2/Vs$ or more.

7. The photoelectric conversion element for imaging according to claim 1, wherein at least two groups of $Ar^1$ to $Ar^3$ of the compound represented by formula (1) has any one of the aromatic ring structure represented by formula (2) or (3).

8. The photoelectric conversion element for imaging according to claim 1, wherein at least two groups of $Ar^1$ to $Ar^3$ of the compound represented by formula (1) has any one of the aromatic ring structure represented by formula (2) or (4).

9. The photoelectric conversion element for imaging according to claim 1, wherein at least one group of $Ar^1$ to $Ar^3$ of the compound represented by formula (1) is the aromatic ring structure represented by formula (2), and at least another group of $Ar^1$ to $Ar^3$ has any one of the aromatic ring structure represented by formula (2) or (4).

10. The photoelectric conversion element for imaging according to claim 1, wherein the material is amorphous.

11. The photoelectric conversion element for imaging according to claim 1, wherein the material is used as a hole transport material.

* * * * *